United States Patent
Graetzel et al.

(10) Patent No.: US 12,251,175 B2
(45) Date of Patent: Mar. 18, 2025

(54) MEDICAL INSTRUMENT DRIVING

(71) Applicant: Auris Health, Inc., Santa Clara, CA (US)

(72) Inventors: Chauncey F. Graetzel, Palo Alto, CA (US); Polly Charlene Ma, Fremont, CA (US)

(73) Assignee: Auris Health, Inc., Santa Clara, CA (US)

( * ) Notice: Subject to any disclaimer, the term of this patent is extended or adjusted under 35 U.S.C. 154(b) by 104 days.

(21) Appl. No.: 17/353,381

(22) Filed: Jun. 21, 2021

(65) Prior Publication Data
US 2021/0393338 A1   Dec. 23, 2021

Related U.S. Application Data

(60) Provisional application No. 63/042,441, filed on Jun. 22, 2020.

(51) Int. Cl.
*A61B 34/00* (2016.01)
*A61B 5/00* (2006.01)
(Continued)

(52) U.S. Cl.
CPC ............ *A61B 34/25* (2016.02); *A61B 5/0036* (2018.08); *A61B 34/37* (2016.02); *A61B 34/70* (2016.02);
(Continued)

(58) Field of Classification Search
CPC ... A61B 34/37; A61B 34/25; A61B 2034/301; A61B 90/37; A61B 34/70; A61B 5/0036; A61B 90/00; A61B 34/00
See application file for complete search history.

(56) References Cited

U.S. PATENT DOCUMENTS

| 4,456,961 A | 6/1984 | Price et al. |
| 5,876,325 A | 3/1999 | Mizuno et al. |
| (Continued) | | |

FOREIGN PATENT DOCUMENTS

| CN | 107530138 A | 1/2018 |
| CN | 109069136 A | 12/2018 |
| (Continued) | | |

OTHER PUBLICATIONS

CN Office Action for Appl. No. 202180044513.0, dated Aug. 10, 2023, 10 pages.
(Continued)

*Primary Examiner* — Tuan H Nguyen
(74) *Attorney, Agent, or Firm* — Paradice & Li LLP

(57) ABSTRACT

Methods, systems, and devices for controlling a medical instrument are discussed herein. For example, image data can be received from a first instrument that is configured to access an anatomical site via a first access path. The image data can be representative of the anatomical site and a second instrument that is configured to access the anatomical site via a second access path. A visual representation of the image data can be displayed in a user interface and a first directional input signal can be received from an input device. An orientation of the first instrument relative to the second instrument can be determined. Movement of the second instrument can be controlled based at least in part on the first directional input signal and the orientation of the first instrument relative to the second instrument.

30 Claims, 23 Drawing Sheets

(51) Int. Cl.
*A61B 34/37* (2016.01)
*A61B 90/00* (2016.01)
*A61B 34/30* (2016.01)

(52) U.S. Cl.
CPC ........ *A61B 90/37* (2016.02); *A61B 2034/301* (2016.02); *A61B 2034/302* (2016.02)

(56) References Cited

U.S. PATENT DOCUMENTS

| | | | |
|---|---|---|---|
| 6,120,433 | A | 9/2000 | Mizuno et al. |
| 6,448,958 | B1 | 9/2002 | Muta |
| 6,799,065 | B1 | 9/2004 | Niemeyer |
| 8,002,694 | B2 | 8/2011 | Kishi et al. |
| 8,918,207 | B2 | 12/2014 | Prisco |
| 9,002,517 | B2 | 4/2015 | Bosscher et al. |
| 9,259,283 | B2 | 2/2016 | Ogawa et al. |
| 9,259,289 | B2 | 2/2016 | Zhao et al. |
| 10,639,108 | B2 * | 5/2020 | Romo ............... A61B 1/00135 |
| 10,827,913 | B2 * | 11/2020 | Ummalaneni ......... A61B 5/066 |
| 2003/0004610 | A1 | 1/2003 | Niemeyer et al. |
| 2006/0106493 | A1 | 5/2006 | Niemeyer et al. |
| 2006/0195228 | A1 | 8/2006 | Igarashi |
| 2008/0180392 | A1 | 7/2008 | Kishi |
| 2011/0276058 | A1 | 11/2011 | Choi et al. |
| 2012/0071895 | A1 | 3/2012 | Stahler et al. |
| 2015/0142171 | A1 | 5/2015 | Li et al. |
| 2015/0173837 | A1 | 6/2015 | Barnett |
| 2016/0135910 | A1 | 5/2016 | Hatta |
| 2016/0199984 | A1 | 7/2016 | Lohmeier |
| 2018/0071032 | A1 | 3/2018 | Barreto |
| 2018/0092700 | A1 | 4/2018 | Itkowitz et al. |
| 2018/0214011 | A1 | 8/2018 | Graetzel et al. |
| 2018/0279852 | A1 | 10/2018 | Rafii-Tari et al. |
| 2019/0175288 | A1 | 6/2019 | Herrell et al. |
| 2020/0078109 | A1 | 3/2020 | Steger |
| 2020/0100855 | A1 | 4/2020 | Leparmentier et al. |
| 2021/0121251 | A1 | 4/2021 | Aljuri et al. |
| 2021/0369355 | A1 | 12/2021 | Masaki et al. |

FOREIGN PATENT DOCUMENTS

| | | |
|---|---|---|
| CN | 110602976 A | 12/2019 |
| CN | 110831486 A | 2/2020 |
| CN | 109069136 B | 7/2021 |
| EP | 1973021 B1 | 4/2012 |
| EP | 1970169 B1 | 9/2016 |
| JP | 2002066970 A | 3/2002 |
| JP | 2003265500 A | 9/2003 |
| JP | 2008173724 A | 1/2012 |
| JP | 3210603 | 6/2017 |
| KR | 1020080027256 A | 3/2008 |
| WO | 0060996 A1 | 10/2000 |
| WO | 2014186715 A1 | 11/2014 |
| WO | 2015142953 A1 | 9/2015 |
| WO | 2016028858 A1 | 2/2016 |
| WO | 2016053657 A1 | 4/2016 |
| WO | 2016149320 A1 | 9/2016 |
| WO | 2017075574 A1 | 5/2017 |
| WO | 2018013979 S2 | 1/2018 |
| WO | 2018187069 A1 | 10/2018 |
| WO | 2019191143 A1 | 10/2019 |
| WO | 2019231895 A1 | 12/2019 |
| WO | 2020069404 A1 | 4/2020 |

OTHER PUBLICATIONS

International search report for appl No. PCTIB2021055490, dated Sep. 24, 2021, 4 pages.
International Search Report for appl No. PCTIB2021055494, dated Sep. 27, 2021, 4 pages.
Written opinion for appl No. PCTIB2021055490, dated Sep. 24, 2021, 4 pages.
Written opinion for appl No. PCTIB2021055494, dated Sep. 27, 2021, 4 pages.
CN 2nd Office Action for Appl. No. 202180044513.0, dated Jan. 26, 2024, 13 pages.
EP Search Report for Appl. No. 21828974.2, dated Jun. 17, 2024, 15 pages.
KR Preliminary Rejection for Appl. No. 10-2023-7002339, dated Jul. 5, 2024, 7 pages.
Non-Final Rejection for U.S. Appl. No. 17/353,550, dated Jun. 13, 2024, 17 pages.
Supplementary European Search Report, issued on Sep. 9, 2024, in European Patent Application No. 21828974.2, 14 pages.
Notice of Allowance from U.S. Appl. No. 17/353,550, dated Sep. 29, 2024, pp. 1-41.
Second Office Action for Korean Application No. 10-2023-7002339, dated Jan. 24, 2025, 16 pages.

* cited by examiner

DIRECT CONTROL MODE

INVERTED CONTROL MODE

MEDICAL INSTRUMENT DRIVING

RELATED APPLICATION(S)

This application claims priority to U.S. Provisional Application No. 63/042,441, filed Jun. 22, 2020, and entitled MEDICAL INSTRUMENT DRIVING, the disclosure of which is hereby incorporated by reference in its entirety.

BACKGROUND

Field

The present disclosure relates to the field of medical devices and procedures.

Description of Related Art

Various medical procedures involve the use of one or more scope and/or percutaneous access instruments. Certain operational processes can involve inserting one or more devices through the skin and/or other anatomy of a patient to reach a treatment site and extract an object from the patient, such as a urinary stone. The improper positioning or advancement of such devices can result in certain physiological and procedural complications.

SUMMARY

In some implementations, the present disclosure relates to a control system comprising a communication interface configured to receive image data from a first instrument that is configured to access an anatomical site via a first access path, and control circuitry communicatively coupled to the communication interface. The image data is representative of the anatomical site and a second instrument that is configured to access the anatomical site via a second access path. The control circuitry is configured to cause a visual representation of the image data to be displayed in a user interface, receive a first directional input signal from an input device, determine an orientation of the first instrument relative to the second instrument, and control movement of the second instrument based at least in part on the first directional input signal and the orientation of the first instrument relative to the second instrument.

In some embodiments, the first directional input signal is associated with a first direction relative to the input device and the first direction is associated with a first horizontal component. The control circuitry can be configured to determine to control the second instrument in an inverted control mode and, based at least in part on the inverted control mode, control the second instrument to move in a second direction relative to a frame of reference for the second instrument. The second direction can be associated with a second horizontal component that has an opposite sign to the first horizontal component. The frame of reference for the second instrument can comprise at least one of a control frame for the second instrument or a coordinate frame for the second instrument.

In some embodiments, the first directional input signal is associated with a first direction relative to the input device and the first direction is associated with a first horizontal component. The control circuitry can be configured to determine to control the second instrument in a direct control mode and, based at least in part on the direct control mode, control the second instrument to move in a second direction relative to a frame of reference for the second instrument. The second direction can be associated with a second horizontal component that has a same sign as the first horizontal component.

In some embodiments, the first directional input signal is associated with a first direction relative to the input device and the first direction is associated with a first horizontal component. The control circuitry can be configured to determine to control the second instrument in an inverted control mode, based at least in part on the inverted control mode, control the second instrument to move in a second direction relative to a frame of reference for the second instrument. The second direction can be associated with a second horizontal component that has an opposite sign to the first horizontal component. The control circuitry can further be configured to determine to control the second instrument in a direct control mode, receive a second directional input signal from the input device. The second directional input signal can be associated with a third direction relative to the input device and the third direction can be associated with a third horizontal component. The control circuitry can further be configured to, based at least in part on the direct control mode, control the second instrument to move a fourth direction relative to the frame of reference for the second instrument. The fourth direction can be associated with a fourth horizontal component that has a same sign as the third horizontal component.

In some embodiments, the first directional input signal is based at least in part on input received via a directional control on the input device. The control circuitry can be configured to determine to control the second instrument in an inverted control mode, based on the directional control being associated with insertion, control the second instrument to be retracted, and based on the directional control being associated with retraction, control the second instrument to be inserted.

In some embodiments, the control circuitry is configured to determine a control mode from among a plurality of control modes based at least in part on the orientation of the first instrument relative to the second instrument and control the movement of the second instrument based at least in part on the control mode.

In some implementations, the present disclosure relates to a system comprising a first robotic manipulator configured to manipulate a direct access instrument at a target anatomical site, a second robotic manipulator configured to manipulate a percutaneous access instrument at the target anatomical site, a user input device including a directional control, and control circuitry communicatively coupled to the first robotic manipulator, the second robotic manipulator, and the user input device. The user input device is configured to receive user input via the directional control and generate a first directional input signal based at least in part on the user input. The control circuitry is configured to receive image data from the direct access instrument, generate user interface data representing the image data, determine an orientation of the direct access instrument relative to the percutaneous access instrument, and control the second robotic manipulator based at least in part on the first directional input signal and the orientation of the direct access instrument relative to the percutaneous access instrument. The image data represents at least a portion of the percutaneous access instrument.

In some embodiments, the first directional input signal is associated with a first direction relative to the user input device and the first direction is associated with a first horizontal or vertical component. The control circuitry can be configured to control the second robotic manipulator to move the percutaneous access instrument in a second direction relative to a frame of reference for the percutaneous access instrument based at least in part on an inverted control mode. The second direction can be associated with a second horizontal or vertical component that has an opposite sign to the first horizontal or vertical component. In some embodiments, the control circuitry can be further configured to determine the inverted control mode based on at least one of input received via a user interface or input received via the user input device. In some embodiments, the control circuitry is further configured to determine the inverted control mode based at least in part on the orientation of the direct access instrument relative to the percutaneous access instrument. The first horizontal or vertical direction can be left or right.

In some embodiments, the first directional input signal is associated with a first direction relative to the user input device and the first direction is associated with a first horizontal or vertical component. The control circuitry can be configured to control the second robotic manipulator to move the percutaneous access instrument in a second direction relative to a frame of reference for the second instrument. The second direction can be associated with a second horizontal or vertical component that has a same sign as the first horizontal or vertical component.

In some embodiments, the control circuitry is further configured to receive an input signal indicating to switch control to the direct access instrument, based at least in part on the input signal, configure the system to control the direct access instrument, receive, from the user input device, a second directional input signal, and control the direct access instrument based at least in part on the second directional input signal.

In some embodiments, the direct access instrument comprises an endoscope and the percutaneous access instrument comprises a catheter.

In some implementations, the present disclosure relates to a method comprising receiving, by control circuitry, image data from an endoscope that is configured to access an anatomical site via a first access path. The image data represents at least a portion of a catheter that is configured to access the anatomical site via a second access path. The method further comprises displaying a visual representation of the image data in a user interface, receiving, by the control circuitry and from an input device, a first directional input signal, determining an orientation of the endoscope relative to the catheter, and controlling, by the control circuitry, movement of the catheter based at least in part on the first directional input signal and the orientation of the endoscope relative to the catheter.

In some embodiments, the method further comprises determining an inverted control mode for the catheter. The first directional input signal can be associated with a first direction relative to the input device and the first direction can be associated with a first horizontal component. The controlling movement of the catheter can be based at least in part on the inverted control mode, where the catheter is controlled to move in a second direction relative to a frame of reference for the catheter. The second direction can be associated with a second horizontal component that has an opposite sign to the first horizontal component. In some embodiments, the method further comprises receiving, via at least one of the input device or the user interface, input indicating the inverted control mode. The determining the inverted control mode can be based at least in part on the input. In some embodiments, the determining the inverted control mode is based at least in part on the orientation of the endoscope relative to the catheter.

In some embodiments, the method further comprises determining a direct control mode for the catheter, receiving, from the input device, a second directional input signal that is associated with a third direction relative to the input device, the third direction being associated with a third horizontal component, and controlling movement of the catheter based at least in part on the direct control mode. The catheter can be controlled to move in a fourth direction relative to the frame of reference for the catheter. The fourth direction can be associated with a fourth horizontal component that has a same sign as the third horizontal component.

In some embodiments, the method further comprises receiving an input signal indicating to switch control to the endoscope, receiving, from the input device, a second directional input signal, and controlling movement of the endoscope based at least in part on the input signal and the second directional input signal. The first access path can comprise a natural lumen in a patient and the second access path can comprise a percutaneous access path in the patient.

In some implementations, the present disclosure relates to one or more non-transitory computer-readable media storing computer-executable instructions that, when executed by control circuitry, cause the control circuitry to perform operations comprising receiving image data from an endoscope that is configured to access an anatomical site via a first access path, causing a visual representation of the image data to be displayed in a user interface, receiving, from an input device, a first directional input signal, and controlling movement of a catheter based at least in part on the first directional input signal and an orientation of the endoscope relative to the catheter. The image data represents at least a portion of the catheter that is configured to access the anatomical site via a second access path.

In some embodiments, the operations further comprise determining a first control mode for the catheter. The first directional input signal can be associated with a first direction relative to the input device and the first direction can be associated with a first horizontal component. The controlling movement of the catheter can be based at least in part on the first control mode and the catheter can be controlled to move in a second direction relative to a frame of reference for the catheter. The second direction can be associated with a second horizontal component that has an opposite sign to the first horizontal component.

In some embodiments, the frame of reference for the catheter comprises at least one of a control frame for the catheter or a coordinate frame for the catheter. In some embodiments, the determining the first control mode is based at least in part on the orientation of the endoscope relative to the catheter. In some embodiments, the operations further comprise determining a second control mode for the catheter, receiving, from the input device a second directional input signal that is associated with a third direction relative to the input device. The third direction can be associated with a third horizontal component. The operations can further comprise controlling movement of the catheter based at least in part on the second control mode. The catheter can be controlled to move in a fourth direction relative to the frame of reference for the catheter. The fourth direction can be associated with a fourth horizontal component that has a same sign as the third horizontal component.

In some embodiments, the operations further comprise receiving an input signal indicating to switch control to the endoscope, receiving, from the input device, a second directional input signal, and controlling movement of the endoscope based at least in part on the input signal and the second directional input signal. The first access path can comprise a natural lumen in a patient and the second access path can comprise a percutaneous access path in the patient. The cavity can comprise a cavity within a kidney.

For purposes of summarizing the disclosure, certain aspects, advantages and novel features have been described. It is to be understood that not necessarily all such advantages may be achieved in accordance with any particular embodiment. Thus, the disclosed embodiments may be carried out in a manner that achieves or optimizes one advantage or group of advantages as taught herein without necessarily achieving other advantages as may be taught or suggested herein.

BRIEF DESCRIPTION OF THE DRAWINGS

Various embodiments are depicted in the accompanying drawings for illustrative purposes and should in no way be interpreted as limiting the scope of the disclosure. In addition, various features of different disclosed embodiments can be combined to form additional embodiments, which are part of this disclosure. Throughout the drawings, reference numbers may be reused to indicate correspondence between reference elements.

FIGS. 4-1 and 4-2 illustrate driving of a catheter in a direct control mode when the catheter is facing a scope in a head on manner in accordance with one or more embodiments.

FIGS. 5-1 and 5-2 illustrate driving of a catheter in a direct control mode when the catheter and the scope are substantially facing in the same direction in accordance with one or more embodiments.

FIGS. 6-1 and 6-2 illustrate driving of a catheter in an inverted control mode when the catheter is facing a scope in a head on manner in accordance with one or more embodiments.

FIGS. 9-1 and 9-2 illustrate example implementations of driving a medical instrument from a first-person perspective for different control modes with respect to a coordinate frame for the medical instrument in accordance with one or more embodiments.

FIGS. 10-1 and 10-2 illustrate example implementations of driving a medical instrument from a third-person perspective for different control modes with respect to a coordinate frame and a control frame for the medical instrument in accordance with one or more embodiments.

FIGS. 14-1 through 14-4 illustrate an example implementation of calibrating a control frame for a medical instrument in accordance with one or more embodiments.

DETAILED DESCRIPTION

Figure 1:
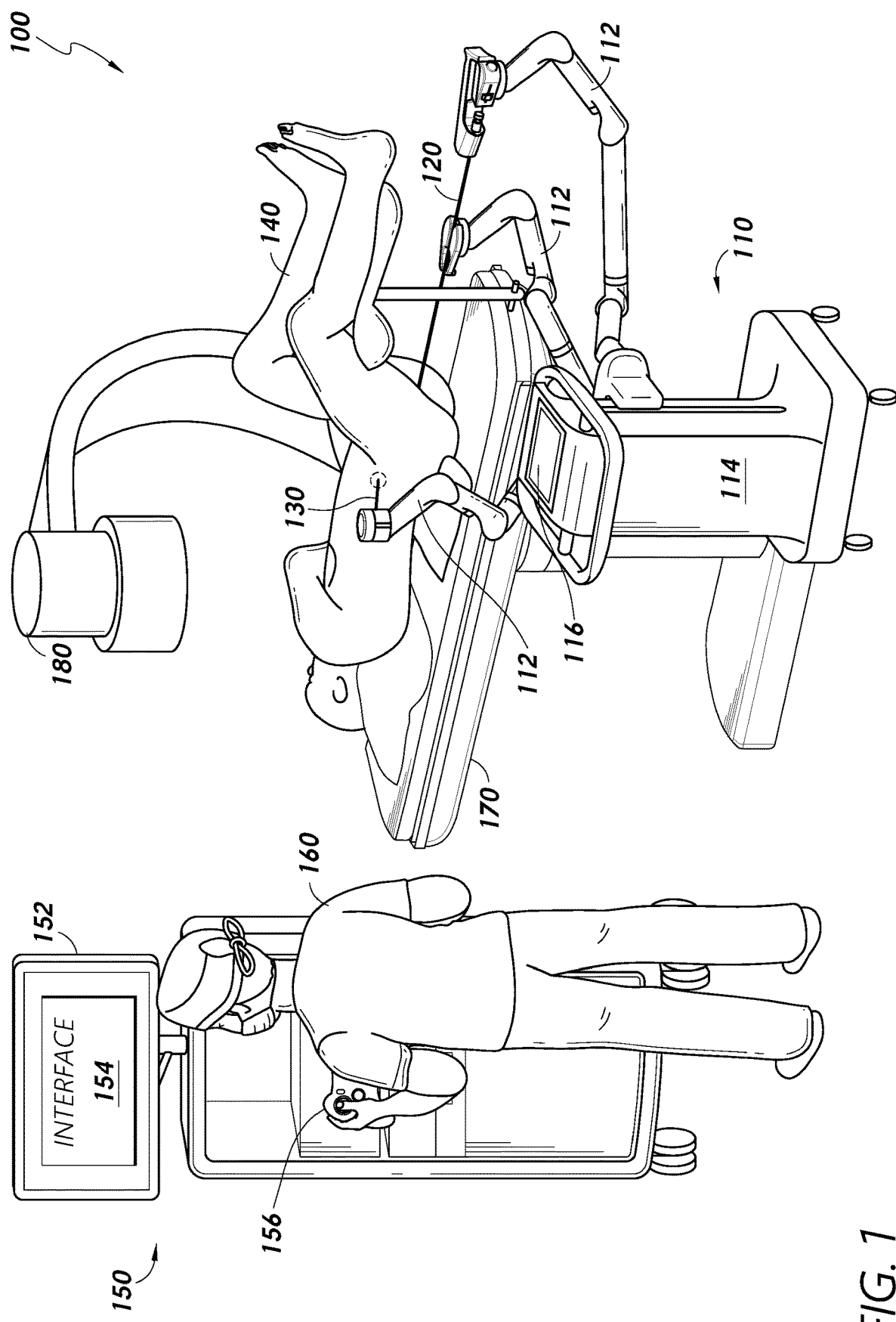
FIG. 1 illustrates an example medical system for performing various medical procedures in accordance with one or more embodiments.

The headings provided herein are for convenience only and do not necessarily affect the scope or meaning of the disclosure. Although certain preferred embodiments and examples are disclosed below, subject matter extends beyond the specifically disclosed embodiments to other alternative embodiments and/or uses and to modifications and equivalents thereof. Thus, the scope of the claims that may arise herefrom is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Certain standard anatomical terms of location are used herein to refer to the anatomy of animals, and namely humans, with respect to the preferred embodiments. Although certain spatially relative terms, such as "outer," "inner," "upper," "lower," "below," "above," "vertical," "horizontal," "top," "bottom," and similar terms, are used herein to describe a spatial relationship of one device/element or anatomical structure to another device/element or anatomical structure, it is understood that these terms are used herein for ease of description to describe the positional relationship between element(s)/structures(s), as illustrated in the drawings. It should be understood that spatially relative terms are intended to encompass different orientations of the element(s)/structures(s), in use or operation, in addition to the orientations depicted in the drawings. For example, an element/structure described as "above" another element/structure may represent a position that is below or beside such other element/structure with respect to alternate orientations of the subject patient or element/structure, and vice-versa.

Overview

The present disclosure relates to systems, devices, and methods for controlling and/or calibrating a medical instrument to aid in certain medical procedures. Although certain aspects of the present disclosure are described in detail herein in the context of renal, urological, and/or nephrological procedures, such as kidney stone removal/treatment procedures, it should be understood that such context is provided for convenience, and the concepts disclosed herein are applicable to any suitable medical procedure. However, as mentioned, description of the renal/urinary anatomy and associated medical issues and procedures is presented below to aid in the description of the concepts disclosed herein.

Kidney stone disease, also known as urolithiasis, is a relatively common medical condition that involves the formation in the urinary tract of a solid piece of material, referred to as "kidney stones," "urinary stones," "renal calculi," "renal lithiasis," or "nephrolithiasis." Urinary stones may be formed and/or found in the kidneys, the ureters, and the bladder (referred to as "bladder stones"). Such urinary stones form as a result of concentrated minerals and can cause significant abdominal pain once they reach a size sufficient to impede urine flow through the ureter or urethra. Urinary stones may be formed from calcium, magnesium, ammonia, uric acid, cysteine, and/or other compounds.

Generally, there are several methods for treating patients with kidney stones, including observation, medical treatments (such as expulsive therapy), non-invasive treatments (such as extracorporeal shock wave lithotripsy (ESWL)), and surgical treatments (such as ureteroscopy and percutaneous nephrolithotomy ("PCNL")). In surgical approaches, the physician gains access to the pathology (i.e., the object to be removed; e.g., the stone), the stone is broken into smaller pieces or fragments, and the relatively small stone fragments/particulates are extracted from the kidney.

In some cases, a physician may use a ureteroscope to remove urinary stones from the bladder and/or ureter. Typically, a ureteroscope includes an endoscope at its distal end configured to enable visualization of the urinary tract. The ureteroscope can also include a lithotomy mechanism to capture or break apart urinary stones. During a ureteroscopy procedure, a physician may insert a ureteroscope into the urinary tract through the urethra. One physician/technician may control a position of the ureteroscope, while another other physician/technician may control the lithotomy mechanism(s).

In other cases, a physician may use a percutaneous nephrolithotomy ("PCNL") technique to remove stones that are too large or resist other forms of treatment. This technique involves inserting a nephroscope through the skin (i.e., percutaneously) to break up and/or remove the stone(s). In some implementations, fluoroscopy is used during the procedure to assist in guiding the nephroscope and/or other instruments. However, fluoroscopy generally increases the cost of the nephrolithotomy procedure due to the cost of the fluoroscope itself as well as the cost of a technician to operate the fluoroscope. Fluoroscopy also exposes the patient to radiation for a relatively prolonged period of time. Even with fluoroscopy, accurately making a percutaneous incision to access the kidney stone(s) can be difficult and undesirably imprecise. Furthermore, some nephrolithotomy techniques involve a two-day or three-day inpatient stay. In sum, certain nephrolithotomy solutions can be relatively costly and problematic for patients.

According to certain medical procedures in accordance with aspects of the present disclosure, a medical system can implement multiple medical instruments to remove a urinary stone from a patient or perform another medical procedure. The medical system can include robotic tools that engage with and/or control one or more medical instruments to access the urinary stone and/or remove the stone from the patient. For example, a physician can operate the medical system to drive a scope through a natural access path in a patient to a treatment site, such as through the urethra and up to the kidney where the renal stone is located. The physician can use the scope to designate a target site for a catheter to rendezvous with the scope to assist in removing a kidney stone. The physician can operate the medical system to insert the catheter through a percutaneous access path and navigate the catheter to the treatment site where the scope is located. In some embodiments, the medical system can provide functionality to assist the physician in driving the catheter and/or the scope. For example, the medical system can enable the physician to drive the catheter from the perspective of the scope. To do so, the medical system can provide an interface with image data from a perspective of the scope (e.g., images from the scope). The image data can depict the catheter at the treatment site. The medical system can determine an orientation of the scope relative to the catheter and use such information to drive the catheter in the appropriate direction relative to the scope when input is received from a physician to move the catheter. The physician can view the movement of the catheter through the interface.

In some embodiments, the medical system can facilitate one or more control modes to assist the physician in driving the catheter from the perspective of the scope. For example, the medical system can implement an inverted control mode, where a direction of movement of the catheter is inverted (e.g., the catheter moves left relative to the catheter when right input is received, and vice versa). This may be useful in instances where the catheter is positioned more head-on relative to the scope (e.g., a tip of the catheter is facing a tip of the scope). For example, if the catheter is facing the scope and left input is received, the catheter can move left with respect to an interface used to control the catheter. Further, the medical system can implement a direct control mode, where a direction of movement of the catheter is not inverted (e.g., the catheter moves left relative to the catheter when left input is received, and moves right relative to the catheter when right input is received). This may be useful in instances where the catheter is positioned more parallel relative to the scope (e.g., a tip of the catheter and a tip of the scope are facing in substantially the same direction). For example, if the catheter and the scope are facing the same direction and left input is received, the catheter can move left with respect to an interface used to control the catheter. The medical system can select a control mode automatically, based on input form a physician, or otherwise.

Further, in some embodiments, the medical system can provide functionality to calibrate a control scheme for a medical instrument. Such calibration can be useful in instances where the medical system inaccurately tracks or is otherwise unaware of an orientation of a medical instrument, which may result in a directional error when controlling another medical instrument, such as when controlling a catheter from the perspective of a scope. For example, to calibrate a control scheme for a catheter that is controlled from the perspective of a scope, the medical system can determine an orientation of the scope relative to the catheter, such as an orientation of a distal end of the scope relative to a distal end of the catheter. In some embodiments, the medical system can provide a user interface with image data depicting the catheter from a perspective of the scope and one or more interface elements to enable a physician to specify an orientation of the catheter. Further, in some embodiments, the medical system can analyze image data and/or other sensor data from the scope and/or catheter to identify an orientation of the scope relative to the catheter. Moreover, other techniques may be used to identify an orientation of the scope relative to the catheter. In any event, the medical system can use the orientation information to adjust a control scheme associated with controlling the catheter. Such adjustment can enable the catheter to move in the appropriate direction relative to the scope when input is provided by physician.

In some implementations, the present disclosure relates to robotic-assisted medical procedures, wherein robotic tools can enable a physician to perform endoscopic and/or percutaneous access and/or treatment for a target anatomical site. For example, the robotic tools can engage with and/or control one or more medical instruments to access a target site in a patient and/or perform a treatment at the target site. In some cases, the robotic tools are guided/controlled by a physician. In other cases, the robotic tools operate in an automatic or semi-automatic manner. Although many techniques are discussed in the context of robotic-assisted medical procedures, the techniques may be applicable to other types of medical procedures, such as procedures that do not implement robotic tools or implement robotic tools for relatively few operations (e.g., less than a threshold number).

In several of the examples described herein, object removal procedures relate to removal of kidney stones from a kidney. This disclosure, however, is not limited only to kidney stone removal. For example, the following description is also applicable to other surgical/medical operations or medical procedures concerned with the removal of objects from a patient, including any object that can be removed from a treatment site or patient cavity (e.g., the esophagus, ureter, intestine, eye, etc.) via percutaneous and/or endoscopic access, such as, for example, gallbladder stone removal, lung (pulmonary/transthoracic) tumor biopsy, or cataract removal.

Medical System

FIG. 1 illustrates an example medical system 100 for performing various medical procedures in accordance with aspects of the present disclosure. The medical system 100 includes a robotic system 110 configured to engage with and/or control a medical instrument 120, a medical instrument 130, and/or another medical instrument to perform a procedure on a patient 140. The medical system 100 also includes a control system 150 configured to interface with the robotic system 110, provide information regarding the procedure, and/or perform a variety of other operations. For example, the control system 150 can include a display(s) 152 to present certain information to assist a physician 160. The medical system 100 can include a table 170 configured to hold the patient 140. In some embodiments, the medical system 100 can also include an imaging device 180 which can be integrated into a C-arm and/or configured to provide imaging during a procedure, such as for a fluoroscopy-type procedure. Various acts are described herein as being performed by the physician 160. It should be understood that these acts can be performed directly by the physician 160, a user under the direction of the physician 160, another user (e.g., a technician), a combination thereof, and/or any other user.

In the example of FIG. 1, the medical instrument 120 is implemented as a scope and the medical instrument 130 is implemented as a catheter. Thus, for ease of discussion, the medical instrument 120 is referred to as "the scope 120" or "the direct access/entry instrument 120," and the medical instrument 130 is referred to as "the catheter 130" or "the percutaneous access/entry instrument 130." However, the medical instrument 120 and the medical instrument 130 can each be implemented as any type of medical instrument including, for example, a scope (sometimes referred to as an "endoscope"), a catheter, a needle, a guidewire, a lithotripter, a basket retrieval device, forceps, a vacuum, a needle, a scalpel, an imaging probe, jaws, scissors, graspers, needle holder, micro dissector, staple applier, tacker, suction/irrigation tool, clip applier, and so on. In some embodiments, a medical instrument is a steerable device, while in other embodiments a medical instrument is a non-steerable device. In some embodiments, a surgical tool refers to a device that is configured to puncture or to be inserted through the human anatomy, such as a needle, a scalpel, a guidewire, and so on. However, a surgical tool can refer to other types of medical instruments.

The term "scope" or "endoscope" are used herein according to their broad and ordinary meanings and can refer to any type of elongate medical instrument having image generating, viewing, and/or capturing functionality and configured to be introduced into any type of organ, cavity, lumen, chamber, and/or space of a body. For example, references herein to scopes or endoscopes can refer to a ureteroscope (e.g., for accessing the urinary tract), a laparoscope, a nephroscope (e.g., for accessing the kidneys), a bronchoscope (e.g., for accessing an airway, such as the bronchus), a colonoscope (e.g., for accessing the colon), an arthroscope (e.g., for accessing a joint), a cystoscope (e.g., for accessing the bladder), a borescope, and so on. Scopes/endoscopes, in some instances, may comprise a rigid or flexible tube, and may be dimensioned to be passed within an outer sheath, catheter, introducer, or other lumen-type device, or may be used without such devices.

The terms "direct entry" or "direct access" are used herein according to their broad and ordinary meaning and may refer to any entry of instrumentation through a natural or artificial opening in a patient's body. For example, with reference to FIG. 1, and as noted above, the scope 120 may be referred to as a direct access instrument, since the scope 120 enters into the urinary tract of the patient 140 via the urethra.

The terms "percutaneous entry" or "percutaneous access" are used herein according to their broad and ordinary meaning and may refer to entry, such as by puncture and/or minor incision, of instrumentation through the skin of a patient and any other body layers necessary to reach a target anatomical location associated with a procedure (e.g., the calyx network of the kidney). As such, a percutaneous access instrument may refer to a medical instrument, device, or assembly that is configured to puncture or to be inserted through skin and/or other tissue/anatomy, such as a needle, scalpel, guidewire, sheath, shaft, scope, catheter, and the like. However, it should be understood that a percutaneous access instrument can refer to other types of medical instruments in the context of the present disclosure. In some embodiments, a percutaneous access instrument refers to an instrument/device that is inserted or implemented with a device that facilitates a puncture and/or minor incision through the skin of a patient. For example, the catheter 130 may be referred to as a percutaneous access instrument when the catheter 130 is inserted through a sheath/shaft that has punctured the skin of the patient 140.

In some embodiments, a medical instrument, such as the scope 120 and/or the catheter 130, includes a sensor (sometimes referred to as a position sensor) that is configured to generate sensor data. In examples, sensor data can indicate a position and/or orientation of the medical instrument and/or can be used to determine a position and/or orientation of the medical instrument. For instance, sensor data can indicate a position and/or orientation of a scope, which can include a roll of a distal end of the scope. A position and orientation of a medical instrument can be referred to as a pose of the medical instrument. A sensor can be positioned on a distal end of a medical instrument and/or any other location. In some embodiments, a sensor can provide sensor data to the control system 150 and/or another system/device to perform one or more localization techniques to determine/track a position and/or an orientation of a medical instrument.

In some embodiments, a sensor can include an electromagnetic (EM) sensor with a coil of conductive material. Here, an EM field generator can provide an EM field that is detected by the EM sensor on the medical instrument. The magnetic field can induce small currents in coils of the EM sensor, which can be analyzed to determine a distance and/or angle/orientation between the EM sensor and the EM field generator. Further, a sensor can include another type of sensor, such as a camera, a range sensor, a radar device, a shape sensing fiber, an accelerometer, a gyroscope, an accelerometer, a satellite-based positioning sensor (e.g., a global positioning system (GPS)), a radio-frequency transceiver, and so on.

A medical instrument can be associated with a coordinate frame, which can include a set of two or more vectors (or axes) that make a right angle with one another. For example, in a three-dimensional space, a coordinate frame can include three vectors (e.g., x-vector, y-vector, and z-vector) that make right angles with each other. Although various conventions can be used, for ease of illustration the description herein will often refer to the "forward" direction (e.g., insert/retract) as corresponding to positive z, the "right" direction as corresponding to positive x, and the "up" direction as corresponding to positive y. The z-vector can extend along a longitudinal axis of a medical instrument. Such coordinate system can be referred to as a "left-handed coordinate system." However, the disclosure herein can similarly be discussed/implemented in the context of a right-handed coordinate system. In examples, a coordinate frame is set/correlated based on a position of one or more elongate movement members of a medical device (e.g., one or more pull wires). Further, in examples, a coordinate frame is set/correlated to/based on a position of an image device on a medical instrument, such as a distal end of an image device on a tip of a scope. As such, a coordinate frame may correspond to a camera frame of reference. However, a coordinate frame can be correlated/set at other locations. In many examples, a coordinate frame for a medical instrument will be represented/discussed with respect to a distal end of a medical instrument (e.g., an end at a treatment site). However, a coordinate frame can be positioned elsewhere.

As noted above, the control system 150 can be configured to provide various functionality to assist in performing a medical procedure. In some embodiments, the control system 150 can be coupled to the robotic system 110 and operate in cooperation with the robotic system 110 to perform a medical procedure on the patient 140. For example, the control system 150 can communicate with the robotic system 110 via a wireless or wired connection to control the scope 120 and/or the catheter 130 connected to the robotic system 110, receive an image(s) captured by the scope 120, and so on. Additionally, or alternatively, the control system 150 can provide fluids to the robotic system 110 via one or more fluid channels, provide power to the robotic system 110 via one or more electrical connections, provide optics to the robotic system 110 via one or more optical fibers or other components, and so on. In some embodiments, the control system 150 can communicate with the scope 120 (and/or the catheter 130) to receive sensor data (via the robotic system 110 and/or directly from the scope 120 and/or the catheter 130). In examples, sensor data can indicate or be used to determine a position and/or orientation of a medical instrument. Moreover, in some embodiments, the control system 150 can communicate with the table 170 to position the table 170 in a particular orientation or otherwise control the table 170. Further, in some embodiments, the control system 150 can communicate with an EM field generator to control generation of an EM field around the patient 140.

The control system 150 includes various I/O devices configured to assist the physician 160 or others in performing a medical procedure. In the example of FIG. 1, the control system 150 includes an I/O device(s) 156 that is employed by the physician 160 or other user to navigate or otherwise control a medical instrument. For example, the physician 160 can provide input via the I/O device(s) 156 and, in response, the control system 150 can send control signals to the robotic system 110 to manipulate the scope 120/the catheter 130. In examples, the physician 160 can use the same I/O device to control the scope 120 and/or the catheter 130 (e.g., switch control between the devices). In some embodiments, the scope 120 is driven from a first-person perspective (e.g., from the viewpoint of the scope 120) and/or the catheter 130 is driven from a third-person perspective (e.g., from the viewpoint of the scope 120), as discussed in further detail below. Although the I/O device(s) 156 is illustrated as a controller in the example of FIG. 1, the I/O device(s) 156 can be implemented as a variety of types of I/O devices, such as a touchscreen, a touch pad, a mouse, a keyboard, etc.

As also shown in FIG. 1, the control system 150 can include a display(s) 152 to provide various information related to a procedure. For example, the control system 150 can receive real-time images that are captured by the scope 120 and display the real-time images and/or visual representations of the real-time images via the display(s) 152. The display(s) 152 can present an interface(s) 154, such as any of the interfaces discussed herein, which can include image data from the scope 120 and/or another medical instrument.

In some embodiments, the control system 150 can provide image data via the interface(s) 154 in a manner that maintains a constant orientation of the image data (sometimes referred to as an "original image view"). For example, the interface(s) 154 can maintain a constant relationship with a coordinate frame for the scope 120 (e.g., so that up in the interface(s) 154 corresponds to the positive y-vector of the coordinate frame for the scope 120). To illustrate, assume that a kidney stone depicted in image data from the scope 120 initially shows up on the left side in the interface(s) 154. If the scope rolls 180 degrees, the kidney stone will move within the interface(s) 154 during the roll and appear on the right side in the interface(s) 154 after the roll. Here, the control system will not adjust the orientation of the image data displayed through the interface(s) 154. As such, the horizon in the image data can be perceived as rolling.

In other embodiments, the control system 150 can provide image data via the interface(s) 154 in a manner that updates an orientation of the image data (sometimes referred to as a "rotated image or virtual view"). For example, the interface(s) 154 can update a relationship with a coordinate frame for the scope 120 (e.g., so that up in the interface(s) 154 does not always correspond to the positive y-vector of the coordinate frame for the scope 120). To illustrate, assume that a kidney stone depicted in image data from the scope 120 initially shows up on the left side in the interface(s) 154. If the scope rolls 180 degrees, the kidney stone will still show up on the left side in the interface(s) 154 after the roll. Here, the control system 150 can adjust the orientation of the image data displayed via the interface(s) 154 as the scope 120 rolls 180 degrees to maintain objects depicted in the image data in the same orientation (e.g., roll correct the image data). As such, the horizon in the image data can be perceived as staying the same.

Additionally, or alternatively, the control system 150 can output other information via the display(s) 152. For example, the control system 150 can receive signals (e.g., analog, digital, electrical, acoustic/sonic, pneumatic, tactile, hydraulic, etc.) from a medical monitor and/or a sensor associated with the patient 140, and the display(s) 152 can present information regarding the health or environment of the patient 140. Such information can include information that is displayed via a medical monitor including, for example, a heart rate (e.g., ECG, HRV, etc.), blood pressure/rate, muscle bio-signals (e.g., EMG), body temperature, blood oxygen saturation (e.g., $SpO_2$), $CO_2$, brainwaves (e.g., EEG), environmental and/or local or core body temperature, and so on.

To facilitate the functionality of the control system 150, the control system 150 can include various components (sometimes referred to as "subsystems"). For example, the control system 150 can include control electronics/circuitry, as well as one or more power sources, pneumatics, optical sources, actuators, memory/data storage devices, and/or communication interfaces. In some embodiments, the control system 150 includes control circuitry comprising a computer-based control system that is configured to store executable instructions, that when executed, cause various operations to be implemented. In some embodiments, the control system 150 is movable, such as that shown in FIG. 1, while in other embodiments the control system 150 is a stationary system. Although various functionality and components are discussed as being implemented by the control system 150, any of this functionality and/or components can be integrated into and/or performed by other systems and/or devices, such as the robotic system 110, the table 170, or even the scope 120 and/or the catheter 130.

The robotic system 110 can be arranged in a variety of ways depending on the particular procedure. The robotic system 110 can include the one or more robotic arms 112 configured to engage with and/or control a medical instrument(s) to perform a procedure. As shown, each robotic arm 112 can include multiple arm segments coupled to joints, which can provide multiple degrees of movement. In the example of FIG. 1, two of the robotic arms 112 are actuated to engage with the scope 120 to access a target site through the urethra of the patient 140, and one of the robotic arms 112 is actuated to engage with the catheter 130 to access the target site through a percutaneous access path. When the robotic system 110 is properly positioned, the scope 120 and/or the catheter 130 can be inserted and/or navigated into the patient 140 robotically using the robotic arms 112, manually by the physician 160, or a combination thereof. Although not illustrated in FIG. 1, the robotic arms 112 can also be connected to other medical instruments, which may be interchanged during a procedure, such as an electromagnetic (EM) field generator that may be positioned near a treatment site during a particular phase of a procedure. Further, although the robotic arms 112 are shown in various positions and coupled to various instrumentation, it should be understood that such configurations are shown for convenience and illustration purposes, and such robotic arms 112 may have different configurations over time during a medical procedure.

The robotic system 110 can also include a support structure 114 coupled to the one or more robotic arms 112. The support structure 114 can include control electronics/circuitry, one or more power sources, one or more pneumatics, one or more optical sources, one or more actuators (e.g., motors to move the one or more robotic arms 112), memory/data storage, and/or one or more communication interfaces. In some embodiments, the support structure 114 includes an input/output (I/O) device(s) 116 configured to receive input, such as user input to control the robotic system 110, and/or provide output, such as a graphical user interface (GUI), information regarding the robotic system 110, information regarding a procedure, and so on. The I/O device(s) 116 can include a display, a touchscreen, a touchpad, a projector, a mouse, a keyboard, a microphone, a speaker, etc. In some embodiments, the robotic system 110 is movable (e.g., the support structure 114 includes wheels) so that the robotic system 110 can be positioned in a location that is appropriate or desired for a procedure. In other embodiments, the robotic system 110 is a stationary system. Further, in some embodiments, the robotic system 112 is integrated into the table 170.

The robotic system 110 can be coupled to any component of the medical system 100, such as the control system 150, the table 170, the scope 120, the catheter 130, and/or other devices/instruments. In one example, the robotic system 110 is communicatively coupled to the control system 150 to receive a control signal from the control system 150 to perform an operation, such as to position a robotic arm 112 in a particular manner, manipulate the scope 120 and/or the catheter 130, and so on. In another example, the robotic system 110 is configured to receive an image from the scope 120 depicting internal anatomy of the patient 140 and/or send the image to the control system 150, which can then be displayed on the display(s) 152. Furthermore, in some embodiments, the robotic system 110 is coupled to a component of the medical system 100, such as the control system 150, in such a manner as to allow for fluids, optics, power, or the like to be received therefrom.

The imaging device 180 can be configured to capture/generate one or more images of the patient 140 during a procedure, such as one or more x-ray or CT images. In examples, images from the imaging device 180 can be provided in real-time to view anatomy and/or medical instruments, such as the scope 120 and/or the catheter 130, within the patient 140 to assist the physician 160 in performing a procedure. The imaging device 180 can be used to perform a fluoroscopy (e.g., with a contrast dye within the patient 140) or another type of imaging technique. Although shown in FIG. 1, in embodiments the imaging device 180 is not implemented for performing a procedure and/or the imaging device 180 (including the C-arm) is eliminated.

The various components of the medical system 100 can be communicatively coupled to each other over a network, which can include a wireless and/or wired network. Example networks include one or more personal area networks (PANs), local area networks (LANs), wide area networks (WANs), Internet area networks (IANs), cellular networks, the Internet, etc. Further, in some embodiments, the components of the medical system 100 are connected for data communication, fluid/gas exchange, power exchange, and so on, via one or more support cables, tubes, or the like.

As noted above, the medical system 100 can enable the physician 160 to drive a medical instrument, such as to navigate the medical instrument within the patient 140. For example, the control system 150 can receive an input signal from the I/O device(s) 156 indicative of a direction of movement for a medical instrument. The control system 150 can determine an orientation/position of the medical instrument, an orientation/position of another medical instrument providing image data of the medical instrument (in some cases), and/or an orientation of image data displayed through the interface(s) 154. The control system 150 can use such information to generate a control signal to move the medical instrument in the appropriate direction relative to a coordinate/control frame of the medical instrument. The control system 150 can send the control signal to the robotic system 110 to manipulate the medical instrument.

In some embodiments, the medical system 100 enables the physician 160 to drive a medical instrument from a perspective of the medical instrument (also referred to as "first-person driving"). This type of driving may be useful in situations where a medical instrument includes an imaging device to provide image data and/or in other situations. For example, the control system 150 can enable the scope 120 to be driven from a perspective of the scope 120. The scope 120 can include an imaging device configured to provide image data to the control system 150. The control system 150 can display the image data through the interface(s) 154 to assist the physician 160 in driving the scope 120 from the perspective of the scope 120.

In the case of first-person driving, the control system 150 can generally control a medical instrument to move in a correlated manner to an orientation of image data from the medical instrument displayed via the interface(s) 154. For example, assume that the physician 160 is driving the scope 120 from the perspective of the scope 120 and the physician 160 provides input via the I/O device(s) 156 to move the scope 120 in an upward direction relative to the I/O device(s) 156, such as by selecting an up control on the I/O device(s) 156. The control system 150 can determine an orientation/position of the scope 120 and/or an orientation of image data from the scope 120 that is displayed via the interface(s) 154. The control system 150 can use such orientation/position information to move the scope 120 in the appropriate direction that shows up as an upward direction on the interface(s) 154.

To illustrate, if the interface(s) 154 is displaying a static view for the scope 120 (e.g., up in the interface(s) 154 corresponds to the positive y-vector of the coordinate frame for the scope 120), the control system 150 can cause the scope 120 to move along the positive y-vector of the coordinate frame for the scope 120 in response to up input on the I/O device(s) 156. Further, if the interface(s) 154 is displaying a rotated image view for the scope 120 (e.g., up in the interface(s) 154 does not always correspond to the positive y-vector of the coordinate frame for the scope 120), the control system 150 can determine an offset of a frame of reference of the image data to the coordinate frame for the scope 120 to cause the scope 120 to move in the appropriate direction that appears as the scope 120 moving upward in the interface(s) 154.

Further, in some embodiments, the medical system 100 can enable the physician 160 to drive a medical instrument from a perspective of another medical instrument (also referred to as "third-person driving"). This type of driving may be useful in situations where medical instruments rendezvous with each other and/or one of the medical instruments does not include an imaging device. For example, the control system 150 can enable the physician 160 to drive the catheter 130 from the perspective of the scope 120, which may be useful in cases where the catheter 130 does not include an imaging device. Here, the scope 120 can provide image data and the control system 150 can display the image data through the interface(s) 154. When the catheter 130 is within a field-of-view of the scope 120, the physician 160 can view the catheter 130 in the interface(s) 154 and drive the catheter 130 from the perspective of the scope 120.

In the case of third-person driving, the control system 150 can generally implement a control scheme to control movement of a medical instrument. For example, assume that the physician 160 is driving the catheter 130 from the perspective of the scope 120 and the physician 160 provides input via the I/O device(s) 156 to move the catheter 130 in an upward direction relative to the I/O device(s) 156, such as by selecting an up control on the I/O device(s) 156. The control system 150 can implement a control scheme for the catheter 130 that accounts for an orientation of the scope 120 relative to the catheter 130. This can enable the catheter 130 to move in the appropriate direction that shows up as an upward direction on the interface(s) 154.

A control scheme can be used to map input control to control signals to move of a medical instrument. In some embodiments, a control scheme includes a control frame (sometimes referred to as a "control frame of reference"), which can include an abstract coordinate frame/set of vectors that is used to control a medical instrument/device. For example, a control frame can include a set of two or more vectors (or axes) that make right angles with one another. A control frame can generally be correlated to a coordinate frame for a medical instrument. For example, a control frame for a medical instrument can be offset with respect to a coordinate frame for the medical instrument (e.g., 30-degree offset about an axis/vector). In examples, a coordinate frame remains static for a medical instrument (i.e., fixed to a point on the medical instrument), while a control frame can be dynamically updated, such as based on roll of the medical instrument, an orientation of image data via a user interface, and the like. In examples, a control frame is correlated to a tip of a medical instrument. However, a control frame can be correlated/centered at other locations.

In some embodiments, a control scheme/frame is determined based on an orientation of image data displayed through an interface. For example, vertical/horizontal axes of the control frame can be correlated/aligned with vertical/horizontal axes of image data within an interface. To illustrate, in the case of driving the catheter 130 the perspective of the scope 120, a control frame for the catheter 130 can be correlated to an orientation of image data from the scope 120 as displayed via the interface(s) 154. Example control frames are discussed in further detail below. Although a control frame is often discussed in the context of third-person driving, a control frame can be used in other context, such as in the case of first-person driving, and so on.

In some situations of third-person driving, it may be challenging for the physician 160 to drive a medical instrument. For example, if the physician 160 is driving the catheter 130 from the perspective of the scope 120 and the catheter 130 is facing the scope 120 in a substantially head on manner (e.g., a tip of the catheter 130 is facing a tip of the scope 120), the physician 160 must provide inverted left and right input to move the catheter 130 in the appropriate direction relative to the interface(s) 154. For instance, if the physician 160 desires to move the catheter 130 to the left with respect to the interface(s) 154, the physician 160 may be required to provide right input via the I/O device(s) 156, and vice versa. In contrast, when the catheter 130 and the scope 120 are facing in substantially the same direction (e.g., a tip of the catheter 130 and a tip of the scope 120 are facing the same direction), no such inverted input is required. In sum, certain situations of third-person driving can make it difficult for the physician 160 to drive a medical instrument, which can result in harm the patient 140 (e.g., when the medical instrument is moved in an undesired direction), lead to inefficient procedures, and so on.

As such, the medical system 100 can facilitate one or more control/driving modes to assist the physician 160 in driving a medical instrument. By using multiple control modes, a medical instrument can be driven in an effective manner for different orientations of the medical instruments relative to each other. For example, if the catheter 130 as being driven from the perspective of the scope 120, the physician 160 may be able to view the catheter 130 as moving in a direction on the interface(s) 154 that more intuitively corresponds to input provided via the I/O device(s) 156. In some examples, the medical system 100 can switch to a different control mode by reconfiguring the control system 150 (e.g., to process an input signal from the I/O device(s) 156 and/or to generate a control signal for the robotic system 110 in a different manner), reconfiguring the I/O device(s) 156 (e.g., to send a different input control signal), and/or reconfiguring the robotic system 110 (e.g., to control a robotic arm in a different manner). Although multiple control modes are often discussed in the context of third-person driving, such control modes can be used in other contexts, such as first-person driving or any other driving scenario.

In some embodiments, the control system 150 can implement a direct control mode (also referred to as a "parallel mode") to drive a medical instrument in a corresponding manner with respect to a coordinate/control frame of the medical instrument. For example, when driving the catheter 130 from the perspective of the scope 120 in the direct control mode, if the physician 160 selects left input on the I/O device(s) 156, the control system 150 can control the catheter 130 to move left with respect to the catheter 130. If the catheter 130 is facing in substantially the same direction as the scope 120, the physician 160 may view the catheter 130 as moving to the left in the interface(s) 154 (e.g., from the third-person point-of-view). In contrast, if the catheter 130 is facing the scope 120 in a head on manner, the physician 160 may view the catheter 130 as moving to the right in the interface(s) 154. Thus, the direct control mode may often be implemented when the catheter 130 and the scope 120 are substantially facing in the same direction.

Additionally, or alternatively, the control system 150 can implement an inverted control mode (also referred to as a "mirrored mode") to drive a medical instrument in an inverted manner with respect to a coordinate/control frame of the medical instrument. For example, when driving the catheter 130 from the perspective of the scope 120 in the inverted control mode, if the physician 160 selects left input on the I/O device(s) 156, the control system 150 can control the catheter 130 to move right with respect to the catheter 130. If the catheter 130 is facing the scope 120 in a head on manner, the physician 160 may view the catheter 130 as moving to the left in the interface(s) 154 (e.g., from the third-person point-of-view). In contrast, if the catheter 130 is facing in substantially the same direction as the scope 120, the physician 160 may view the catheter 130 as moving to the right in the interface(s) 154. Thus, the direct control mode may often be implemented when the catheter 130 and the scope 120 are substantially facing each other in a head on manner.

In some embodiments, the inverted control mode is associated with inverting horizontal movement for a medical instrument and not vertical movement. For example, in the inverted control mode, the control system 150 can cause a horizontal component for a coordinate/control frame to be inverted and not a vertical component(s) (e.g., invert a sign of an x value and not a y value). However, vertical directions can also be inverted in some cases of the inverted control mode.

Further, in some embodiments, a control mode can indicate whether or not to invert retraction and insertion. For example, in the direct control mode, a forward input control on the I/O device(s) 156 can be associated with inserting the catheter 130 farther into the patient 140 and a reverse input control on the I/O device(s) 156 can be associated with retracting the catheter 130 from the patient 140. If the catheter 130 is being driven from the perspective of the scope 120 and the instruments are facing each other in a head on manner, the physician 160 may view the catheter 130 as moving closer to the scope 120 for forward input and as moving away from the scope 120 for reverse input. Further, in the inverted control mode, the forward input control can be associated with retracting the catheter 130 and the reverse input control can be associated with inserting the catheter 130. If the catheter 130 is being driven from the perspective of the scope 120 and the instruments are facing each other in a head on manner, the physician 160 may view the catheter 130 as moving away from the scope 120 for forward input and as moving closer to the scope 120 for reverse input.

A control mode can be selected in a variety of manners. In some embodiments, the physician 160 can provide input to select a control mode, such as through the interface(s) 154, the I/O device(s) 156, or otherwise. This may allow the physician 160 to configure the medical system 100 to a preference of the physician 160. Further, in some embodiments, the control system 150 can automatically select a control mode that is appropriate for a particular situation. For example, the control system 150 can perform one or more localization techniques to determine and/or track a position and/or an orientation of a medical instrument and/or another object, as discussed in further detail below in reference to FIG. 20. In some cases, the control system 150 can automatically select an inverted control mode when the catheter 130 and the scope 120 are facing each other in a head on manner and/or a direct control mode when the catheter 130 and the scope 120 are facing in substantially the same direction.

In some embodiments, the medical system 100 can learn to automatically select a particular control mode. For example, if a specific physician selects an inverted control mode more than a threshold number of times when the scope 120 is oriented in a head on manner with respect to the catheter 130 (e.g., oriented at an angle relative to each other), the medical system 100 can learn to automatically select the inverted control mode whenever the scope 120 and the catheter 130 are oriented in a similar manner in the future and/or when the specific physician is logged in to the medical system 100. The medical system 100 can use a variety of parameters to learn when to select a particular control mode, such as a type of procedure being performed, a type of medical instrument being implemented, and so on. As such, the medical system 100 can automatically select a control mode for a particular situation.

Further, in some embodiments, the medical system 100 can implement other techniques to drive a medical instrument, instead of or in addition to implementing a control mode(s). In one example, the catheter 130 can include an imaging device and the interface(s) 154 can provide image data from the catheter 130 to drive the catheter 130 from a first-person perspective. In another example, a tip of the catheter 130 can include one or more markings and the I/O device(s) 156 can include the same one or more markings to indicate a mapping of an input control to a direction of movement of the catheter 130. To illustrate, the tip of the catheter 130 can include a red marking on one side of the tip (e.g., half of the tip) and a blue marking on the other side of the tip (e.g., the other half of the tip). Here, the I/O device(s) 156 can include a right input control that has a red marking that, when selected, causes the catheter 130 to move in the direction of the red marking on the tip of the catheter 130. Further, the I/O device 156 can include a left input control that has a blue marking that, when selected, causes the catheter 130 to move in the direction of the blue marking on the tip of the catheter 130. As such, the physician 160 can look at the markings on the I/O device(s) 156 to determine an input control to select.

In some embodiments, the medical system 100 can provide functionality to calibrate a control scheme for a medical instrument. Such calibration techniques may be useful in instances where the medical system is unaware or inaccurately determines an orientation/position of a medical instrument. For example, the medical system 100 may not know the amount of roll associated with the scope 120 when the scope 120 is mounted on an arm 112 of the robotic system 110. In some cases, the scope 120 includes a lockout position associated with a particular roll of the scope 120. The lockout may be associated with a mechanism on the scope 120 and/or a mechanism on the mounting component of the arm 112 (e.g., a pin, slot to receive the pin, etc.). When placed in the lockout position, the scope 120 is unable to roll, until placed on the mounting component of the arm 112 (which releases the lockout). If the scope 120 is mounted on the robotic system 110, the medical system 100 may generally assume that the scope 120 is in a lockout position (e.g., at zero roll). However, if the scope 120 is removed from the robotic system 110 in a non-lockout position and/or is manually rolled when located off of the robotic system 110 to an arbitrary roll position, and then subsequently remounted on the robotic system 100, the medical system 100 may incorrectly assume the amount of roll of the scope 120 (e.g., incorrectly assume that the scope 120 is in a lockout position).

Further, the medical system 100 may lose track of an amount of roll associated with the scope 120 during a procedure. For example, friction or other forces can be applied to the scope 120 during a procedure due to the scope 120 being placed within various anatomy of a patient. Such forces can prevent manipulation of a proximal end the scope 120 from fully propagating to a distal end of the scope 120, resulting in an undetected amount of roll at a tip of the scope 120. For example, if the robotic system 110 manipulates a robotic arm connected to the scope 120 to roll the scope 80 degrees, the tip of the scope 120 may roll by only 60 degrees, even though the control system 150 may track the scope 120 as having rolled 80 degrees. Moreover, during certain phases of a procedure, an EM field generator can be implemented to track a position/orientation of a medical instrument. However, during other phases, the EM field generator may need to be removed, such as to mount a catheter 130 or other instrument on a same arm (as discussed in further detail below). Without the EM field generator, it may be difficult to track the position/orientation of the medical instrument. Furthermore, the scope 120 may experience parasitic roll called "curve alignment" that causes the distal end of the scope 120 to rotate undesirably.

Such unaccounted roll of a medical instrument, such as the scope 120, can result in a clocking/roll error, which can make it difficult to control the scope 120 or another medical instrument. For example, if the scope 120 is estimated to have a particular amount of roll, and such estimation is inaccurate, the medical system 100 may inaccurately drive the scope 120 and/or the catheter 130 from the perspective of the scope 120 (e.g., the scope 120/catheter 130 may move in the wrong direction relative to the interface(s) 154).

To address situations of roll error, the medical system 100 can implement one or more calibration techniques to update orientation/position information associated with a medical instrument(s). For example, the medical system 100 can determine an orientation of a distal end of the scope 120 relative to an orientation of a distal end of the catheter 130 and use such information to adjust a control scheme associated with controlling the catheter 130 from a perspective of the scope 120. For example, if the medical system 100 determines that an estimated orientation of the scope 120 relative to the catheter 130 is off by 30 degrees from the actual orientation of the scope 120 relative to the catheter 130, the medical system 100 can adjust a control frame by 30 degrees or based on a 30-degree offset.

In some embodiments, the control system 150 can provide information via the interface(s) 154 to enable the physician 160 to calibrate an orientation of a medical instrument. For example, the control system 150 can display image data captured by the scope 120, which may depict the catheter 130. The control system 150 can also display an alignment indicator representing an orientation of the catheter 130 relative to the scope 120 (e.g., an estimated orientation of a coordinate frame of the catheter 130 relative to a coordinate frame of the scope 130). In some embodiments, the catheter 130 can include one or more markings, such as on a distal end of the catheter 130, and the alignment indicator can represent an orientation of the one or more markings on the catheter 130. If the alignment indicator is not aligned in the interface(s) 154 with the one or more markings on the catheter 130 as depicted in the image data, the physician 160 can adjust the alignment indicator to the appropriate orientation to indicate the actual orientation of the tip of the catheter 130 relative to the tip of the scope 120. Based on the orientation indicated by the physician 160, the control system 150 can update a control scheme used to control the catheter 130, if needed, such as by updating one or more parameters associated with a control frame (e.g., orientation of one or more vectors).

Further, in some embodiments, the control system 150 can perform one or more image processing techniques to calibrate an orientation of a medical instrument. For example, the control system 150 can process image data captured by the scope 120, which depicts the catheter 130, to identify an orientation of the catheter 130 relative to the scope 120 (e.g., a coordinate frame of the catheter 130 relative to a coordinate frame of the scope 130). Such processing can identify one or more markings on a tip of the catheter 130 (if included), an amount of bending or bending direction of the catheter 130, and/or other features of the catheter 130. Based on the orientation identified by the image processing, the control system 150 can update a control scheme for the catheter 130, if needed.

Moreover, in some embodiments, the control system 150 can instruct the physician 160 to perform a particular action. In one example, the control system 150 instructs the physician 160 to select a particular directional control on the I/O device(s) 156 (e.g., select the up input control). In response to the physician 160 selecting the particular directional control, the control system 150 can control the catheter 130 to move, which may be in any direction depending on an accuracy of a control frame/scheme associated with the catheter 130. The control system 150 can then receive further input from the physician 160 indicating a direction in which the catheter 130 moved with respect to the interface(s) 154. Based on any difference between the direction indicated by the physician 160 in which the catheter 130 moved (with respect to a control/coordinate frame) and the direction in which the control system 150 estimated that the catheter 130 moved (with respect to the control/coordinate frame), the control system 150 can update the control frame/scheme for the catheter, if needed. In another example, the control system 150 can instruct the physician 160 to move the catheter 130 in a particular direction with respect to the interface(s) 154 (e.g., text of "move the catheter to the right," a right arrow, etc. can be displayed via the interface(s) 154). The physician 160 can provide input control via the I/O device(s) 156 to move the catheter 130 in the particular direction with respect to the interface(s) 154, which may take multiple attempts. Upon successfully moving the catheter 130 in the particular direction, the physician 160 can provide additional input indicating that such instruction was completed. Based on the input control provided when the catheter 130 successfully moved in the particular direction on the interface(s) 154, the direction in which the catheter 130 moved with respect to a control/coordinate frame for the successful movement, and/or the direction in which the control system 150 estimated that the catheter 130 moved (with respect to the control/coordinate frame), the control system 150 can update the control frame/scheme for the catheter, if needed.

Although many embodiments are discussed in the context of calibrating a control scheme associated with third-person driving, the calibration techniques can be implemented in the context of first-person driving and/or any other scenario. Further, although many embodiments are discussed in the context of calibrating a control scheme for a catheter, the calibration techniques can additionally, or alternatively, be implemented to calibrate a control scheme for a scope and/or another medical instrument. For example, the catheter 130 may be associated with roll functionality in some cases and such calibration techniques can be implemented to correct roll error of the catheter 130.

In some embodiments, the calibration techniques can be implemented as part of troubleshooting functionality, such as when the physician 160 notices that a medical instrument is not moving in a manner that correlates to input provided to control the medical instrument. Here, the physician 160 can enter a calibration interface. However, the calibration techniques can be implemented automatically, periodically, or any time and/or based on a variety of events.

In some embodiments, the catheter 130 includes or is associated with certain characteristics that assist in using the catheter 130 as a reference point for calibration. For example, the catheter 130 may not be able to roll, which can avoid any potential roll error. Further, the catheter 130 can be inserted along a path that is substantially straight, in comparison to a path along which the scope 120 proceeds. This can minimize propagation error at a distal end of the catheter 130, in comparison to the scope 120. Moreover, in some examples, the catheter 130 may be relatively short, in comparison to the scope 120. Such characteristics of the catheter 130 can enable a position/orientation of the catheter 130 to be accurately determined/tracked, such as based on an orientation/position of a robotic arm 112 attached to the catheter 130 (e.g., the position/orientation of the catheter 130 can be offset from a plane in which the catheter 130 is mounted on the robotic arm 112).

Additional techniques can be implemented to calibrate a medical instrument and/or maintain accurate orientation/position information for the medical instrument. For example, the control system 150 can use an orientation/position of a robotic arm 112 to determine a position/orientation of the catheter 130. The control system 150 can also determine how the catheter 130 shows up in image data captured by the scope 120 (e.g., use image processing or receive user input to determine a direction/angle in which the catheter 130 is positioned or enters the image data). Based on the position/orientation of the catheter 130 and how the catheter 130 shows up in the image data, the control system 150 can determine an orientation of the catheter 130 relative to the scope 120 and calibrate a control scheme. Further, the control system 150 can determine/calibrate an orientation of the catheter 130 relative to the scope 120 based on a sensor included on the catheter 130 and/or a sensor on the scope 120, such as an EM sensor, a gyroscope, an accelerometer, etc., and/or based on other localization techniques discussed herein. Moreover, the control system 150 can identify air bubbles depicted in image data (e.g., based on image processing, user input indicating a position of an air bubble or direction in which an air bubble is traveling, etc.), and use such information (along with information indicating where air bubbles typically collect/travel) to calibrate an orientation/control scheme of a medical instrument, such as an orientation of the scope 120, a control scheme for the catheter 130, and so on. Furthermore, the robotic system 110 can implement a mechanical keyed mating to require that the scope 120 be rolled to a lockout position before being mounted on the robotic arm 112. This may avoid situations in which the control system 150 is unaware of roll of the scope 120 before being mounted. Additionally, the control system 150 can implement a roll homing technique in which the scope 120 is automatically (or manually) rolled to a hard stop position each time the scope 120 is mounted on the robotic arm 112. This would assist the control system 150 in identifying an initial roll of the scope 120.

In examples, the medical system 100 may be used for percutaneous and/or endoscopic (e.g., ureteroscopic) procedures. Certain ureteroscopic procedures involve the treatment/removal of kidney stones. In some implementations, kidney stone treatment can benefit from the assistance of certain robotic technologies/devices, which may be similar to those shown in FIG. 1 and described in detail herein. Robotic medical solutions can provide relatively higher precision, superior control, and/or superior hand-eye coordination with respect to certain instruments compared to strictly manual procedures. For example, robotic-assisted percutaneous access to the kidney in accordance with some procedures can advantageously enable a urologist to perform both direct-entry endoscopic renal access and percutaneous renal access. Although some embodiments of the present disclosure are presented in the context of catheters, nephroscopes, ureteroscopes, and/or human renal anatomy, it should be understood that the principles disclosed herein may be implemented in any type of endoscopic and/or percutaneous procedure.

In one illustrative percutaneous procedure, the medical system 100 can be used to remove a kidney stone from the patient 140 through a percutaneous access path. For example, the physician 160 can interact with the control system 150 (e.g., via an I/O device(s) 156) to cause the robotic system 110 to advance and/or navigate the scope 120 from the urethra, through the bladder, up the ureter, and into the kidney where the stone is located. The control system 150 can provide information via the display(s) 152 regarding the scope 120 to assist the physician 160 in navigating the scope 120, such as real-time images captured therewith. In examples, the scope 120 can be driven from a first-person perspective (e.g., from the viewpoint of the scope 120). Once at the site of the kidney stone (e.g., within a calyx of the kidney), the scope 120 can be used to designate/tag a target location for the catheter 130 to access the kidney percutaneously. To minimize damage to the kidney and/or the surrounding anatomy, the physician 160 can designate a particular papilla as the target location for entering into the kidney percutaneously with the catheter 130. However, other target locations can be designated or determined.

The physician 160 can also interact with the control system 150 to cause the robotic system 110 to advance and/or navigate the catheter 130 through a percutaneous access path to the target location designated by the scope 120. In some embodiments, a needle or another medical instrument is inserted into the patient 140 to create the percutaneous access path. The control system 150 can provide information via the display(s) 152 regarding the catheter 130 to assist the physician 160 in navigating the catheter 130. For example, an interface(s) 154 can provide image data from the perspective of the scope 120. The image data may depict the catheter 130 (e.g., when within the field-of-view of an imaging device of the scope 120). In examples, the catheter 130 may be driven from a third-person perspective (e.g., from the viewpoint of the scope 120).

Once the scope 120 and/or the catheter 130 are located at the target location, the physician 160 can use the scope 120 to break up the kidney stone and/or use the catheter 130 to extract pieces of the kidney stone from the patient 140. For example, the scope 120 can deploy a tool (e.g., a laser, a cutting instrument, etc.) to fragment the kidney stone into pieces and the catheter 130 can suck out the pieces from the kidney through the percutaneous access path. In examples, the catheter 130 and/or the scope 120 can provide irrigation and/or aspiration to facilitate removal of the kidney stone. For instance, the catheter 130 can be coupled to an irrigation and/or aspiration system.

The medical system 100 can provide a variety of benefits, such as providing guidance to assist a physician in performing a procedure (e.g., instrument tracking, instrument navigation, instrument calibration, etc.), enabling a physician to perform a procedure from an ergonomic position without the need for awkward arm motions and/or positions, enabling a single physician to perform a procedure with one or more medical instruments, avoiding radiation exposure (e.g., associated with fluoroscopy techniques), enabling a procedure to be performed in a single-operative setting, providing continuous suction to remove an object more efficiently (e.g., to remove a kidney stone), and so on. For example, the medical system 100 can provide guidance information to assist a physician in using various medical instruments to access a target anatomical feature while minimizing bleeding and/or damage to anatomy (e.g., critical organs, blood vessels, etc.). Further, the medical system 100 can provide non-radiation-based navigational and/or localization techniques to reduce physician and patient exposure to radiation and/or reduce the amount of equipment in the operating room. Moreover, the medical system 100 can provide functionality that is distributed between at least the control system 150 and the robotic system 110, which can be independently movable. Such distribution of functionality and/or mobility can enable the control system 150 and/or the robotic system 110 to be placed at locations that are optimal for a particular medical procedure, which can maximize working area around the patient and/or provide an optimized location for a physician to perform a procedure.

Although various techniques and systems are discussed as being implemented as robotically-assisted procedures (e.g., procedures that at least partly use the medical system 100), the techniques and systems can be implemented in other procedures, such as in fully-robotic medical procedures, human-only procedures (e.g., free of robotic systems), and so on. For example, the medical system 100 can be used to perform a procedure without a physician holding/manipulating a medical instrument (e.g., a fully-robotic procedure). That is, medical instruments that are used during a procedure can each be held/controlled by components of the medical system 100, such as the robotic arm(s) 112 of the robotic system 110.

Further, although many techniques and systems are discussed in the context of the scope 120 rendezvousing with the catheter 130, the techniques and systems may be applicable to other types of medical instruments, such as any type of medical instrument that may meet up with another medical instrument at a treatment site or elsewhere, such as laparoscopic or other types of procedures.

Example Scope

Figure 2:
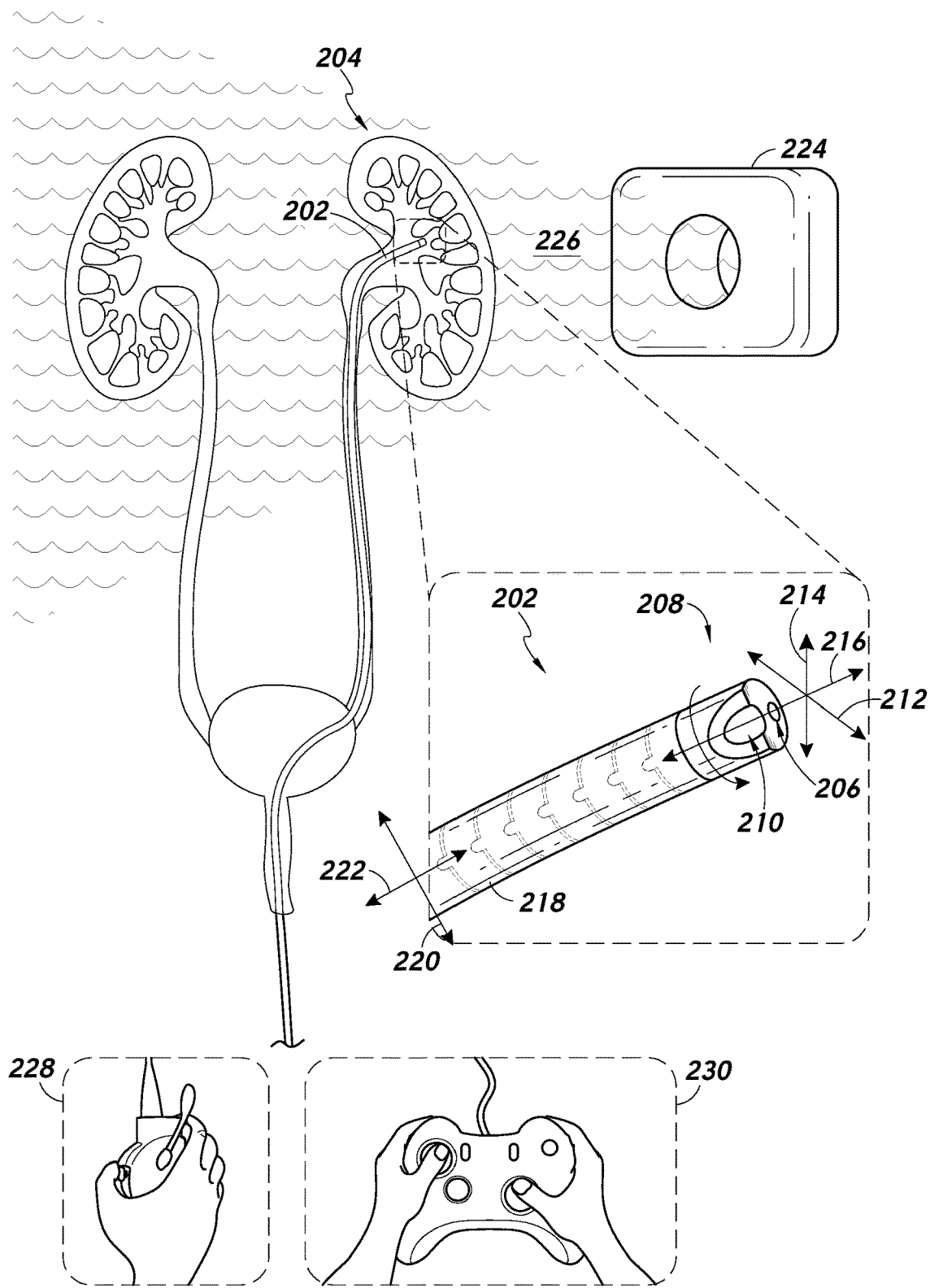
FIG. 2 illustrates an example scope disposed in portions of the urinary system of a patient in accordance with one or more embodiments.

FIG. 2 illustrates an example scope 202 (e.g., endoscope, ureteroscope, etc.) disposed in portions of the urinary system of a patient in accordance with one or more embodiments. The scope 202 may be representative of the scope 120 of FIG. 1 and/or any other scope discussed herein. The scope 202 may be used in ureteroscope procedures for investigating abnormalities in human ureters and/or treating the same. For example, ureteroscope procedures can be implemented to treat and/or remove kidney stones within a kidney 204. However, the scope 202 can be used in other types of procedures. As noted above, ureteroscope procedures and/or other types of procedures can be implemented manually at least in part and/or can be performed using robotic technologies at least in part, such as with the medical system 100 shown in FIG. 1.

The scope 202 can include an imaging device(s) 206 configured to capture image data, such as image data representing the internal anatomy of a patient. The imaging device 206 can include a camera, such as an optical camera and/or another imaging device. The imaging device 206 can include an optical fiber, fiber array, and/or lens. One or more optical components of the imaging device 206 can move along with a tip 208 of the scope 202 such that movement of the tip 208 of the scope 202 results in changes to the images captured by the imaging device 206. In some embodiments, the scope 202 can accommodate wires and/or optical fibers to transfer signals to/from an optical assembly and the distal end 208 of the scope 202. Further, the scope 202 can be configured to accommodate optical fibers to carry light from proximately located light sources, such as light-emitting diodes, to the distal end 208 of the scope. The distal end 208 of the scope 202 can include ports for light sources to illuminate an anatomical space when using the imaging device 206.

The scope 202 can also include a working channel 210 for deploying a medical instrument(s) (e.g., lithotripters, basketing devices, forceps, laser, etc.), irrigation, and/or aspiration to an operative region at a distal end 208 of the scope 202. In examples, the working channel 210 is offset to one side of the scope 202, such as that illustrated in FIG. 2. In other examples, the working channel 210 is positioned in the center of the scope 202 or at another location.

The scope 202 can comprise a rigid or flexible tube, and/or can be dimensioned to be passed within an outer sheath, catheter, introducer, or other lumen-type device. However, the scope 202 can be used without such devices, in some instances. In some embodiments, the scope 202 can include telescoping parts, such as an inner leader portion and an outer sheath portion, which can be manipulated to telescopically extend the scope 202.

The scope 202 can be configured to be articulated, such as with respect to at least the distal end 208 of the scope 202. For example, the scope 202 can be configured to move in various degrees of freedom (DOF), such as 3-DOF (e.g., x, y, and z movement), 4-DOF (e.g., x, y, z, and roll movement), 6-DOF (e.g., x, y, z, pitch, yaw, and roll movement), and so on, which can be coupled through bending properties of the scope 202. To illustrate, the tip 208 can be deflected on a yaw axis 212, a pitch axis 214, and/or a roll axis 216 (also referred to as "the longitudinal axis 216" or "z-axis 216"). The tip 208 or body 218 of the scope 202 can be elongated or translated in the longitudinal axis 216, x-axis 220, or y-axis 222. In embodiments where the scope 202 is equipped with a position sensor, the position sensor can provide position information, such as 3-DOF position information (e.g., x, y, and z coordinates), 5-DOF position information (e.g., x, y, and z coordinates and pitch and yaw angles), 6-DOF position information (e.g., x, y, and z coordinate and pitch, yaw, and roll angles), and so on.

For robotic implementations, robotic arms of a robotic system can be configured/configurable to manipulate the scope 202 using one or more elongate movement members. The elongate movement members may include one or more pull wires (e.g., pull or push wires), cables, fibers, and/or flexible shafts. For example, the robotic arms may be configured to actuate multiple pull wires (not shown) coupled to the scope 202 to deflect the tip 208 of the scope 202. Pull wires may include any suitable or desirable materials, such as metallic and non-metallic materials such as stainless steel, Kevlar, tungsten, carbon fiber, and the like. In some embodiments, the scope 202 is configured to exhibit nonlinear behavior in response to forces applied by the elongate movement members. The nonlinear behavior may be based on stiffness and compressibility of the scope 202, as well as variability in slack or stiffness between different elongate movement members.

In some embodiments, the scope 202 includes a sensor (sometimes referred to as a "position sensor") that is configured to generate and/or send sensor data to another device. The sensor data (sometimes referred to as "sensor position data") can indicate a position and/or orientation of the medical instrument 202 (e.g., the distal end 208 thereof) and/or can be used to determine/infer a position/orientation of the medical instrument 202. For example, the sensor can provide sensor data to a control system, which is then used to determine a position and/or an orientation of the scope 202. The sensor can be positioned on the distal end 208 of the scope 202 and/or another location. In some embodiments, a sensor can include an electromagnetic (EM) sensor with a coil of conductive material, or another form/embodiment of an antenna. FIG. 2 shows an EM field generator 224, which is configured to broadcast an EM field 226 that is detected by the EM sensor on the scope 202. The magnetic field 226 can induce small currents in coils of the EM field 226 position sensor, which may be analyzed to determine a distance and/or angle/orientation between the EM sensor and the EM field generator 224. Alternatively, or additionally, the scope 202 can include other types of sensors, such as a shape sensing fiber, accelerometer(s), gyroscope(s), satellite-based positioning sensor(s) (e.g., global positioning system (GPS) sensors), radio-frequency transceiver(s), and so on.

The scope 202 may be controllable in any suitable or desirable way, either based on user input or automatically. The controls 228, 230 (also referred to as "I/O devices") provide examples that may be used to receive user input. In examples, the control 228 is located on a proximal handle of the scope 202. Further, in examples, the control 230 is implemented as a controller, such as in the example of FIG. 2. In some embodiments, the control 228 and/or the control 230 are used in the context of robotic technologies, such as the medical system 100 of FIG. 1. For example, the control 230 can receive input from a user and provide an input signal to control a robotic system that is connected to the scope 202. Although the controls 228, 230 are shown as hand-held controllers, user input may be received using any type of I/O device, such as a touchscreen/pad, a mouse, a keyboard, a microphone, etc.

Example Catheter

Figure 3:
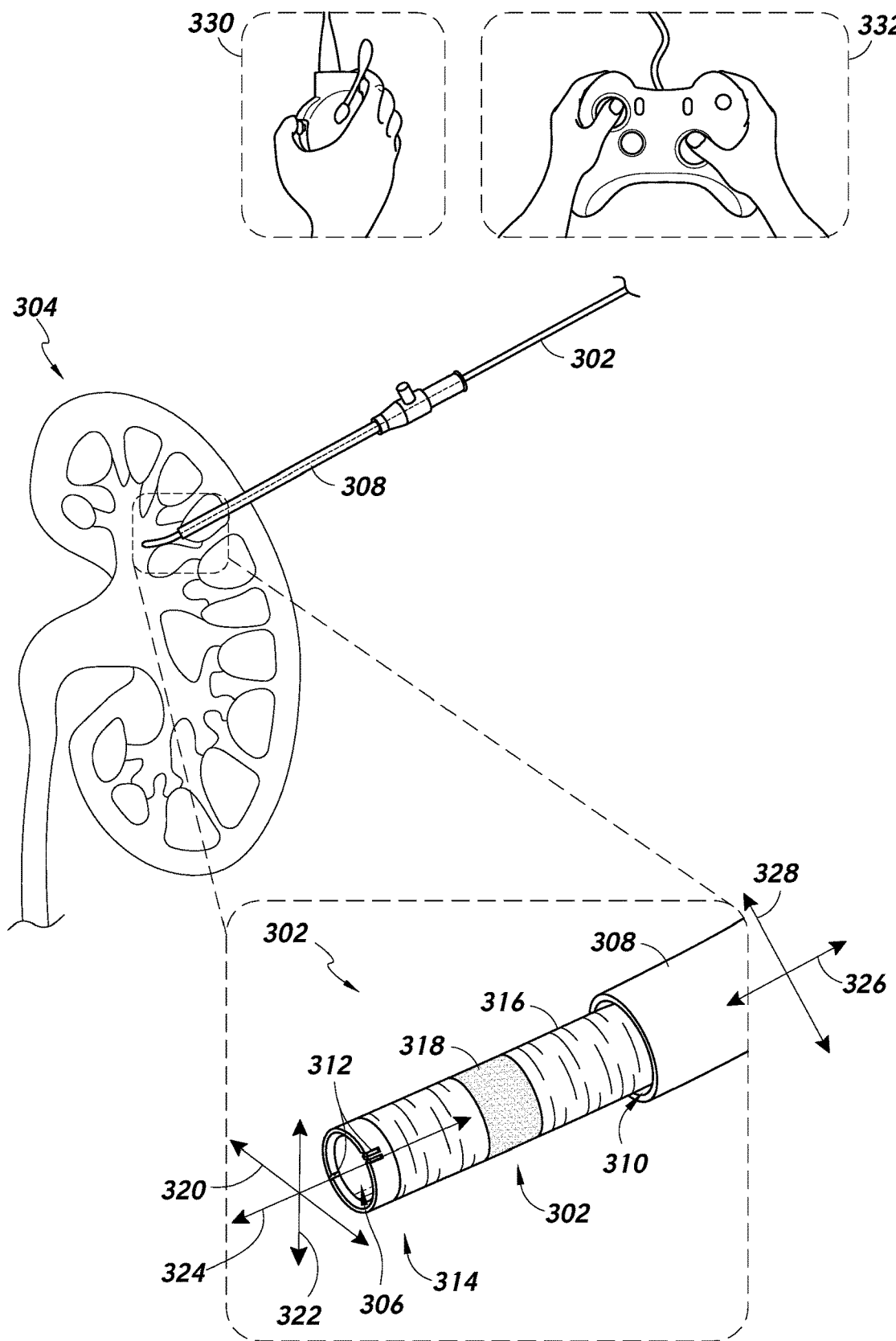
FIG. 3 illustrates an example catheter disposed in the kidney of a patient in accordance with one or more embodiments.

FIG. 3 illustrates a catheter 302 disposed in the kidney of a patient in accordance with one or more embodiments of the present disclosure. The catheter 302 may be representative of the catheter 130 of FIG. 1 and/or any other catheter discussed herein. For example, the catheter 302 may be used in ureteroscope procedures to treat and/or remove kidney stones within a kidney 304. However, the catheter 302 can be used in other types of procedures. As noted above, ureteroscope procedures and/or other types of procedures can be implemented manually at least in part and/or can be performed using robotic technologies at least in part, such as with the medical system 100 shown in FIG. 1.

In some embodiments, the catheter 302 is configured to provide irrigation and/or aspiration to an anatomical site. For example, the catheter 302 can include a lumen 306 to implement an aspiration outflow channel, such as to remove one or more kidney stone fragments from the kidney 304, and/or an irrigation inflow channel to provide fluid. In some embodiments, the catheter 302 is implemented along with another medical instrument(s) 308 to provide irrigation/aspiration to an anatomical site. For example, the catheter 302 can comprise a rigid or flexible tube(s) that is dimensioned to be passed within the medical instrument 308, which can include an outer sheath, introducer, nephroscope, or another lumen-type device. A channel 310 can be formed in a space between the outer wall of the catheter 302 and an inner wall/sheath of the medical instrument 308. The channel 310 can provide aspiration (and/or irrigation in some cases). With the catheter 302 disposed within the medical instrument 308, the catheter 302 and the shaft(s)/sheath(s) of the medical instrument 308 may be generally concentric.

The catheter 302 and the medical instrument 308 may have a generally circular cross-sectional shape over at least a portion thereof. Although the catheter 302 and/or the medical instrument 308 can provide both aspiration and irrigation, irrigation and aspiration may or may not be provided through the same instrument(s). For example, a scope can provide irrigation while the catheter 302/the medical instrument 308 provide aspiration. In some embodiments, the catheter 302 is configured to access an anatomical site via a percutaneous access path and/or provide irrigation/aspiration to the anatomical site.

The catheter 302 may include one or more markings 312 on a tip 314 of the catheter 302 (sometimes referred to as "the one or more orientation markings 312"). The one or more markings 312 can be used to calibrate the catheter 302 or otherwise view an orientation of the tip 314 of the catheter 302. The one or more markings 312 can include a deformation(s) (e.g., indentation, hole, notch, flat section, etc.), coloring (e.g., coloring one side of the tip a first color and the other side a different color, colored roman numerals, etc.), image(s) (e.g., a number, letter, shape, or other image), and the like. In the example of FIG. 3, the one or more markings 312 are implemented in the form of a roman numeral I indentation on one side of the tip 314 and a roman numeral II indentation on the opposite side of the tip 314. In examples, the one or more markings 312 can be implemented on both the outer diameter and the inner diameter of the tip 314. This can assist in viewing the orientation of the one or more markings 312 for various orientations/positions of the tip 314. In some embodiments, an indentation marking can be filled with a substance to provide a relatively smooth surface on the tip 314. In some embodiments, the tip 314 may include a particular shape to implement the one or more markings 312, such as a circle cross-section that has a flat portion. Further, in some embodiments, the one or more markings 312 are implemented in a particular manner that is more easily detectable by image processing techniques, such as a pattern, image (e.g., QR code), etc. Although the one or more markings 312 are implemented on an outer edge/diameter of the catheter 302, the one or more markings 312 can additionally, or alternatively be implemented on an inner edge/diameter of the tip 314 of the catheter 302. This can provide a smooth outer edge for the catheter 302, which can be advantageous in some cases to navigate the catheter 302 and/or avoid damage to anatomy of a patient. Although the one or more markings 312 are illustrated on the tip 314 of the catheter 302, the one or more markings 312 can be located at other locations, such as a body 316 of the catheter 302.

The catheter 302 can also include one or more markings 318 on a body of the catheter 302 (sometimes referred to as "the one or more depth markings 318"). The one or more markings 318 can used to determine how far the catheter 302 has been inserted into the anatomy. For example, the catheter 302 can implement multiple markings 318 located at different distances from the tip 314 of the catheter 302. If a physician/control system is able to view/detect a first marking located at a particular distance relative to the tip 314 of the catheter 302, the physician/control system can determine that the catheter 302 is inserted into the patient at least the particular distance. The one or more markings 318 can be implemented in a similar manner as the one or more markings 312 discussed above, such as with a deformation(s) (e.g., indentation, hole, notch, flat section, etc.), coloring, image(s) (e.g., a number, letter, shape, or other image), and the like. In the example of FIG. 3, the marking 318 is illustrated with a colored marking that extends around a circumference of the body 316 of the catheter 302. In examples, the one or more markings 318 (and/or the one or more markings 312) can be detected/visible with fluoroscopy, ultrasonic cameras, and the like.

The catheter 302 can be configured to be articulated, such as with respect to at least the distal end 314 of the catheter 302. For example, the catheter 302 can be configured to move in various degrees of freedom (DOF), such as 3-DOF (e.g., x, y, and z movement), 4-DOF (e.g., x, y, z, and roll movement), 6-DOF (e.g., x, y, z, pitch, yaw, and roll movement), and so on, which can be coupled through bending properties of the catheter 302. To illustrate, the tip 314 can be deflected on a yaw axis 320, a pitch axis 322, and/or a roll axis 324 (also referred to as "the longitudinal axis 324" or "z-axis 324"). In some embodiments, the catheter 302 is configured to move in 2 independent DOFs (e.g., with yaw and pitch pull wires) and/or is not configured for roll movements. However, the catheter 302 can be configured for roll and/or other types of movement in some cases. The tip 314 or body 316 of the catheter 302 can be elongated or translated in the longitudinal axis 324, x-axis 326, or y-axis 328. In embodiments where the catheter 302 is equipped with a position sensor, the position sensor can provide position information, such as 3-DOF position information (e.g., x, y, and z coordinates), 5-DOF position information (e.g., x, y, and z coordinates and pitch and yaw angles), 6-DOF position information (e.g., x, y, and z coordinate and pitch, yaw, and roll angles), and so on.

For robotic implementations, robotic arms of a robotic system can be configured/configurable to manipulate the catheter 302 using one or more elongate movement members. The elongate movement members may include one or more pull wires (e.g., pull or push wires), cables, fibers, and/or flexible shafts. For example, the robotic arms may be configured to actuate multiple pull wires (not shown) coupled to the catheter 302 to deflect the tip 314 of the catheter 302. Pull wires may include any suitable or desirable materials, such as metallic and non-metallic materials such as stainless steel, Kevlar, tungsten, carbon fiber, and the like. In some embodiments, the catheter 302 is configured to exhibit nonlinear behavior in response to forces applied by the elongate movement members. The nonlinear behavior may be based on stiffness and compressibility of the catheter 302, as well as variability in slack or stiffness between different elongate movement members.

In some embodiments, the tip 314 of the catheter 302 is implemented with a material that avoids degradation in certain contexts, such as catastrophic degradation. For example, the tip 314 can be implemented with stainless steel (or other types of steel), titanium, tungsten, and/or other materials (which may have relatively high melting points) that can generally maintain its structure when laser beams from a scope inadvertently and/or occasionally contact the tip 314 of the catheter 302. However, the tip 314 and/or any other portion of the catheter 302 can be implemented with other materials.

Although some embodiments are discussed in the context of the catheter 302 being implemented without a position sensor, in other embodiments the catheter 302 includes a position sensor that is configured to generate and/or send sensor data to another device. The sensor data can indicate a position and/or orientation of the catheter 302 (e.g., the distal end 314 thereof) and/or can be used to determine/infer a position/orientation of the catheter 302. The sensor can be positioned on the distal end 314 of the catheter 302 and/or another location. In some embodiments, the position sensor includes an electromagnetic (EM) sensor with a coil of conductive material, or another form/embodiment of an antenna. Alternatively, or additionally, the position sensor can include other types of sensors, such as a shape sensing fiber, accelerometer(s), gyroscope(s), satellite-based positioning sensor(s) (e.g., global positioning system (GPS) sensors), radio-frequency transceiver(s), and so on.

Further, although not illustrated in FIG. 3, in some embodiments the catheter 302 can include an imaging device(s) configured to capture image data, such as image data representing the internal anatomy of a patient. For example, the catheter 302 can include an imaging device located on the tip 314 of the catheter 302. In some cases, image data from the imaging device can be used to drive the catheter 302 from the perspective of the catheter 302.

The catheter 302 may be controllable in any suitable or desirable way, either based on user input or automatically. The controls 330, 332 (also referred to as "I/O devices") provide examples that may be used to receive user input. In examples, the control 330 is located on a proximal handle of the catheter 302. Further, in examples, the control 332 is implemented as a controller, such as in the example of FIG. 2. In some embodiments, the control 330 and/or the control 332 are used in the context of robotic technologies, such as the medical system 100 of FIG. 1. For example, the control 332 can receive input from a user and provide an input signal to control a robotic system that is connected to the catheter 302. Although the controls 330, 332 are shown as hand-held controllers, user input may be received using any type of I/O device, such as a touchscreen/pad, a mouse, a keyboard, a microphone, etc.

Example Control Modes

Figures 1, 4:
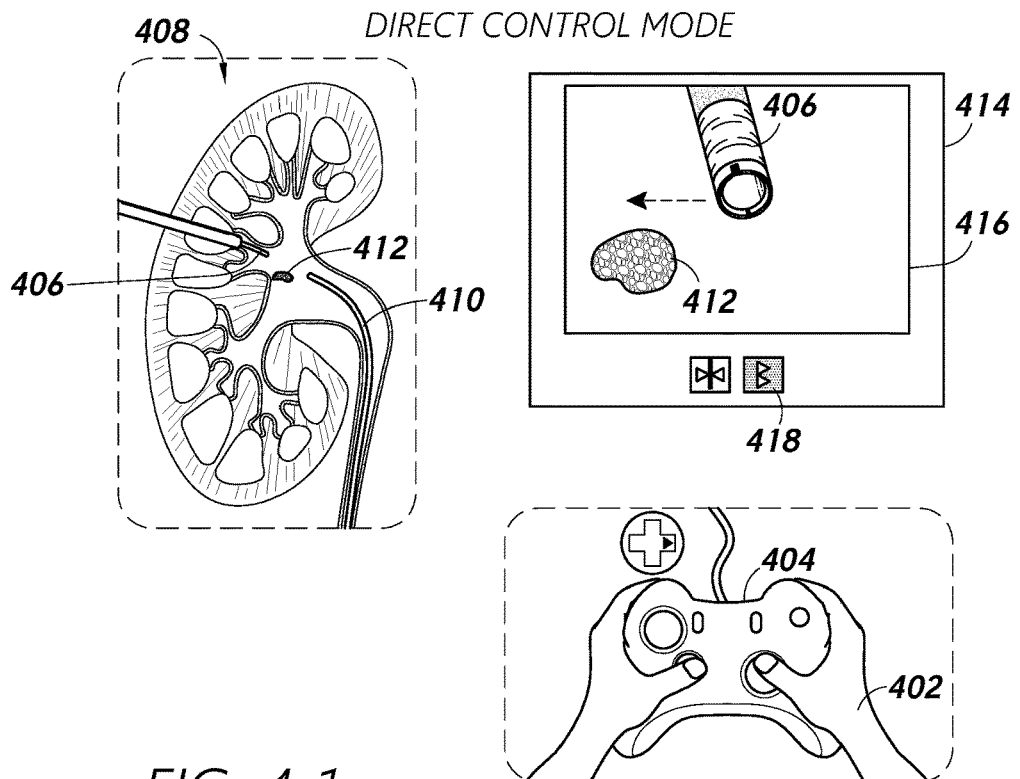
Figures 2, 4:
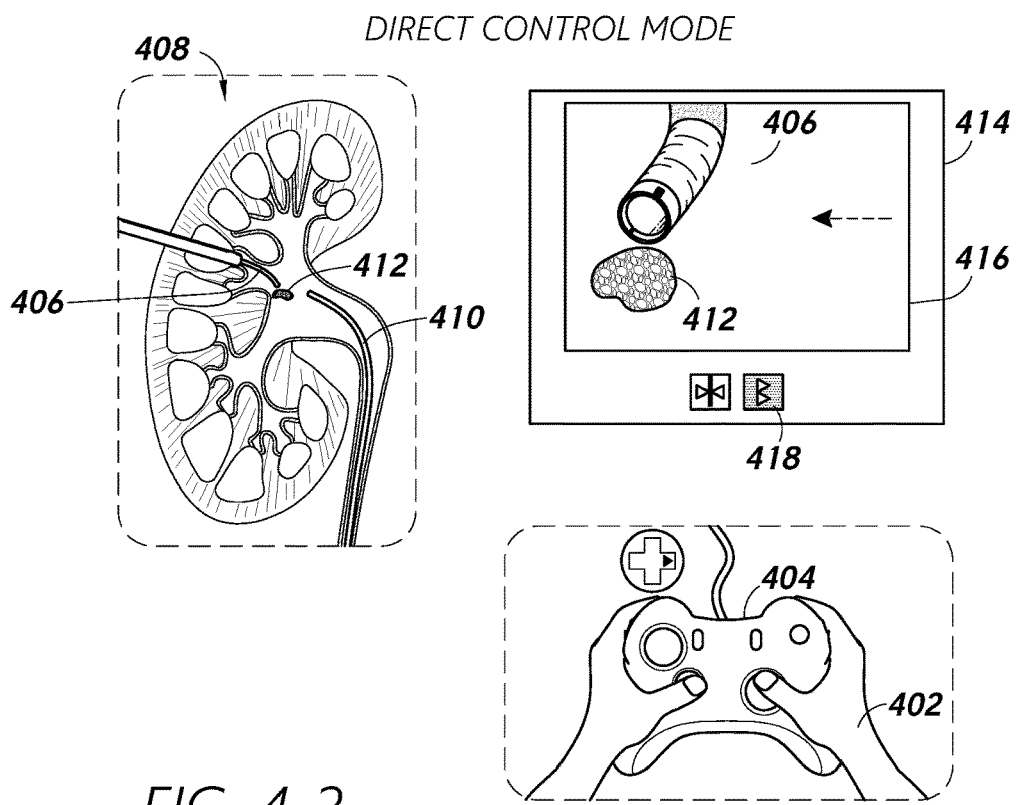
Figures 1, 5:
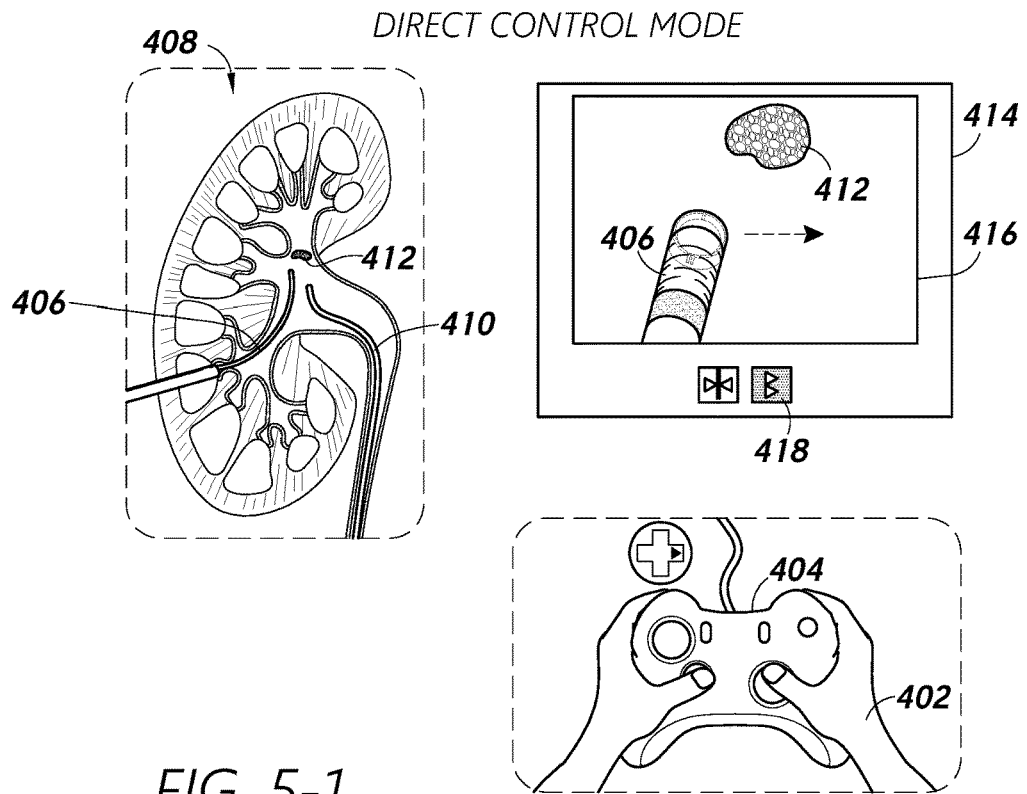
Figures 2, 5:
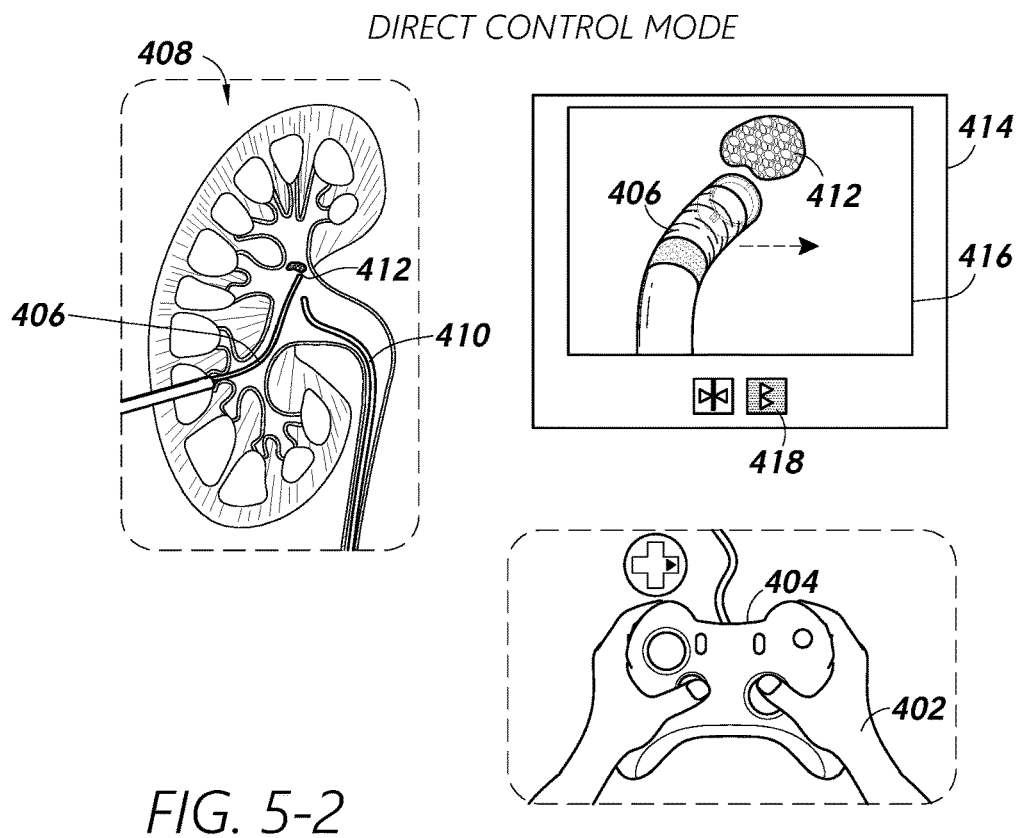
Figures 1, 6:
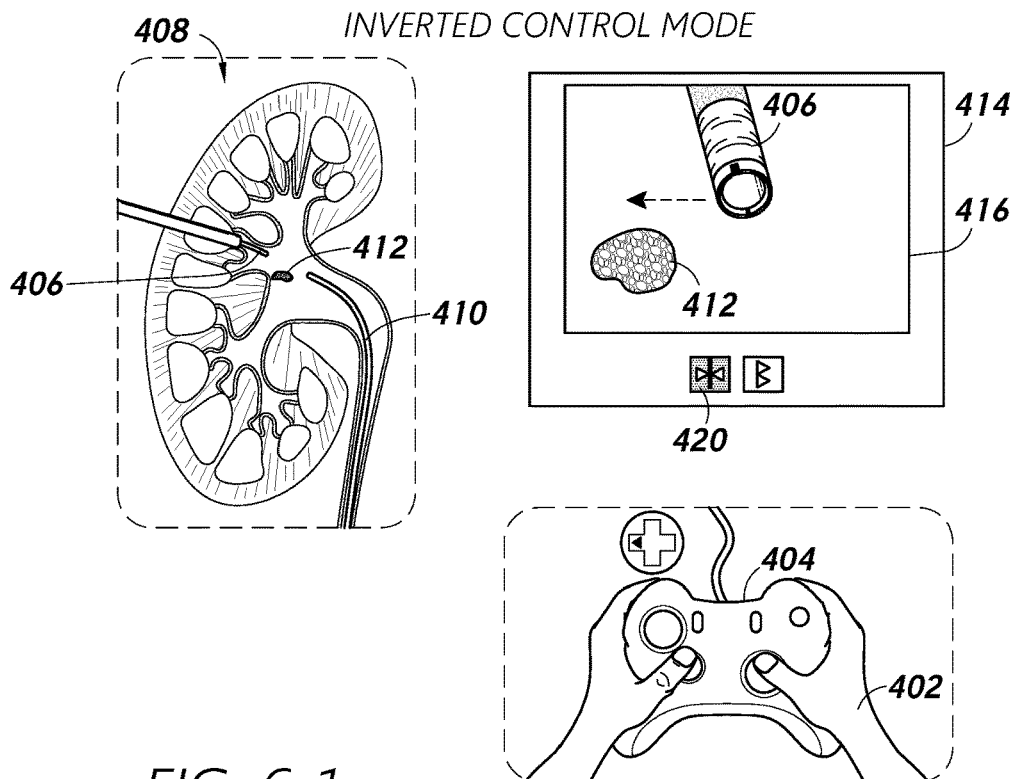
Figures 2, 6:
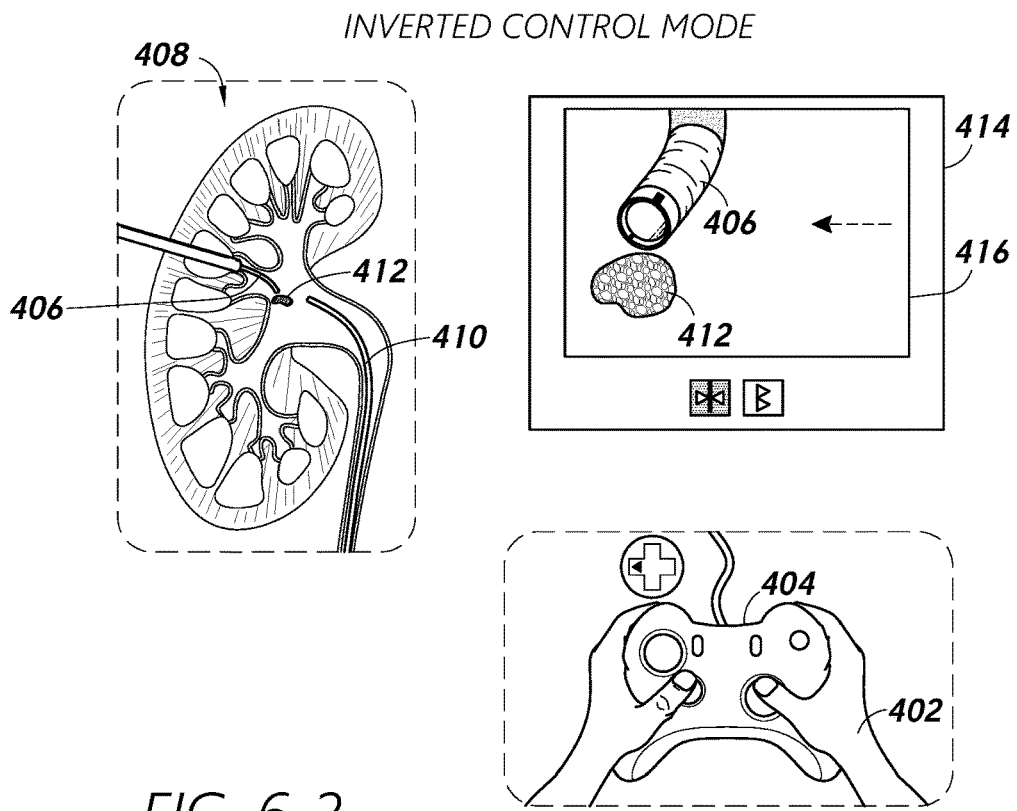

FIGS. 4 through 6 illustrate example implementations of control/driving modes to drive a medical instrument from the perspective of another medical instrument in accordance with one or more embodiments. These control modes are discussed in the context of a physician 402 using an I/O device 404 to drive a catheter 406 within a kidney 408 from the perspective of a scope 410 to remove a kidney stone 412. A user interface 414 can be presented to assist the physician 402 in driving the catheter 406. As illustrated, the user interface 414 can present image data 416 from the perspective of the scope 410 (e.g., image data captured by the scope 410). In these examples, the physician 402 can select a control mode to implement for various orientations/positions of the catheter 406 relative to the scope 410. However, the control mode can be selected in a variety of manners, as discussed herein.

FIGS. 4 through 6 discuss a direct control mode and/or an inverted control mode to navigate the catheter 406 for various orientations of the catheter 406 relative to the scope 410. Although an inverted control mode may often be used when the catheter 406 is facing the scope 410 and a direct control mode may often be used when the catheter 406 and the scope 410 facing in the same direction, the inverted control mode and/or the direct control mode can be implemented in any context, such as other orientations of the instruments relative to each other and/or the kidney stone 412. Further, in some embodiments, multiple driving modes can be implemented during the same procedure, such as by the physician 402 switching between the driving modes as the catheter 406/scope 410 is repositioned during a procedure.

These examples illustrate that the catheter 406 can enter the kidney 408 from a variety of locations relative to the kidney stone 412. For example, in FIGS. 4-1 and 4-2 and FIGS. 6-1 and 602, the catheter 406 enters the kidney 408 behind the kidney stone 412 with respect to the scope 410. In FIGS. 5-1 and 5-2, the catheter 406 accesses the kidney stone 412 from substantially the same direction as the scope 410. However, the catheter 406 can access the kidney stone 412 from a variety of other locations/paths with respect to the kidney 408 and/or the scope 410. Further, the scope 410 can be positioned in a variety of other locations.

FIGS. 4-1 and 4-2 illustrate driving of the catheter 406 in a direct control mode (also referred to as a "parallel mode") when the catheter 406 is facing the scope 410 in a head on manner. As such, an icon 418 indicates that the direct control mode is selected. In this example, the physician 402 selects a directional control on the I/O device 404 that is associated with a right direction relative to the I/O device 404. Since the direct control mode is implemented, the catheter 406 can be controlled in a corresponding manner with respect to the catheter 406. That is, the catheter 406 moves to the right relative to a coordinate/control frame of the catheter 406. As illustrated in FIG. 4-2, the user interface 414 shows the catheter 406 as moving to the left, since the catheter 406 is facing the scope 410 in a head-on manner.

FIGS. 5-1 and 5-2 illustrate driving of the catheter 406 in the direct control mode when the catheter 406 and the scope 410 are substantially facing in the same direction. In this example, the physician 402 again selects the directional control on the I/O device 404 that is associated with the right direction relative to the I/O device 404. Since the direct control mode is implemented, the catheter 406 moves to the right relative to the coordinate/control frame of the catheter 406. As illustrated in FIG. 5-2, the user interface 414 shows the catheter 406 as moving to the right, since the catheter 406 are facing in the same general direction. In examples, the direct control mode may be implemented more frequently in the context of FIGS. 5-1 and 5-2, where the catheter 406 and the scope 410 are substantially facing the kidney stone 412 from the same area, since it may provide a more user-friendly view of movement of the catheter 406 via the user interface 414.

FIGS. 6-1 and 6-2 illustrate driving of the catheter 406 in an inverted control mode (also referred to as a "mirrored mode") when the catheter 406 is facing the scope 410 in a head on manner. An icon 420 indicates that the inverted control mode is selected. In this example, the physician 402 selects a directional control on the I/O device 404 that is associated with a left direction relative to the I/O device 404. Since the inverted control mode is implemented, the catheter 406 can be controlled in an inverted manner with respect to the catheter 406. That is, the catheter 406 moves to the left relative to a coordinate/control frame of the catheter 406. To do so, a horizontal component of a direction of movement for the coordinate/control frame can be inverted, as discussed in further detail below. As illustrated in FIG. 6-2, the user interface 414 shows the catheter 406 as moving to the left, since the catheter 406 is facing the scope 410 in a head on manner. In examples, the inverted control mode may be implemented more frequently in the context of FIGS. 6-1 and 6-2, where the catheter 406 and the scope 410 are substantially facing each other, since it may provide a more user-friendly view of movement of the catheter 406 via the user interface 414.

Example Instrument-Driving Interface

Figure 7:
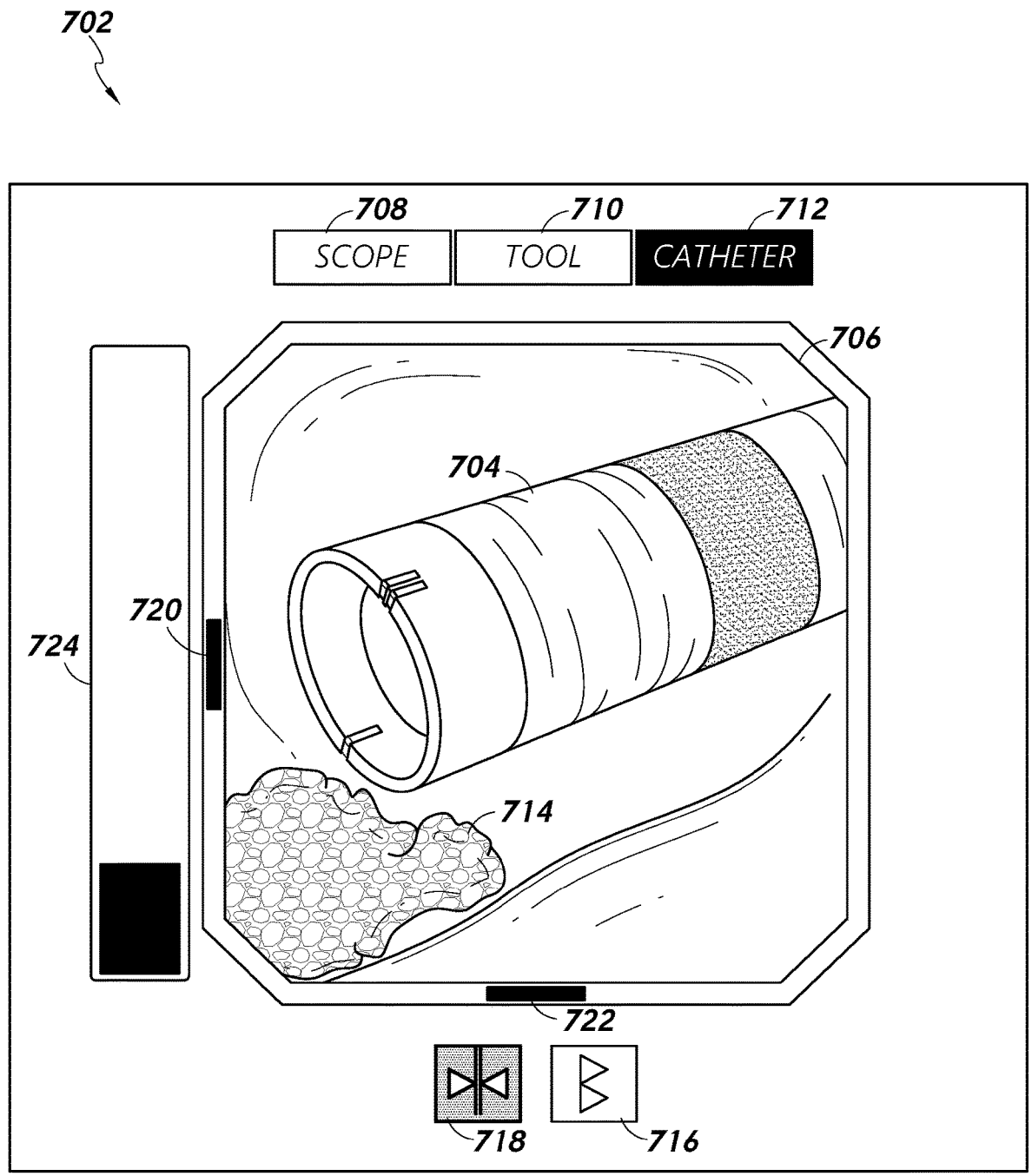
FIG. 7 illustrates an example interface to control/navigate a medical instrument in accordance with one or more embodiments.

FIG. 7 illustrates an example interface 702 to control/navigate a medical instrument in accordance with one or more embodiments. For example, the interface 702 can provide information to assist a physician in driving a scope from the perspective of the scope, driving a catheter 704 from the perspective of the scope, and/or using another medical instrument. As discussed below, the interface 702 can include one or more interface elements (e.g., icons), which can be selected through a touchscreen, a controller, mouse, trackpad, or another type of I/O device.

As shown, the interface 702 can present image data 706, which may generally be from a perspective of the scope. That is, the image data 706 can depict at least a portion of a field-of-view of an imaging device on the scope. In some embodiments, the image data 706 is presented as an original image view (as discussed above), while in other embodiments the image data 706 is presented as a rotated image view. Although the interface 702 generally presents image data from the perspective of the scope, the interface 702 can additionally, or alternatively, present image data from the perspective of another medical instrument. For example, in cases where the catheter 704 is being driven from the perspective of the catheter 704, the interface 702 can present image data from the point-of-view of the catheter 704.

The interface 702 can include interface elements 708, 710, 712 to select a medical instrument to control. The interface element 708 enables control of the scope, the interface element 710 enables control of a medical instrument associated with the scope (also referred to as a "tool"), and the interface element 712 enables control of the catheter 704. The medical instrument associated with the scope can include a laser, a cutting instrument, lithotripter, basketing device, forceps, and so on. As discussed herein, such medical instrument can be deployed through a working channel of the scope, such as to break up a kidney stone 714 for extraction by the catheter 704.

The interface 702 can include an interface element 716 to enable a direct driving/control mode and an interface element 718 to enable an inverted driving/control mode. For example, when driving the catheter 704 from the perspective of the scope (i.e., the interface element 712 is selected), and the direct control mode is enabled (i.e., the interface element 716 is selected), the catheter 704 can be driven in a corresponding manner with respect to a perspective of the catheter 704. In contrast, when driving the catheter 704 from the perspective of the scope (i.e., the interface element 712 is selected), and the inverted control mode is enabled (i.e., the interface element 718 is selected), the catheter 704 can be driven an inverted manner with respect to a perspective of the catheter 704.

The interface 702 can also include other information to assist a user in controlling a medical instrument. For example, articulation bars 720, 722 can be presented around the image data 706 to view an amount of articulation associated with the medical instrument that is selected. The top/bottom articulation bar 722 can indicate an amount of vertical articulation (e.g., how far the medical instrument has been moved in a vertical direction). For example, the top/bottom articulation bar 722 can be positioned above or below the image data 706 and/or expand/contract in length to indicate vertical articulation of the medical instrument. In the example of FIG. 7, the top/bottom articulation bar 722 is positioned below the image data 706 to indicate that the catheter 704 is articulated down. The right/left articulation bar 720 can indicate an amount of horizontal articulation (e.g., how far the medical instrument has been moved in a horizontal direction). For example, the right/left articulation bar 720 can be positioned to the right or left of the image data 706 and/or expand/contract in length to indicate horizontal articulation of the medical instrument. In the example of FIG. 7, the right/left articulation bar 720 is positioned to the left of the image data 706 to indicate that the catheter 704 is articulated to the right in the mirrored mode. As such, when the catheter 704 is being controlled, the articulation bars 720, 722 can indicate an amount of movement for the catheter 704, such as how far the catheter 704 has articulated right, left, up, or down in the interface 704 with respect to a longitudinal axis of the catheter 704. In some cases, when an articulation bar is illustrated with a shortest allowed length (and/or without the articulation bar), this may indicate that the catheter 704 is aligned with the longitudinal axis of the catheter 704 (e.g., there is no articulation).

In the example of FIG. 7, the articulation bars 720, 722 are substantially centered on the image data 706 and expand/contract in length as the associated medical instrument is articulated. For example, the articulation bar 722 along the bottom edge of the image data 706 can increase/decrease in length, while maintaining alignment with a vertical axis through a center of the image data 706, when the medical instrument is navigated to the up/down in the interface 702. Similarly, the articulation bar 720 along the side edge of the image data 706 can increase/decrease in length, while maintaining alignment with a horizontal axis through a center of the image data 706, when the medical instrument is navigated right/left in the interface 702. However, in other examples, the articulation bars 720, 722 can be manipulated in other manners to indicate articulation of a medical instrument, such as moving in a vertical/horizontal direction relative to the interface 702 without changing in length.

In some embodiments, one or more of the articulation bars 720, 722 can be updated based on calibration of a control scheme. For example, if the articulation bars 720, 722 initially indicate that a catheter is articulated in a direction, and a control scheme for the catheter is adjusted, the articulation bars 720, 722 can be updated to indicate that the catheter is articulated in a different direction that accurately reflects the actual orientation of the catheter relative to a scope. In contrast, in some embodiments, an orientation of the image data 706 can be maintained after calibration of the control scheme. However, the orientation of the image data 706 can be updated to reflect an updated control scheme, in some cases.

The interface 702 can also present a progress bar 724 to indicate a position of a medical instrument being controlled relative to a target location or another landmark. For example, the progress bar 724 can indicate a proximity of the scope to a target location that has been tagged/designated by the scope, such as a papilla that is designated as an entry point for the catheter 704 to enter the kidney. In some cases, when the progress bar 724 is completely filled, this can indicate that the scope is at the target location. In other cases, the progress bar 724 can include a marking along the bar to indicate a position of the target location. Additionally, or alternatively, the progress bar 724 can indicate other progress information, such as a proximity of the scope to the catheter 704/the kidney stone 714, a proximity of the catheter 704 to the scope/target location/kidney stone 714, a proximity of the tool to the catheter 704/target location/kidney stone 714, and so on. In some embodiments, the progress bar 724 can include information for a medical instrument that is selected (e.g., a medical instrument that is currently being driven).

Although not illustrated in FIG. 7, in some embodiments the interface 702 can present image data captured by an external imaging device, such as one or more x-ray images, CT images, or the like. Such image data can depict the catheter 704, the scope, another medical instrument, internal anatomy of a patient, and so on. In some examples, the image data can be captured as part of a fluoroscopy procedure.

Example Flow Diagram—Instrument Control Process

Figure 8:
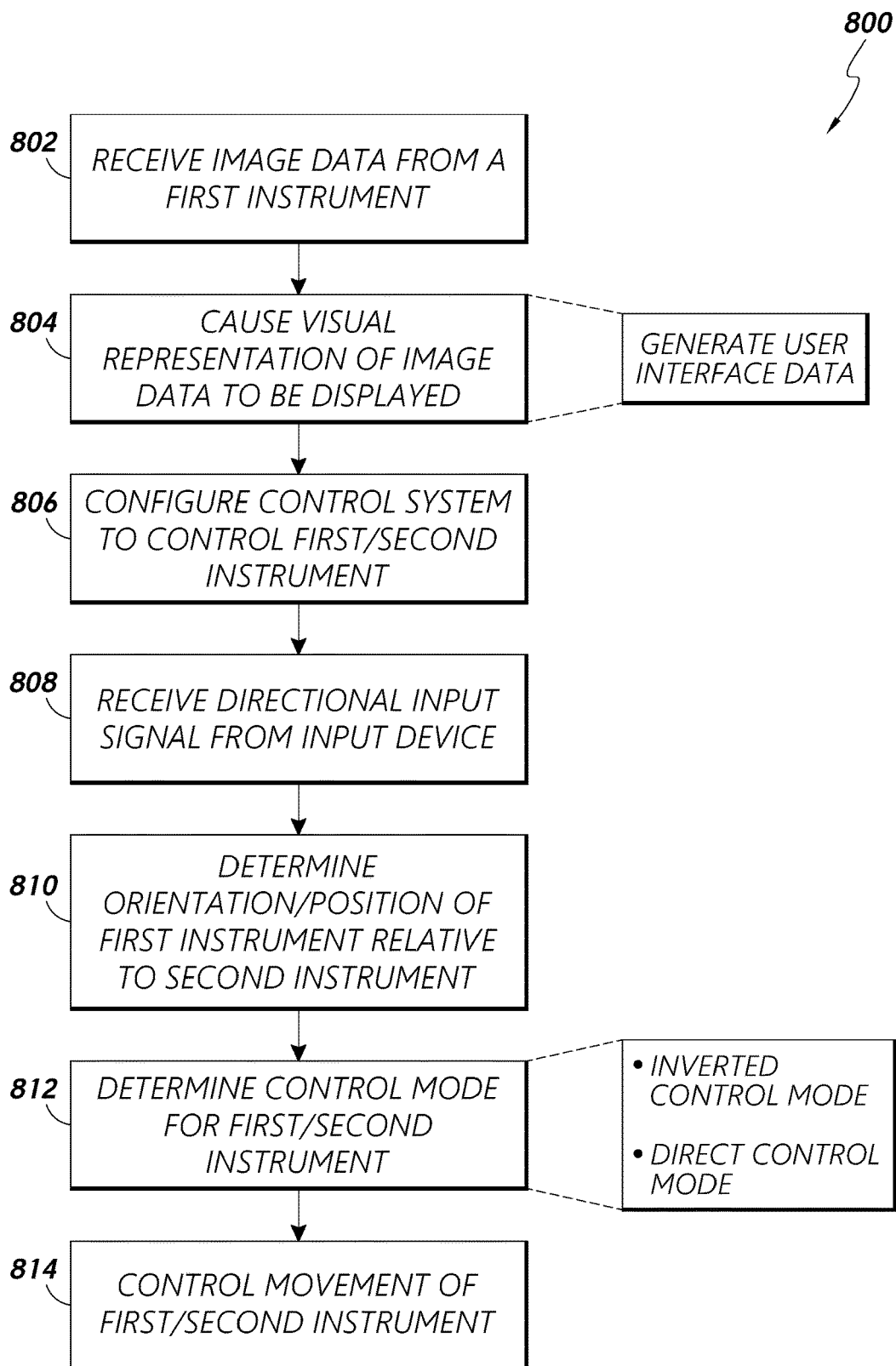
FIG. 8 illustrates an example flow diagram of a process for controlling a medical instrument from the perspective of another medical instrument in accordance with one or more embodiments.

FIG. 8 illustrates an example flow diagram of a process 800 for controlling a medical instrument from the perspective of another medical instrument in accordance with one or more embodiments. The various operations associated with the process 800 can be performed by control circuitry implemented in any of the devices/systems discussed herein or a combination thereof, such as the control system 150, the robotic system 110, the table 170, the scope 120, the catheter 130, and/or another device of FIG. 1.

At block 802, the process 800 can include receiving image data from a first instrument. For example, control circuitry can receive the image data from the first instrument that is configured to access an anatomical site via a first access path. The image data can be representative of the anatomical site and/or a second instrument that is configured to access the anatomical site via a second access path. In some embodiments, the first instrument is a scope and/or the second instrument is a catheter.

At block 804, the process 800 can include causing a visual representation of the image data to be displayed. For example, the control circuitry can generate user interface data representing a user interface and/or the visual representation of the image data. The control circuitry can cause the user interface and/or the visual representation to be displayed based on the user interface data.

At block 806, the process 800 can include configuring a control system to control the first instrument or the second instrument. For example, control circuitry can receive an input signal from the input device indicating to switch control from the second instrument to the first instrument, or vice versa. Based on such input signal, the control circuitry can configure the control system to control the first instrument or the second instrument. As such, in some embodiments, the same input device can be used to control the first instrument and the second instrument.

At block 808, the process 800 can include receiving a directional input signal from an input device. For example, a user can provide input via the input device, which can include multiple input controls that are each associated with a particular direction relative to the input device. The input device can generate the directional input signal based on the input and send the directional input signal to the control circuitry. The directional input signal can be associated with a direction relative to the input device. The direction can be associated with a horizontal/vertical component.

At block 810, the process 800 can include determining an orientation and/or position of the first instrument relative to the second instrument. For example, the control circuitry can perform one or more localization techniques to track an orientation/position of the first instrument and an orientation/position of the second instrument. The control circuitry can use such information to determine an orientation/position of the first instrument relative to the second instrument.

At block 812, the process 800 can include determining a control mode for the first/second instrument. For instance, the control circuitry can determine a direct control mode associated with controlling an instrument in a direct manner with respect to input received and/or an inverted control mode associated with controlling the instrument in an inverted manner with respect to input received. In one example, the control circuitry can receive an input signal indicating a control mode from among a plurality of control modes. The input signal can be received from the input device or another I/O device. In another example, the control circuitry can automatically determine a control mode from among a plurality of control mode based on the orientation/position of the first instrument relative to the second instrument. For instance, the control circuitry can select a predetermined control mode that is associated with a particular orientation of the instruments relative to each other.

At block 812, the process 800 can include controlling movement of the first/second instrument. For example, the control circuitry can generate a control signal based on the control mode and/or the directional input signal. The control circuitry can send the control signal to a robotic system to cause the robotic system to manipulate the first/second instrument, resulting in movement of the first/second instrument at an anatomical site. To illustrate, if a directional input signal is received that is associated with a first direction relative to the input device, and the inverted control mode is determined, the second instrument can be control to move in a second direction relative to a frame of reference for the second instrument. The second direction can be associated with a horizontal/vertical component that has an opposite sign to a horizontal/vertical component associated with the first direction. In contrast, if a directional input signal is received that is associated with a first direction relative to the input device, and the direct control mode is determined, the second instrument can be control to move in a second direction relative to a frame of reference for the second instrument. The second direction can be associated with a horizontal/vertical component that has a same sign as a horizontal/vertical component associated with the first direction. The frame of reference can include a control frame and/or a coordinate frame.

In some embodiments, the control circuitry can control insertion/retraction of the first/second instrument based on the determined control mode. To illustrate, if a directional input signal associated with insertion is received, and the inverted control mode is determined, the second instrument can be controlled to be retracted. In contrast, if a directional input signal associated with retraction is received, and the inverted control mode is determined, the second instrument can be controlled to be inserted.

In some embodiments, one or more of blocks 802-814 can be repeated any number of times to control the first instrument and/or the second instrument in one or more control modes based on input received via the input device.

Example Coordinate/Control Frames and Control Implementations

Figures 1, 9:
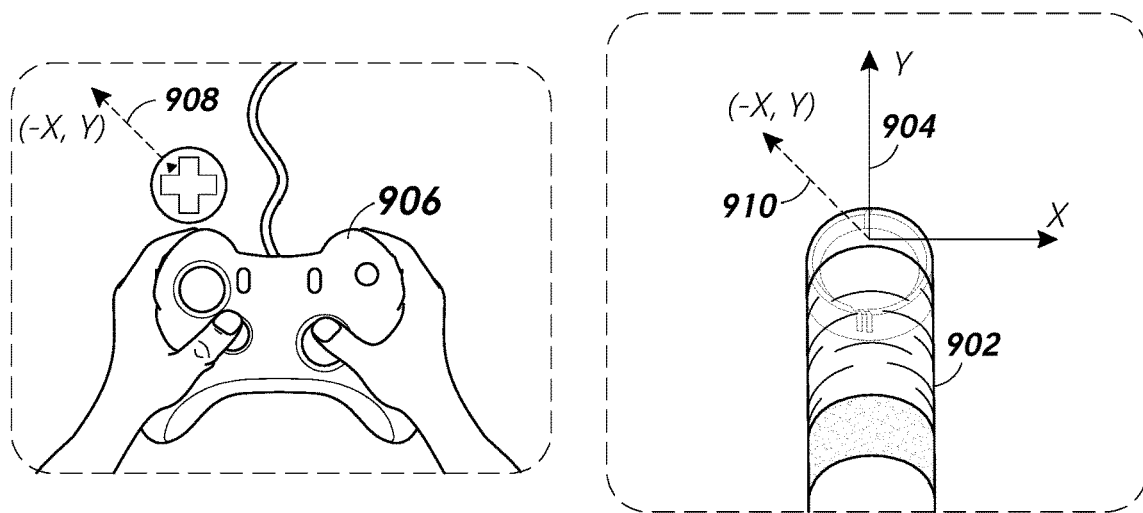
Figures 2, 9:
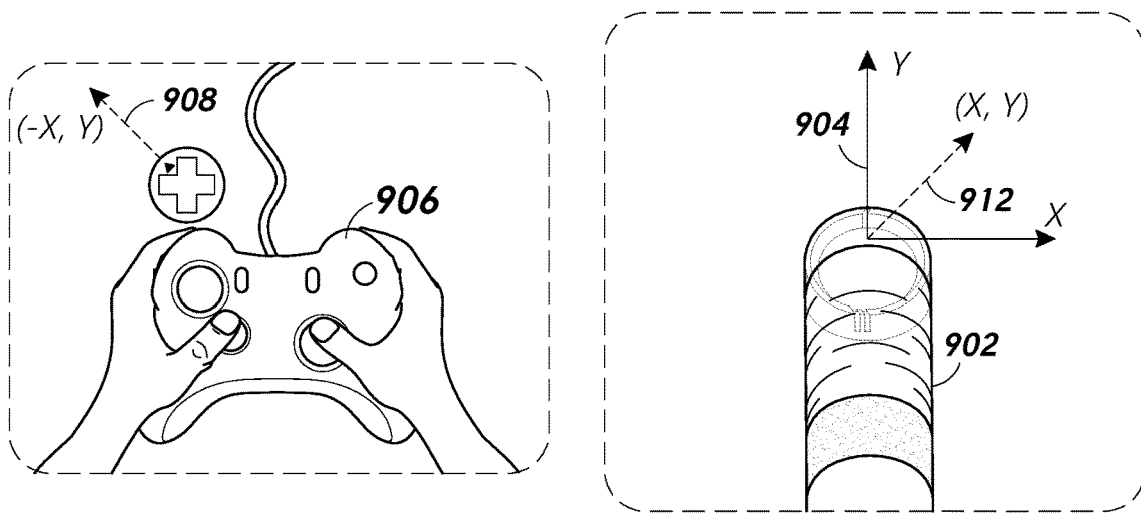

FIGS. 9-1 and 9-2 illustrate example implementations of driving a medical instrument from a first-person perspective for different control modes with respect to a coordinate frame for the medical instrument in accordance with one or more embodiments. In these figures, a catheter 902 is illustrated from substantially a perspective of the catheter 902, with a coordinate frame 904 associated with a tip of the catheter 902. Although various conventions can be used for a coordinate frame, for ease of illustration the description herein will often refer to the "forward" direction (e.g., insert/retract) as corresponding to positive z, the "right" direction as corresponding to positive x, and the "up" direction as corresponding to positive y. The z-vector can extend along a longitudinal axis of a medical instrument. For ease of illustration, the z-vectors for the coordinate frames are not illustrated in FIGS. 9-1 and 9-2. Although discussed in the context of a coordinate frame, the coordinate frame 904 can be representative of a control frame, in some cases.

The catheter 902 can be controlled based on input received via an I/O device 906, such as by selecting a directional control on the I/O device 906. Here, the input is associated with a direction/vector 908 relative to the I/O device 906, which has a negative x value (horizontal component) and a positive y value (vertical component) relative to the I/O device 906. The horizontal/vertical components can indicate a direction and/or magnitude.

As illustrated, the catheter 902 can move in different manners (with respect to the coordinate frame 904) for different control modes. In a direct control mode (as shown in FIG. 9-1), the catheter 902 is controlled to move in a direction/vector 910, which has a negative x value and a positive y value with respect to the coordinate frame 904. In contrast, for the same input, in an inverted control mode (as shown in FIG. 9-2), the catheter 902 is controlled to move in a direction/vector 912, which as a positive x value and a positive y value with respect to the coordinate frame 904. Here, the direction/vector 912 has a same magnitude as the direction 908 (or by some factor), but has an x value that has an opposite sign of the x value of the direction/vector 908. As such, a horizontal component can be inverted for the inverted control mode.

Figures 1, 10:
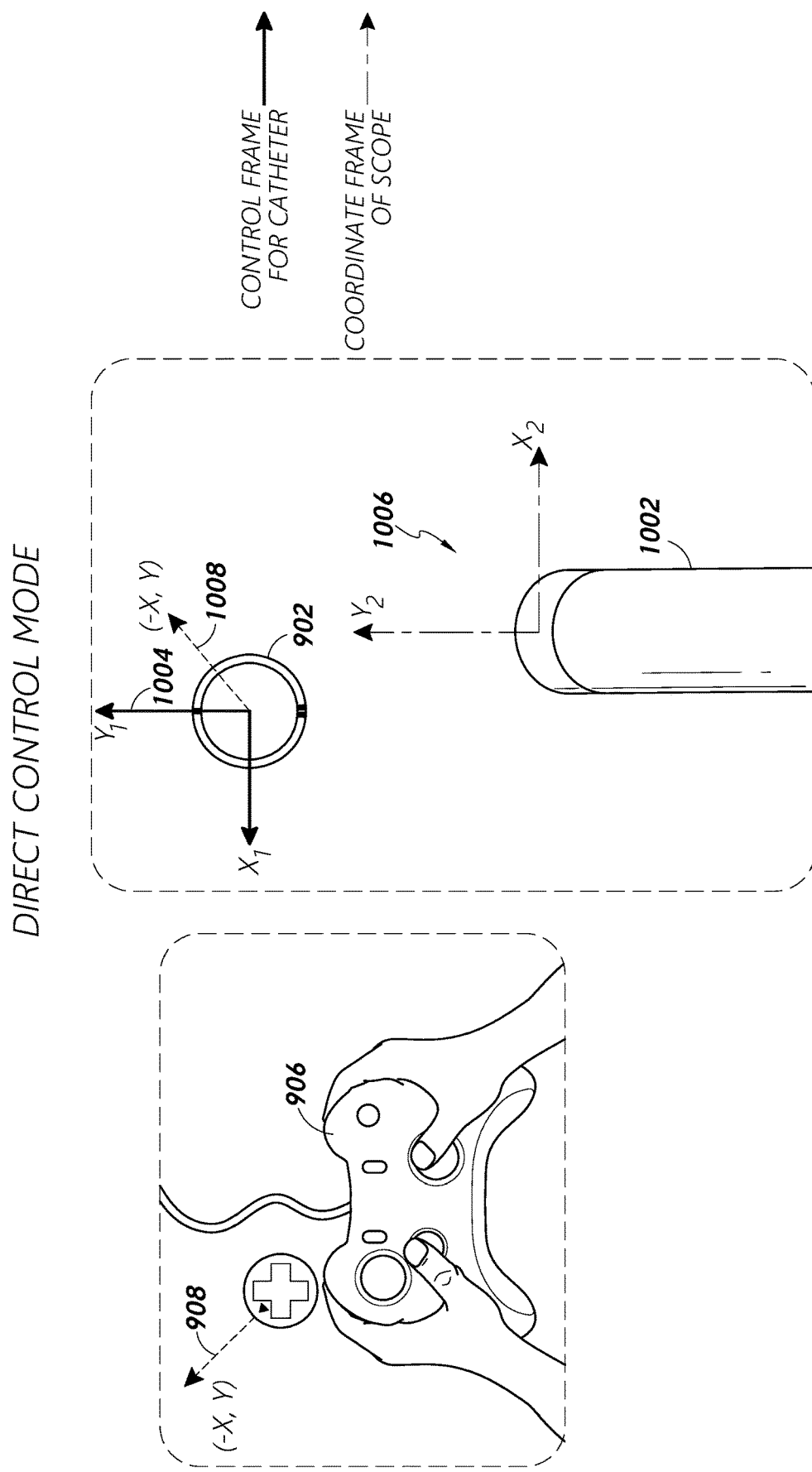
Figures 2, 10:
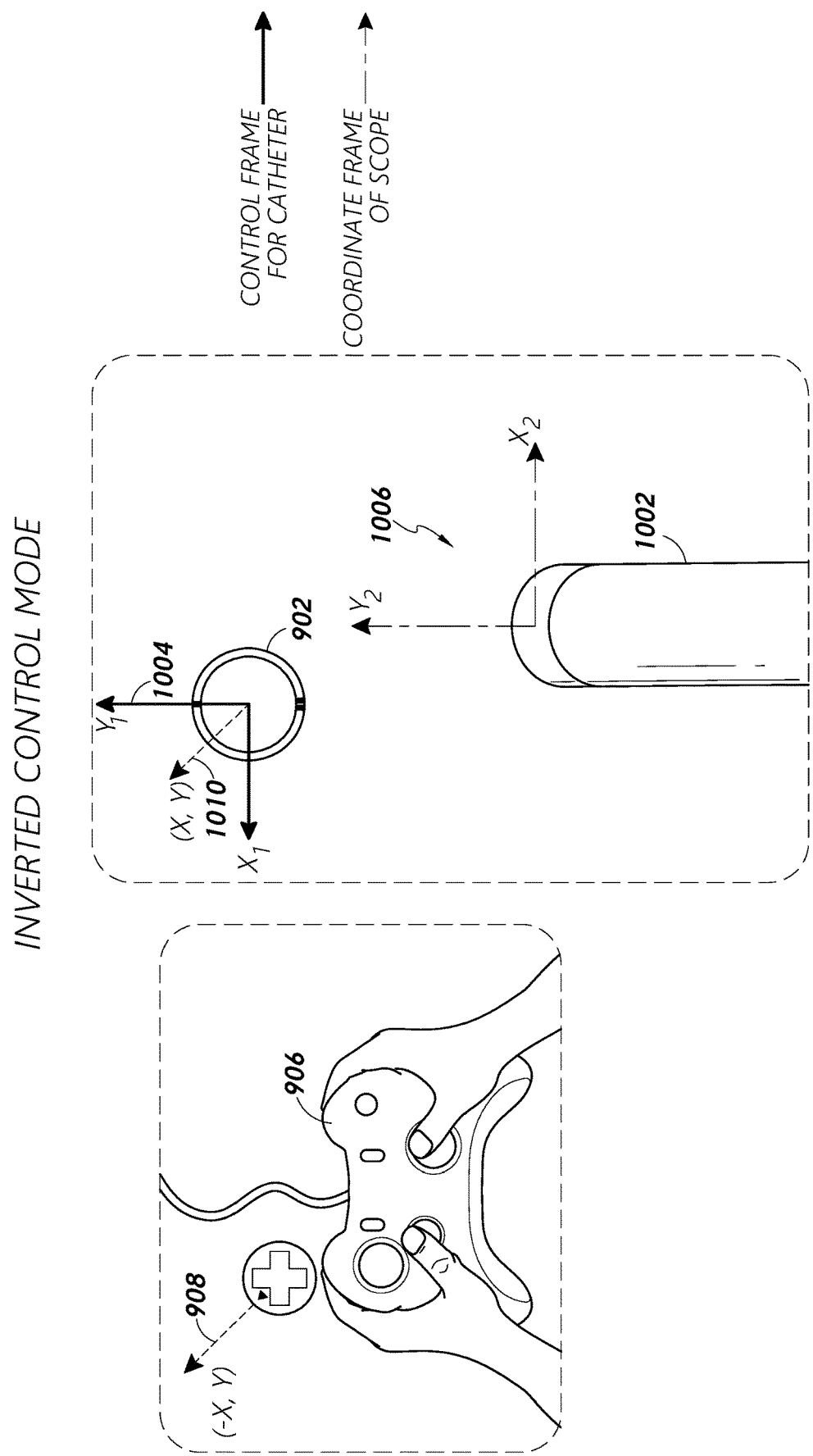

In some embodiments, such as in cases of third-person driving or other cases, a control frame of reference is implemented to facilitate movement of a medical instrument. FIGS. 10-1 and 10-2 illustrate example implementations of driving a medical instrument from a third-person perspective for different control modes with respect to a control frame for the medical instrument in accordance with one or more embodiments. In these figures, the catheter 902 from FIGS. 9-1 and 9-2 is oriented in a substantially head on manner with a scope 1002. For ease of illustration, the catheter 902 is illustrated with just a tip portion and not a body portion. FIGS. 10-1 and 10-2 illustrate the catheter 902 and the scope 1002 positioned in a manner that may occur during a medical procedure.

In FIGS. 10-1 and 10-2, the catheter 902 is controlled from a perspective of the scope 1002 with respect to a control frame 1004 (also referred to as "the control frame of reference 1004") associated with the catheter 902. The control frame 1004 can include an abstract coordinate frame/set of vectors that is used to control the catheter 902, such as an x-vector, y-vector, and z-vector. For ease of illustration, the z-vector for the control frame 1004 is not illustrated in FIGS. 10-1 and 10-2. The control frame 1004 can be correlated to an orientation of image data displayed through a user interface to drive the catheter 902. For example, the control frame 1004 can be representative of an orientation of image data captured from the scope 1002 as displayed within an interface (e.g., the positive y-axis of the control frame 1004 aligns with the y-axis of the interface). That is, the image data that is displayed through the interface depicts the catheter 902 in the orientation shown in FIGS. 10-1 and 10-2. The control frame 1004 can be aligned or offset by a number of degrees with respect to a coordinate frame of the catheter 902 (not illustrated in FIGS. 10-1 and 10-2). As noted above, a coordinate frame can be fixed with respect to an instrument (e.g., fixed to the markings on the catheter 902), while a control frame can change (e.g., rotate as the scope 1002 rolls and/or orientation of image data changes in the interface).

FIGS. 10-1 and 10-2 also illustrate a coordinate frame 1006 of the scope 1002, which is associated with a tip of the scope 1002. The coordinate frame 1006 can be correlated to an imaging device that is located on a tip of the scope 1002.

The catheter 902 can be controlled to move in different manners with respect to the control frame 1004 for different control modes. In the examples of FIGS. 10-1 and 10-2, input is received via the I/O device 906 that is associated with the direction/vector 908 relative to the I/O device 906, which has a negative x value (horizontal component) and a positive y value (vertical component). In a direct control mode (as shown in FIG. 10-1), the catheter 902 is controlled to move in a direction/vector 1008, which has a negative x value and a positive y value with respect to the control frame 1004. In contrast, for the same input, in an inverted control mode (as shown in FIG. 10-2), the catheter 902 is controlled to move in a direction/vector 1010, which has a positive x value and a positive y value with respect to the control frame 1004. Here, the direction 1010 is associated with an x value that has an opposite sign to the x value of the direction 908 (and opposite sign to the x value of the direction 1008 from FIG. 10-1). As such, a horizontal component can be inverted for the inverted control mode.

In some embodiments, to determine how to control the catheter 902 with respect to the control frame 1004, the vector 1008 can be determined for the control frame 1004 based on the vector 908. For example, a direction/magnitude of the vector 1008 can be determined based on a direction/magnitude of the vector 908. In instances where the inverted control mode is implemented, the direction of the vector 1008 can be determined by inverting a horizontal/vertical component (e.g., switch the sign of the x component of the vector 908). In some embodiments, the vector 908 is indirectly (or directly, in some cases) mapped/translated to a coordinate frame and/or control frame for the catheter 902 using one or more algorithms.

As noted above, input received via the I/O device 906 for the catheter 902 can drive articulation of the catheter 902, such as a rate of articulation of the catheter 902. For example, if input is received via an input component on the I/O device 906 (e.g., joystick), the catheter 902 will be articulated. If the input component is then left untouched, the catheter 902 can maintain its current position/orientation (e.g., stay put in its current articulated position). As such, input on the I/O device 906 can cause the catheter 902 to be controlled by adding/subtracting to existing articulation of the catheter 902.

Although the inverted control modes of the examples from FIGS. 9-1, 9-2, 10-1, and 10-2 are discussed in the context of inverting horizontal components (e.g., x values), an inverted control mode can alternatively, or additionally, cause vertical components to be changed (e.g., change a sign associated with a y value) and/or a component associated with insertion/retraction (e.g., change a sign associated with a z value).

Example Calibration Interface

Figure 11:
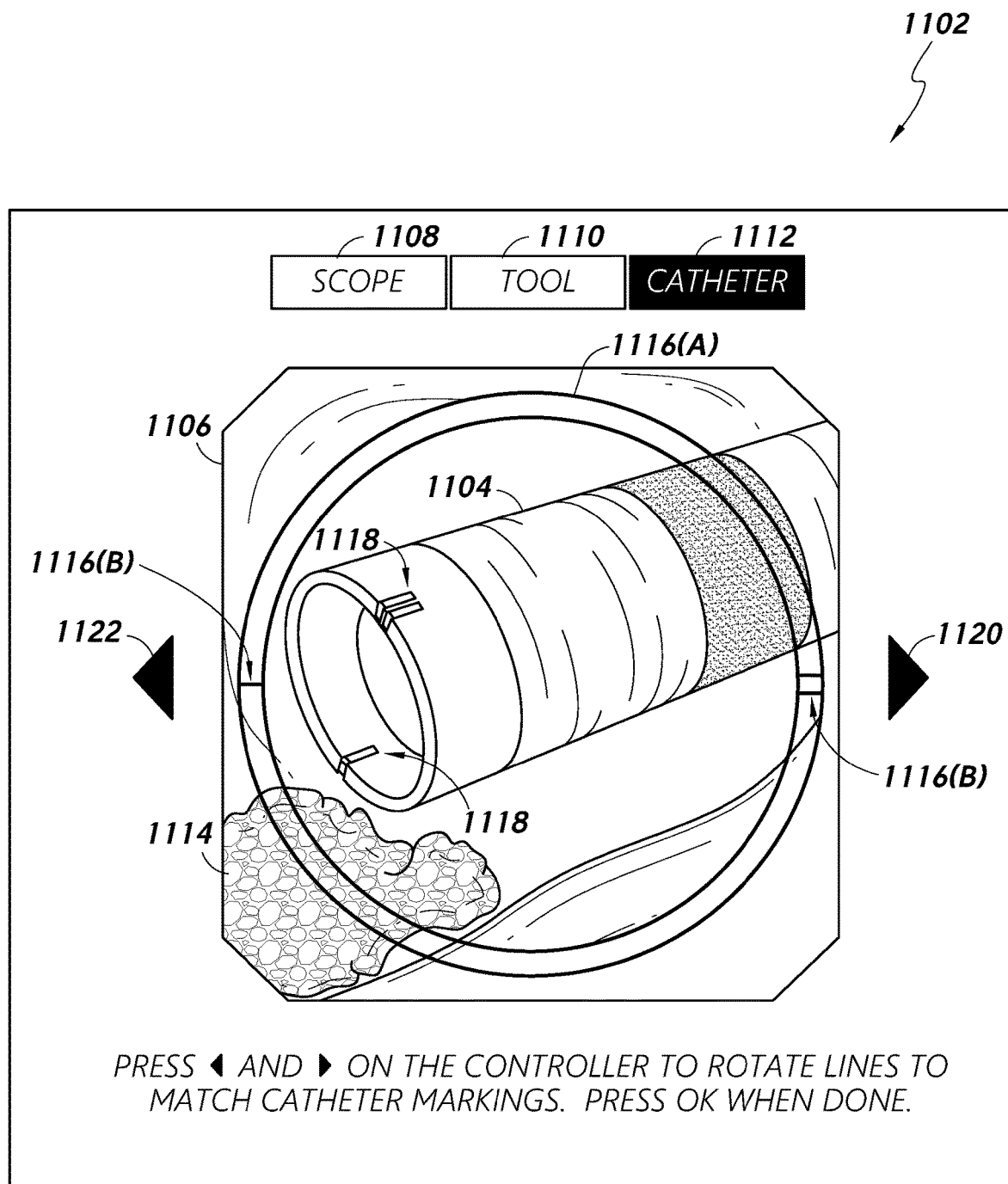
FIGS. 11-12 illustrates an example interface to calibrate a control scheme for a medical instrument in accordance with one or more embodiments.
Figure 12:
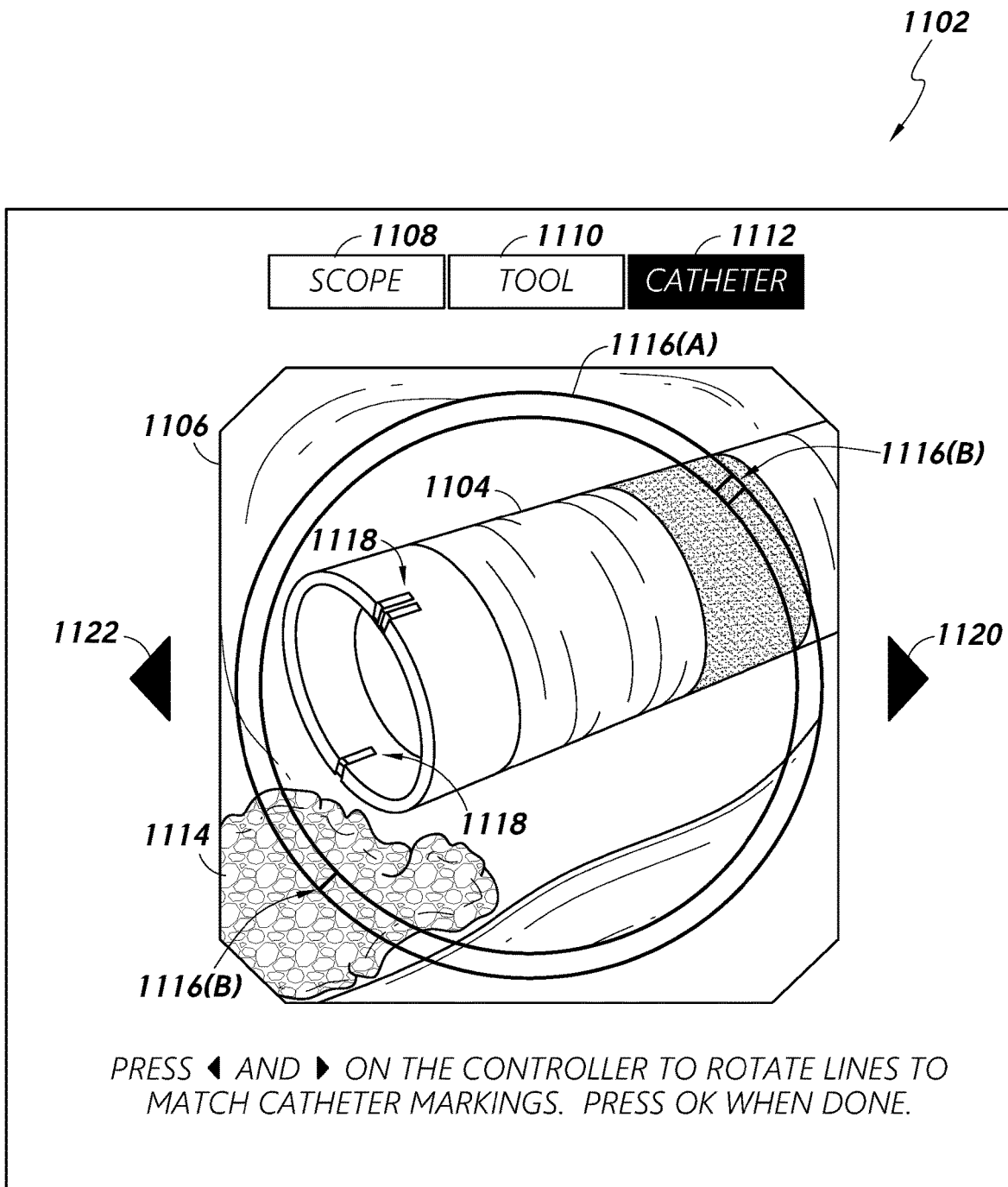

FIGS. 11-12 illustrates an example interface 1102 to calibrate a control scheme for a medical instrument in accordance with one or more embodiments. For example, the interface 1102 can provide information to adjust orientation information regarding of a distal end of a scope relative to a distal end of a catheter 1104. In some embodiments, a user can navigate to the interface 1102 when the user notices that movement of a medical instrument does not completely correlate to input provided via an input device. For example, if the user is driving the catheter 1104 from a perspective of the scope and notices that the catheter 1104 moves to the right in an instrument-driving interface (e.g., the interface 702 of FIG. 7) when up input is provided via an input device, the user can navigate to the interface 1102 to calibrate the catheter 1104 and/or the scope. However, the interface 1102 can be accessed at other times and/or in different manners.

As shown, the interface 1102 can present image data 1106 from a perspective of the scope that is within proximity to the catheter 1104. That is, the image data 1106 can depict at least a portion of a field-of-view of an imaging device on the scope. The image data 1106 can be presented in an original image view or a rotated image view. Although the interface 1102 generally presents image data from the perspective of the scope, the interface 1102 can additionally, or alternatively present image data from the perspective of another medical instrument.

The interface 1102 can also present interface elements 1108, 1110, 1012 to select a medical instrument to calibrate/control. The interface element 1108 enables calibration/control of the scope, the interface element 1110 enables calibration/control of a medical instrument associated with the scope (also referred to as a "tool"), and the interface element 1112 enables calibration/control of the catheter 1104. In the example of FIG. 11, the interface element 1112 is selected so that the catheter 1104 can be calibrated. For example, a user can calibrate a control scheme/control frame of reference associated with the catheter 1104. However, the interface element 1108/interface element 1110 can alternatively be selected to calibrate the control scheme.

To calibrate a control scheme/control frame for the catheter 1102, the interface 1102 can provide an alignment indicator 1116 representing an orientation of a tip of the catheter 1104. For example, the alignment indicator 1116 can represent a coordinate frame for the catheter 1104 relative to a coordinate frame for the scope. The alignment indicator 1116 can include a ring 1116(A) and one or more marking indicators 1116(B) representing an estimated orientation of one or more markings 1118 located on the catheter 1104 relative to the scope. For example, a control system (not illustrated) can attempt to track a roll of the scope and a roll of the catheter 1104 relative to each other. Based on such information, the control system can present the marking indicators 1116(B) to indicate an estimated roll of the tip of the catheter 1104 relative to an estimated roll of a tip of the scope. The marking indicators 1116(B) can be positioned around the ring 1116(A) to indicate the estimated orientation of the markings 1118 on the tip of the catheter 1104.

If desired, a user can provide input to adjust the orientation of the alignment indicator 1116 to more closely match the orientation of the markings 1118 on the tip of the catheter 1104. For example, as shown in FIG. 11, the orientation of the marking indicators 1116(B) are not aligned with the markings 1118 on the catheter 1104. As such, the user can provide input to rotate the alignment indicator 1116 so that the marking indicators 1116(B) are more aligned with the orientation of the markings 1118 as displayed within the image data 1106, as shown in FIG. 12. The user can rotate the alignment indicator 1116 by any number of degrees to a position the user believes aligns with the markings 1118 on the catheter 1104.

The user can provide input via any type of input device to rotate the alignment indicator 1116. For example, the user can provide input via a right directional control on a controller (or on a touchscreen, etc.), which can be correlated to a right directional interface element 1120, to rotate the alignment indicator 1116 in a clockwise manner. Further, the user can provide input via a left directional control on a controller (or on a touchscreen, etc.), which can be correlated to a left directional interface element 1122, to rotate the alignment indicator 1116 in a counterclockwise manner. However, other manners of input and/or rotation can be implemented. When rotated, the user can provide input to indicate that the marking indicators 1116(B) are aligned with the markings 1118. The adjustment to the alignment indicator 1116 can be used to update/calibrate a control scheme/control frame of reference for the catheter 1104.

Although the orientation of the marking indicators 1116(B) are generally initially displayed based on an estimated orientation of the markings 1118 of the catheter 1104 (as shown in FIG. 11), the marking indicators 1116(B) can be displayed in another orientation. For example, the marking indicators 1116(B) can be displayed initially at a predetermined orientation, such as at a predetermined position around the ring 1116(A). In a similar fashion as that described above, a user can adjust the marking indicators 1116(B) to match the orientation of the markings 1118 on the catheter 1104. The control system can then use the designated orientation of the catheter 1104 relative to the scope to adjust/calibrate a control scheme/control frame of reference for the catheter 1104.

Further, although the alignment indicator 1116 is implemented in the context of FIGS. 11-12, other visual elements can additionally, or alternatively, be implemented. For example, a slider can be presented to enable a user to adjust an orientation of the catheter 1104 relative to the scope.

Example Flow Diagram—Instrument Calibration Process

Figure 13:
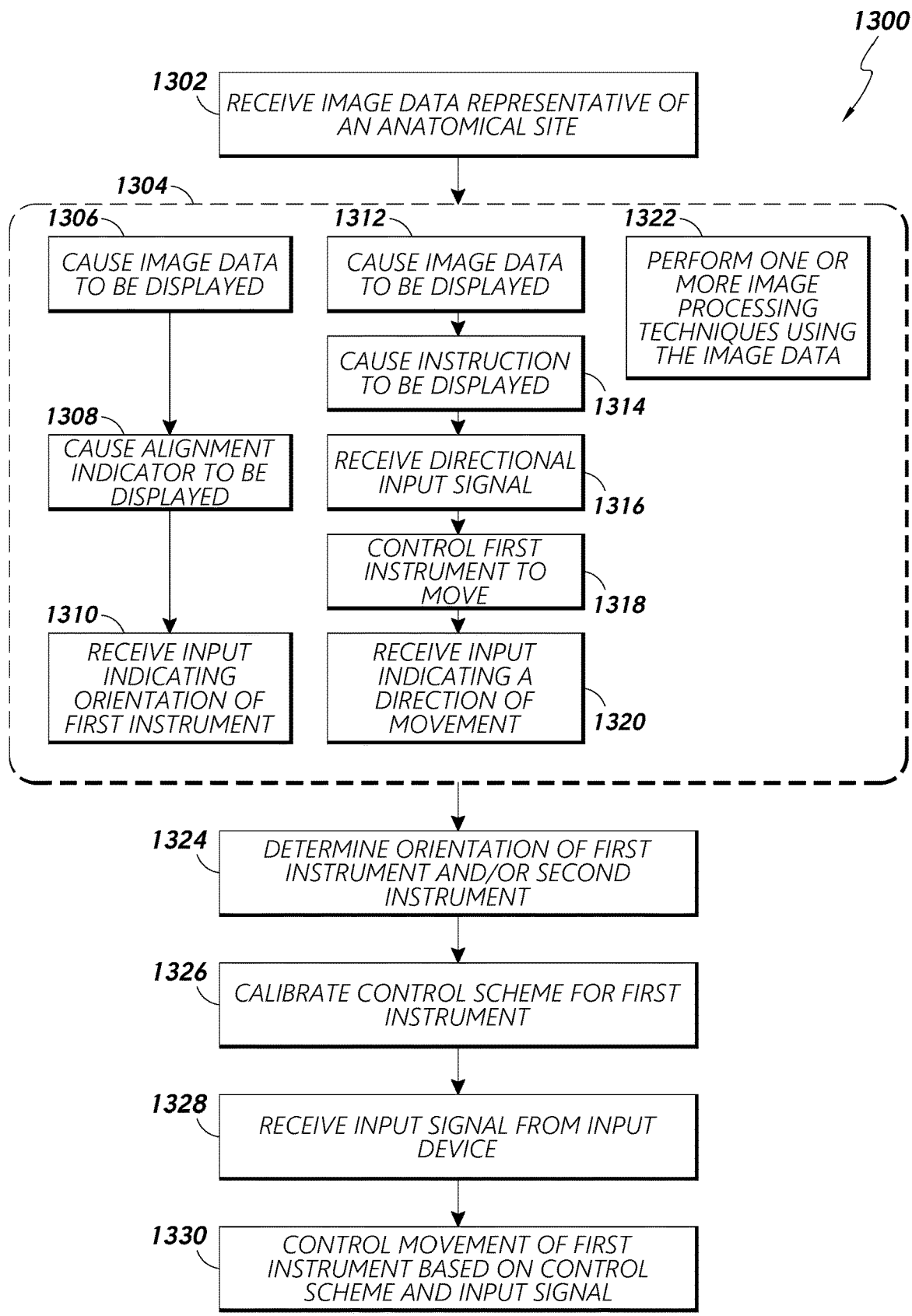
FIG. 13 illustrates an example flow diagram of a process for calibrating a control scheme/control frame of reference for a medical instrument in accordance with one or more embodiments.

FIG. 13 illustrates an example flow diagram of a process 1300 for calibrating a control scheme/control frame of reference for a medical instrument in accordance with one or more embodiments. The various operations associated with the process 1300 can be performed by control circuitry implemented in any of the devices/systems discussed herein or a combination thereof, such as the control system 150, the robotic system 110, the table 170, the scope 120, the catheter 130, and/or another device of FIG. 1.

At block 1302, the process 1300 can include receiving image data representative of an anatomical site. For example, a first instrument can be configured to access the anatomical site via a first access path and a second instrument can be configured to access the anatomical site via a second access path. The second instrument can generate the image data and send the image data to control circuitry. The control circuitry can receive the image data from the second instrument. The image data can be representative of the anatomical site and/or the first instrument. In some embodiments, the first instrument is a catheter and/or the second instrument is a scope.

At block 1304, the process 1300 can include performing one or more of blocks 1306-1322. For example, the control circuitry can perform one or more of blocks 1306-1322 in parallel, series, and so on.

At block 1306, the process 1300 can include causing the image data to be displayed. For example, the control circuitry can cause an image representation of the image data (received at block 1302) to be displayed via a user interface.

At block 1308, the process 1300 can include causing an alignment indicator to be displayed. For example, the control circuitry can cause the alignment indicator to be displayed via an interface, wherein the alignment indicator represents an orientation/first coordinate frame of the first instrument (e.g., relative to the second instrument). In some embodiments, the alignment indicator includes a ring and/or one or more marking indicators representing the orientation/first coordinate frame of the first instrument. In some embodiments, the alignment indicator represents an estimated roll of a distal end of the first instrument.

At block 1310, the process 1300 can include receiving input indicating an orientation of the first instrument, such as a roll of a distal end of the first instrument. For example, the control circuitry can receive input including an adjustment to the alignment indicator. The input can include rotating the alignment indicator to orient the one or more marking indicators of the alignment indicator with one or more markings on a distal end of the first instrument. Alternatively, or additionally, the control circuitry can receive other types of input that indicate an orientation of the first instrument, such as text/speech input indicating a degrees/angle of one or more markings on a tip of the first instrument as displayed via an interface.

At block 1312, the process 1300 can include causing the image data to be displayed. For example, the control circuitry can cause an image representation of the image data (received at block 1302) to be displayed via an interface.

At block 1314, the process 1300 can include causing an instruction to be displayed. The instruction can request that a user perform a particular action. In one example, the instruction indicates to select a particular directional control on an input device (e.g., text of "select the right direction" can be presented via an interface). In another example, the instruction indicates to move the first instrument in a particular direction with respect to an interface (e.g., text of "move the catheter to the right" can be displayed via an interface).

At block 1316, the process 1300 can include receiving a directional input signal. In one example, where a user is requested to select a particular directional control on the input device, the control circuitry can receive a directional input signal indicative of input received via the particular directional control. In another example, where a user is requested to move the first instrument in a particular direction with respect to the interface, the control circuitry can receive a directional input signal that causes the first instrument to move in the particular direction with respect to the interface. Here, a user may provide multiple inputs in an attempt to move the first instrument in the particular direction with respect to the interface.

At block 1318, the process 1300 can control the first instrument to move. For example, the control circuitry can cause the first instrument to move based at least in part on the directional input signal.

In some embodiments, such as in cases where the user is requested to select a particular directional control on the input device, at block 1320, the process 1300 can include receiving input indicating a direction of movement. For example, the control circuitry can receive input indicating a direction in which the first instrument moved in the interface in response to selecting the particular directional control on the input device. Here, the user can specify the direction in which the first instrument moved by providing input via an input device, such as through an interface, a controller, and so on.

At block 1322, the process 1300 can include performing one or more image processing techniques using the image data received at block 1302. For example, the control circuitry can perform one or more image processing techniques to identify the first instrument depicted in the image data. Such techniques can identify one or more features of the first instrument, such as a tip of the first instrument, one or more markings on the first instrument, and so on.

At block 1324, the process 1300 can include determining an orientation of the first instrument and/or an orientation of the second instrument. For example, the control circuitry can determine a first coordinate frame associated with the first instrument and/or a second coordinate frame associated with the second instrument based at least in part on one or more of blocks 1306-1322. A coordinate frame can indicate/represent a roll of a distal end of an instrument. In some embodiments, the control circuitry can generate roll data indicating a roll of a distal end of the first instrument relative to a roll of a distal end of the second instrument. For example, the roll data can indicate an orientation of a coordinate frame associated with the first instrument relative to a coordinate frame associated with the second instrument.

At block 1326, the process 1300 can include calibrating a control scheme for the first instrument. For example, the control scheme can include and/or be represented with a control frame of reference for the first instrument. The control circuitry can identify a difference between the first coordinate frame associate with the first instrument and the second coordinate frame associated with the second instrument and update the control frame of reference associated with the first instrument based on the difference.

At block 1328, the process 1300 can include receiving an input signal from an input device. For example, the control circuitry can receive a directional input signal from an input device indicating a direction of movement for the first instrument relative to the input device.

At block 1330, the process 1300 can include controlling movement of the first instrument based on the control scheme and the input signal. For example, the control circuitry can use the control scheme calibrated at block 1326 to control movement of the first instrument based on the input signal received at block 1328.

Example Control Frame Calibration

Figures 2, 14:
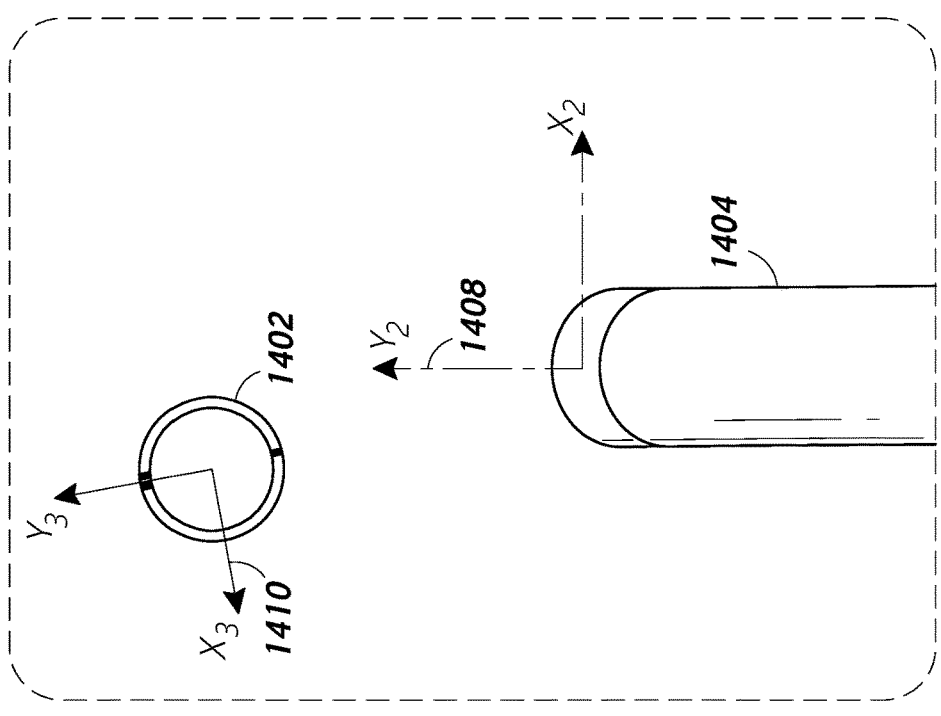
Figures 1, 14:
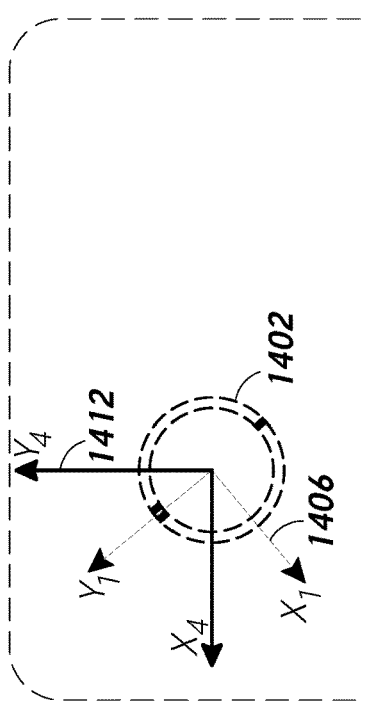
Figures 4, 14:
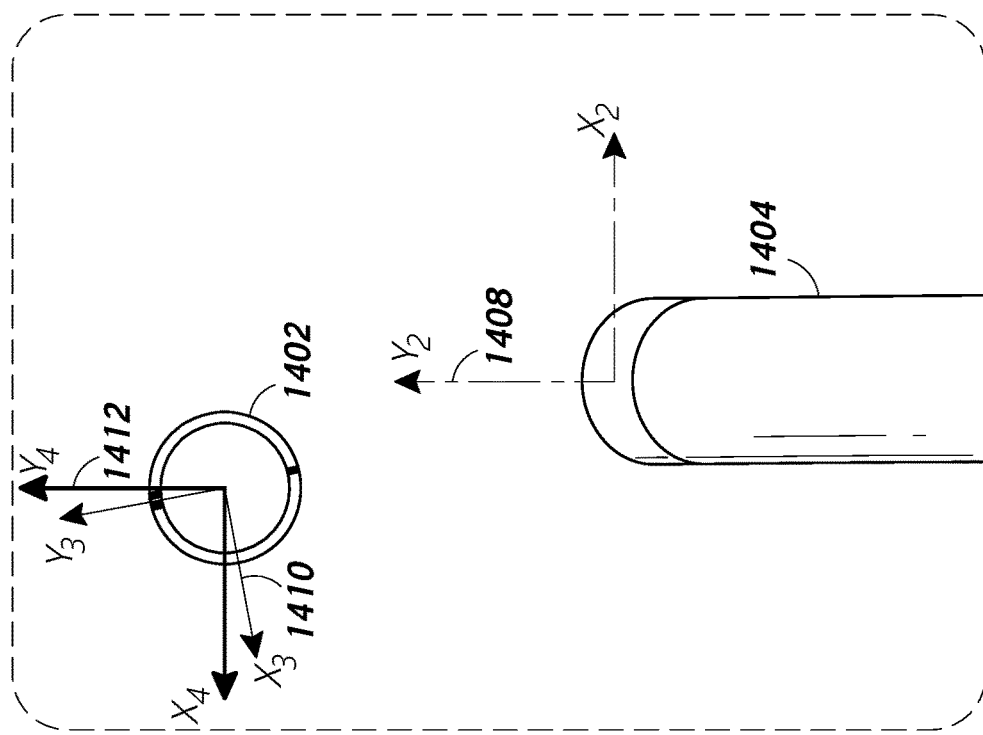
Figures 3, 14:
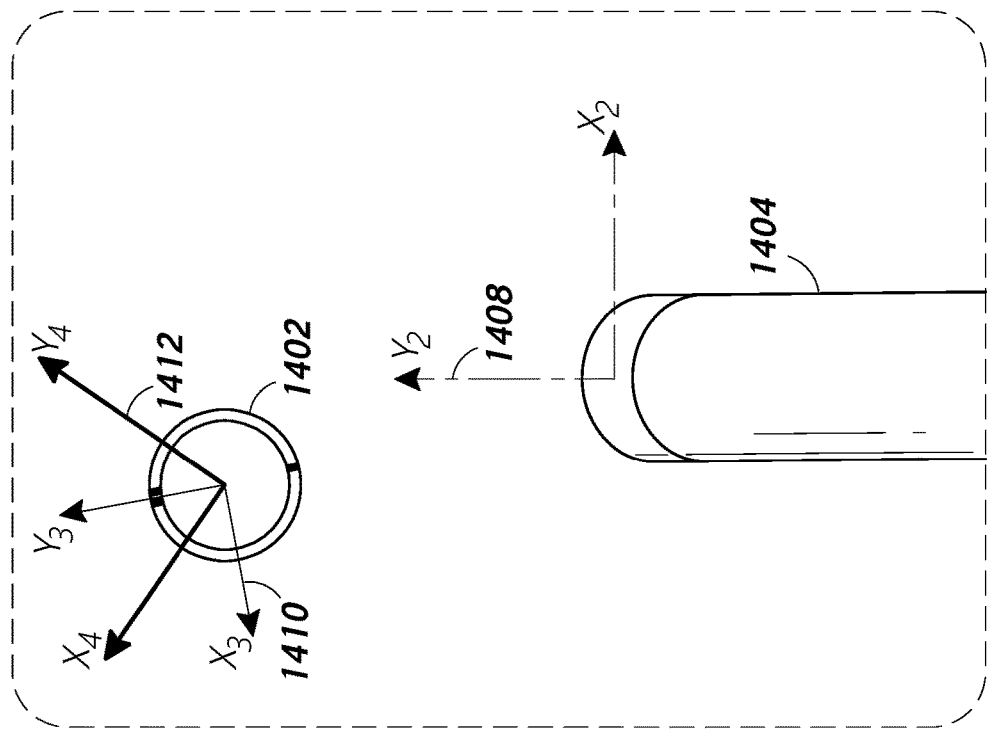

FIGS. 14-1 through 14-4 illustrate an example implementation of calibrating a control frame for a medical instrument in accordance with one or more embodiments. In these figures, a catheter 1402 is positioned within proximity to a scope 1404 to facilitate a medical procedure. Here, the catheter 1402 is oriented in a substantially head on manner with the scope 1404, with the catheter 1402 shown with just a tip portion and not a body portion. FIGS. 14-1 through 14-4 show various coordinate/control frames for the catheter 1402 and/or the scope 1404. Although various conventions can be used, the description will often refer to the "forward" direction as corresponding to positive z, the "right" direction as corresponding to positive x, and the "up" direction as corresponding to positive y. For ease of illustration, the z-vectors for the coordinate/control frames are not shown in FIGS. 14-1 through 14-4.

FIG. 14-1 illustrates an estimated orientation of the catheter 1402 relative to the scope 1404. In particular, FIG. 14-1 shows an estimated coordinate frame 1406 associated with the catheter 1402 relative to a coordinate frame 1408 associated with the scope 1404. Meanwhile, FIG. 14-2 shows an actual orientation of the catheter 1402 relative to the scope 1404, namely an actual coordinate frame 1410 of the catheter 1402 relative to the coordinate frame 1408 of the scope 1404. In this example, the estimated orientation of the catheter 1402 relative to the scope 1404 (as shown in FIG. 14-1) includes some amount of error with respect to the actual orientation of the catheter 1404 relative to the scope 1404 (as shown in FIG. 14-2). For example, the coordinate frames 1406 and 1410 are offset from each other. As noted above, such error can be due to undetected roll of the scope 1404, manipulation of a proximal end the scope 1404 that does not fully propagate to a distal end of the scope 1404, or other unaccounted for roll of the scope 1404.

FIG. 14-1 also shows a control frame 1412 for the catheter 1402 that is set based on the estimated orientation of the catheter 1402 relative to the scope 1404. The control frame 1412 can be implemented to control movement of the catheter 1402 from the perspective of the scope 1404. The control frame 1412 is represented/defined by an offset with respect to the estimated coordinate frame 1406 of the catheter 1402. However, when the control frame 1412 is implemented with the actual orientation of the catheter 1402, the control frame 1412 appears as shown in FIG. 14-3. As illustrated, the offset of the control frame 1412 with respect to the estimated coordinate frame 1406 of the catheter 1406 (FIG. 14-2) is the same as the offset of the control frame 1412 with respect to the actual coordinate frame 1410 of the catheter 1402 (FIG. 14-3).

Since the control frame 1412 is set based on the estimated orientation of the catheter 1402 relative to the scope 1404, and the estimated orientation has error, the control frame 1412 inaccurately represents a frame of reference for controlling the catheter 1402, as shown in FIG. 14-3. For example, if directional control input is received from an input device to move the catheter 1402 directly up, the catheter 1402 will be controlled to move up with respect to the control frame 1410 (i.e., in a positive direction along the y-axis of the control frame 1412). In the context of FIG. 14-3, which shows the actual orientation of the catheter 1402 relative to the scope 1404, the catheter 1402 will move up and to the right, instead of directly up. As such, the catheter 1402 will be controlled to move in an inaccurate manner with respect to the scope 1404.

To address the discrepancy between the estimated orientation and the actual orientation of the catheter 1402 relative to the scope 1404, the control frame 1412 for the catheter 1402 can be calibrated. For example, the control frame 1412 can be adjusted to accurately reflect the orientation of the catheter 1402 relative to the scope 1404, as shown in FIG. 14-4. In some embodiments, the estimated coordinate frame 1406 of the catheter 1402 and the coordinate frame 1408 of the scope 1404 can be translated into the same plane. A first offset/difference between the coordinate frames 1406 and 1408 can then be determined (e.g., an offset of between an x/y axis of the coordinate frame 1406 and an x/y axis of the coordinate frame 1408). Additionally, a determined coordinate frame for the catheter 1402 (e.g., determined through user adjustment to an alignment indicator on an interface, determined through image processing, etc.) and the coordinate frame 1408 of the scope 1404 can be translated into the same plane. A second offset/difference between the determined coordinate frame for the catheter 1402 and the coordinate frame 1408 for the scope 1404 can be determined. A difference between the first offset and the second offset can be determined and used to update the control frame 1412. For example, if there is a difference of 15 degrees between the first offset and the second offset (e.g., meaning that the estimated orientation of the catheter 1402 relative to the scope 1404 is inaccurate by 15 degrees), the control frame 1412 can be adjusted by 15 degrees or some amount based on the 15 degrees.

Example Procedure Using a Medical System

FIGS. 15-18 illustrate a top view the medical system 100 of FIG. 1 arranged to perform a percutaneous procedure in accordance with one or more embodiments. In these examples, the medical system 100 is arranged in an operating room to remove a kidney stone from the patient 140 with the assistance of the scope 120 (e.g., ureteroscope) and the catheter 130. In many embodiments of such procedure, the patient 140 is positioned in a modified supine position with the patient 140 slightly tilted to the side to access the back or side of the patient 140, such as that illustrated in FIG. 1. However, the patient 140 can be positioned in other manners, such as a supine position, a prone position, and so on. For ease of illustration, the imaging device 180 (including the C-arm) has been removed.

Although FIGS. 15-18 illustrate use of the medical system 100 to perform a percutaneous procedure to remove a kidney stone from the patient 140, the medical system 100 can be used to remove a kidney stone in other manners and/or to perform other procedures. Further, the patient 140 can be arranged in other positions as desired for a procedure. Various acts are described in FIGS. 15-18 and throughout this disclosure as being performed by the physician 160. It should be understood that these acts can be performed directly by the physician 160, a user under direction of the physician, another user (e.g., a technician), a combination thereof, and/or any other user.

The renal anatomy, as illustrated at least in part in FIGS. 15-18, is described here for reference with respect to certain medical procedures relating to aspects of the present concepts. The kidneys generally comprise two bean-shaped organs located on the left and right in the retroperitoneal space. In adult humans, the kidneys are generally about 11 cm in length. The kidneys receive blood from the paired renal arteries; blood exits into the paired renal veins. Each kidney is attached to a ureter, which is a tube that carries excreted urine from the kidney to the bladder. The bladder is attached to the urethra.

The kidneys are typically located relatively high in the abdominal cavity and lie in a retroperitoneal position at a slightly oblique angle. The asymmetry within the abdominal cavity, caused by the position of the liver, typically results in the right kidney being slightly lower and smaller than the left, and being placed slightly more to the middle than the left kidney. On top of each kidney is an adrenal gland. The upper parts of the kidneys are partially protected by the 11th and 12th ribs. Each kidney, with its adrenal gland is surrounded by two layers of fat: the perirenal fat present between renal fascia and renal capsule and pararenal fat superior to the renal fascia.

The kidney participates in the control of the volume of various body fluid compartments, fluid osmolality, acid-base balance, various electrolyte concentrations, and removal of toxins. The kidneys provide filtration functionality by secreting certain substances and reabsorbing others. Examples of substances secreted into the urine are hydrogen, ammonium, potassium, and uric acid. In addition, the kidneys also carry out various other functions, such as hormone synthesis, and others.

A recessed area on the concave border of the kidney is the renal hilum, where the renal artery enters the kidney and the renal vein and ureter leave. The kidney is surrounded by tough fibrous tissue, the renal capsule, which is itself surrounded by perirenal fat, renal fascia, and pararenal fat. The anterior (front) surface of these tissues is the peritoneum, while the posterior (rear) surface is the transversalis fascia.

The functional substance, or parenchyma, of the kidney is divided into two major structures: the outer renal cortex and the inner renal medulla. These structures take the shape of a plurality of cone-shaped renal lobes, each containing renal cortex surrounding a portion of medulla called a renal pyramid. Between the renal pyramids are projections of cortex called renal columns. Nephrons, the urine-producing functional structures of the kidney, span the cortex and medulla. The initial filtering portion of a nephron is the renal corpuscle, which is located in the cortex. This is followed by a renal tubule that passes from the cortex deep into the medullary pyramids. Part of the renal cortex, a medullary ray is a collection of renal tubules that drain into a single collecting duct.

The tip, or papilla, of each pyramid empties urine into a respective minor calyx; minor calyces empty into major calyces, and major calyces empty into the renal pelvis, which transitions to the ureter. At the hilum, the ureter and renal vein exit the kidney and the renal artery enters. Hilar fat and lymphatic tissue with lymph nodes surrounds these structures. The hilar fat is contiguous with a fat-filled cavity called the renal sinus. The renal sinus collectively contains the renal pelvis and calyces and separates these structures from the renal medullary tissue.

FIGS. 15-18 show various features of the anatomy of the patient 140. For example, the patient 140 includes kidneys 1502 fluidly connected to a bladder 1504 via ureters 1506, and a urethra 1508 fluidly connected to the bladder 1504. As shown in the enlarged depiction of the kidney 1502(A), the kidney 1502(A) includes calyces (including calyx 1510), renal papillae (including the renal papilla 1512, also referred to as "the papilla 1512"), and renal pyramids (including the renal pyramid 1514). In these examples, a kidney stone 1516 is located in proximity to the papilla 1512. However, the kidney stone 1516 can be located at other locations within the kidney 1502(A) or elsewhere.

Figure 15:
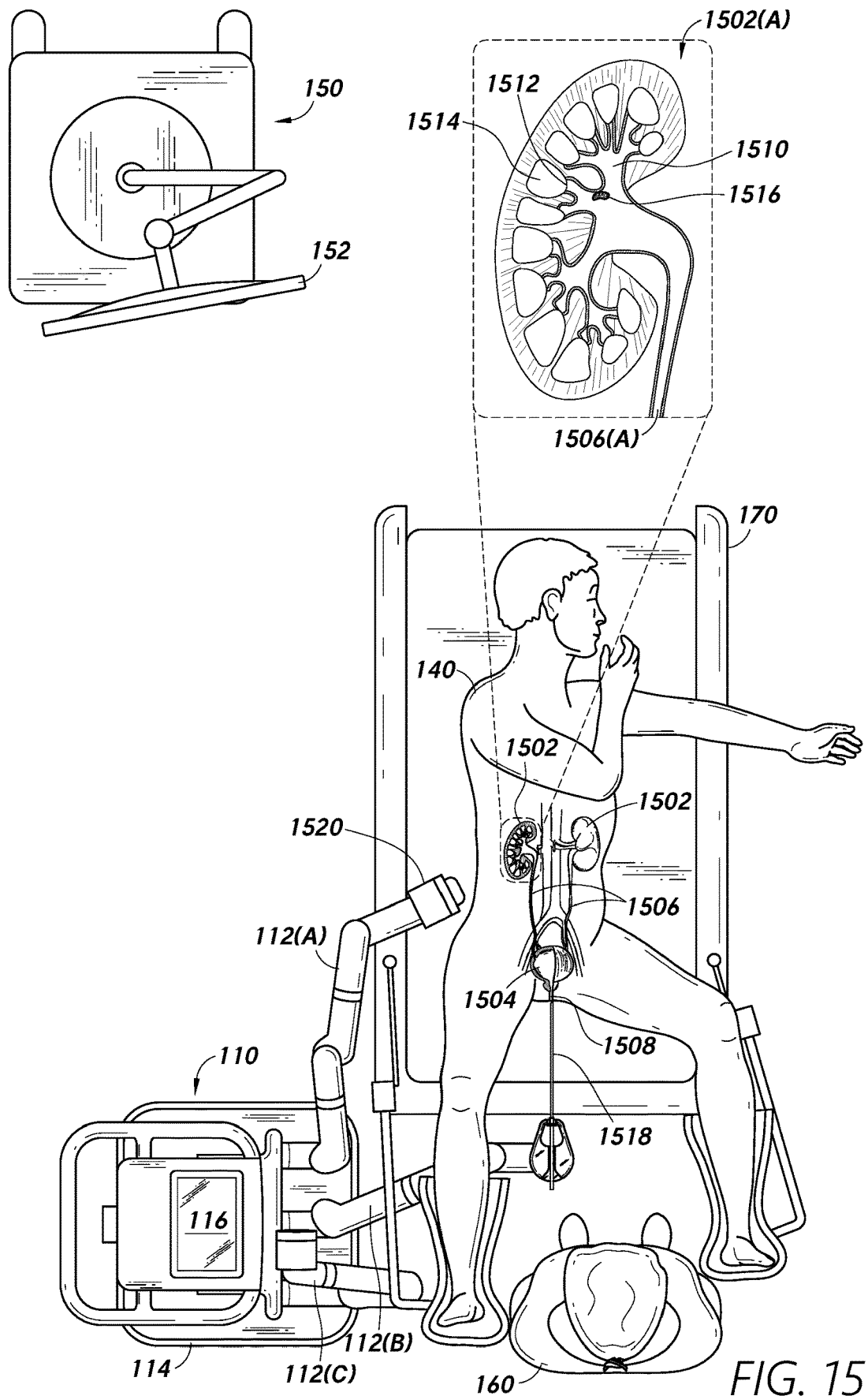
FIG. 15 illustrates a top of the medical system of FIG. 1 arranged to assist in inserting a scope into a patient in accordance with one or more embodiments.

As shown in FIG. 15, to remove the kidney stone 1516 in the example percutaneous procedure, the physician 160 can position the robotic system 110 at the side/foot of the table 170 to initiate delivery of the scope 120 (not illustrated in FIG. 15) into the patient 140. In particular, the robotic system 110 can be positioned at the side of the table 170 within proximity to the feet of the patient 140 and aligned for direct linear access to the urethra 1508 of the patient 140. In examples, the hip of the patient 140 is used as a reference point to position the robotic system 110. Once positioned, one or more of the robotic arms 112, such as the robotic arms 112(B) and 112(C), can stretch outwards to reach in between the legs of the patient 140. For example, the robotic arm 112(B) can be controlled to extend and provide linear access to the urethra 1508, as shown in FIG. 15. In this example, the physician 160 inserts a medical instrument 1518 at least partially into the urethra 1508 along this direct linear access path (sometimes referred to as "a virtual rail"). The medical instrument 1518 can include a lumen-type device configured to receive the scope 120, thereby assisting in inserting the scope 120 into the anatomy of the patient 140. By aligning the robotic arm 112(B) to the urethra 1508 of the patient 140 and/or using the medical instrument 1518, friction and/or forces on the sensitive anatomy in the area can be reduced. Although the medical instrument 1518 is illustrated in FIG. 15, in some embodiments, the medical instrument 1518 is not used (e.g., the scope 120 can be inserted directly into the urethra 1508).

The physician 160 can also position the robotic arm 112(A) near a treatment site for the procedure. For example, the robotic arm 112(A) can be positioned within proximity to the incision site and/or the kidneys 310 of the patient 140. The robotic arm 112(A) can be connected to an EM field generator 1520 to assist in tracking a location of the scope 120 and/or other instruments during the procedure. Although the robotic arm 112(A) is positioned relatively close to the patient 140, in some embodiments the robotic arm 112(A) is positioned elsewhere and/or the EM field generator 1520 is integrated into the table 170 (which can allow the robotic arm 112(A) to be in a docked position). In this example, at this point in the procedure, the robotic arm 112(C) remains in a docked position, as shown in FIG. 15. However, the robotic arm 112(C) can be used in some embodiments to perform any of the functions discussed above of the robotic arms 112(A) and/or 112(C).

Figure 16:
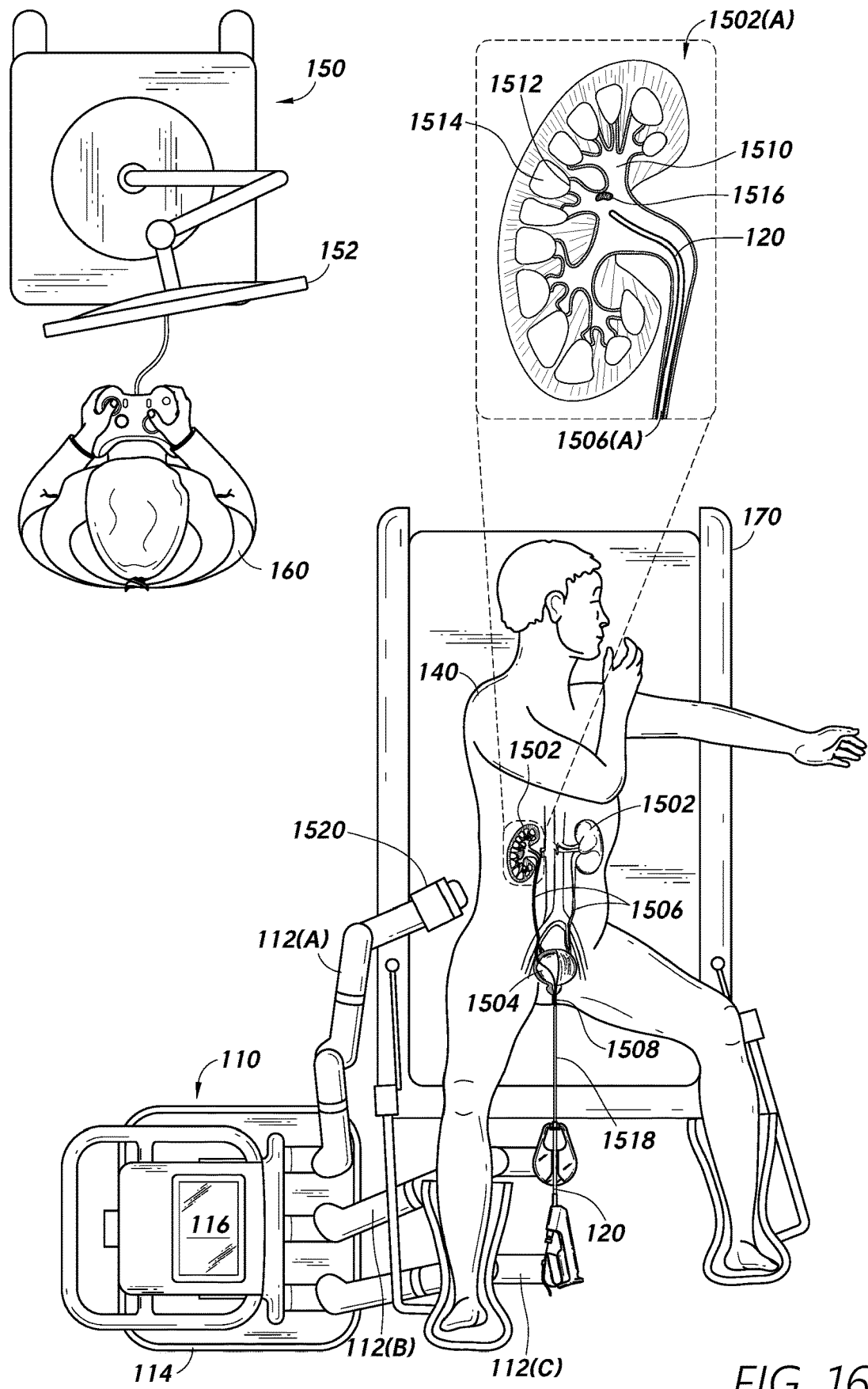
FIG. 16 illustrates a top of the medical system of FIG. 1 arranged to navigate a scope within a patient in accordance with one or more embodiments.

Once the robotic system 110 is properly positioned and/or the medical instrument 1518 is inserted at least partially into the urethra 1518, the scope 120 can be inserted into the patient 140 robotically, manually, or a combination thereof, as shown in FIG. 16. For example, the physician 160 can connect the scope 120 to the robotic arm 112(C) and/or position the scope 120 at least partially within the medical instrument 1518 and/or the patient 140. The scope 120 can be connected to the robotic arm 112(C) at any time, such as before the procedure or during the procedure (e.g., after positioning the robotic system 110). The physician 160 can then interact with the control system 150, such as the I/O device(s) 156, to navigate the scope 120 within the patient 140. For example, the physician 160 can provide input via the I/O device(s) 156 to control the robotic arm 112(C) to navigate the scope 120 through the urethra 1508, the bladder 1504, the ureter 1506(A), and up to the kidney 1502(A).

In some embodiments, the control system 150 can present an interface (not illustrated) via the display(s) 152 to view a real-time image(s) captured by the scope 120 to assist the physician 160 in controlling the scope 120. The physician 160 can navigate the scope 120 to locate the kidney stone 1516. In some embodiment, the control system 150 can use localization techniques to determine a position and/or an orientation of the scope 120, which can be viewed by the physician 160 through the display(s) 152 to also assist in controlling the scope 120. Further, in some embodiments, other types of information can be presented through the display(s) 152 to assist the physician 160 in controlling the scope 120, such as x-ray images of the internal anatomy of the patient 140.

Upon locating the kidney stone 1516, the physician 160 can identify a location for a needle 17022 to enter the kidney 1502(A) for eventual extraction of the kidney stone 1516. For example, to minimize bleeding and/or avoid hitting a blood vessel or other undesirable anatomy of the kidney 1502(A) and/or anatomy surrounding the kidney 1502(A), the physician 160 can seek to align the needle 17022 with an axis of a calyx (e.g., can seek to reach the calyx head-on through the center of the calyx). To do so, the physician 160 can identify a papilla as a target location. In this example, the physician 160 uses the scope 120 to locate the papilla 1512 that is near the kidney stone 1516 and designate the papilla 1512 as the target location. In some embodiments of designating the papilla 1512 as the target location, the physician 160 can navigate the scope 120 to contact the papilla 1512, the control system 150 can use localization techniques to determine a location of the scope 120 (e.g., a location of the end of the scope 120), and the control system 150 can associate the location of the scope 120 with the target location. In other embodiments, the physician 160 can navigate the scope 120 to be within a particular distance to the papilla 1512 (e.g., park in front of the papilla 1512) and provide input indicating that the target location is within a field-of-view of the scope 120. The control system 150 can perform image analysis and/or other localization techniques to determine a location of the target location. In yet other embodiments, the scope 120 can deliver a fiduciary to mark the papilla 1512 as the target location.

Figure 17:
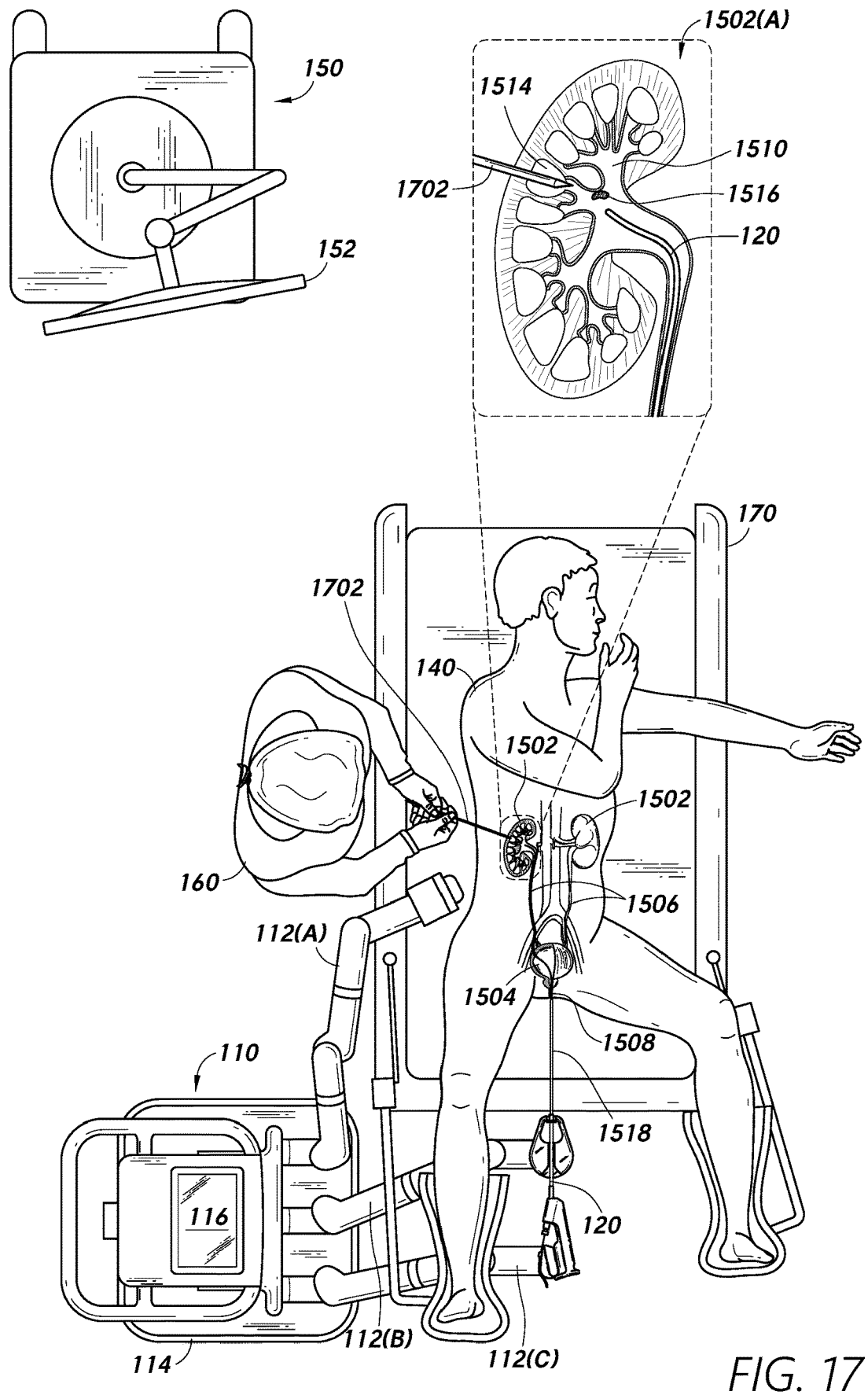
FIG. 17 illustrates a top of the medical system of FIG. 1 arranged to assist in inserting a needle into a patient in accordance with one or more embodiments.

As shown in FIG. 17, the physician 160 (and/or the robotic system 110) can proceed with the procedure by positioning the needle 1702 for insertion into the target location. In some embodiments, the physician 160 can use his or her best judgment to place the needle 1702 on the patient 140 at an incision site, such as based on knowledge regarding the anatomy of the patient 140, experience from previously performing the procedure, an analysis of CT/x-ray images or other pre-operative information of the patient 140, and so on. Further, in some embodiments, the control system 150 can provide information regarding a location to place the needle 1702 on the patient 140. The physician 160 can attempt to avoid critical anatomy of the patient 140, such as the lungs, pleura, colon, paraspinal muscles, ribs, intercostal nerves, etc. In some examples, the control system 150 can use CT/x-ray/ultrasound images to provide information regarding a location to place the needle 1702 on the patient 140. In some embodiments, the control system 150 can present information to assist the physician 160 in inserting the needle 1702. For example, the control system 150 can display an instrument alignment element indicative of an orientation of the needle 1702 relative to a target trajectory to assist the physician 160 and orienting the needle 1702 to the appropriate orientation (i.e., the target trajectory). Further, the control system 150 can display progress information indicative of a proximity of the needle 1702 to the target location.

Figure 18:
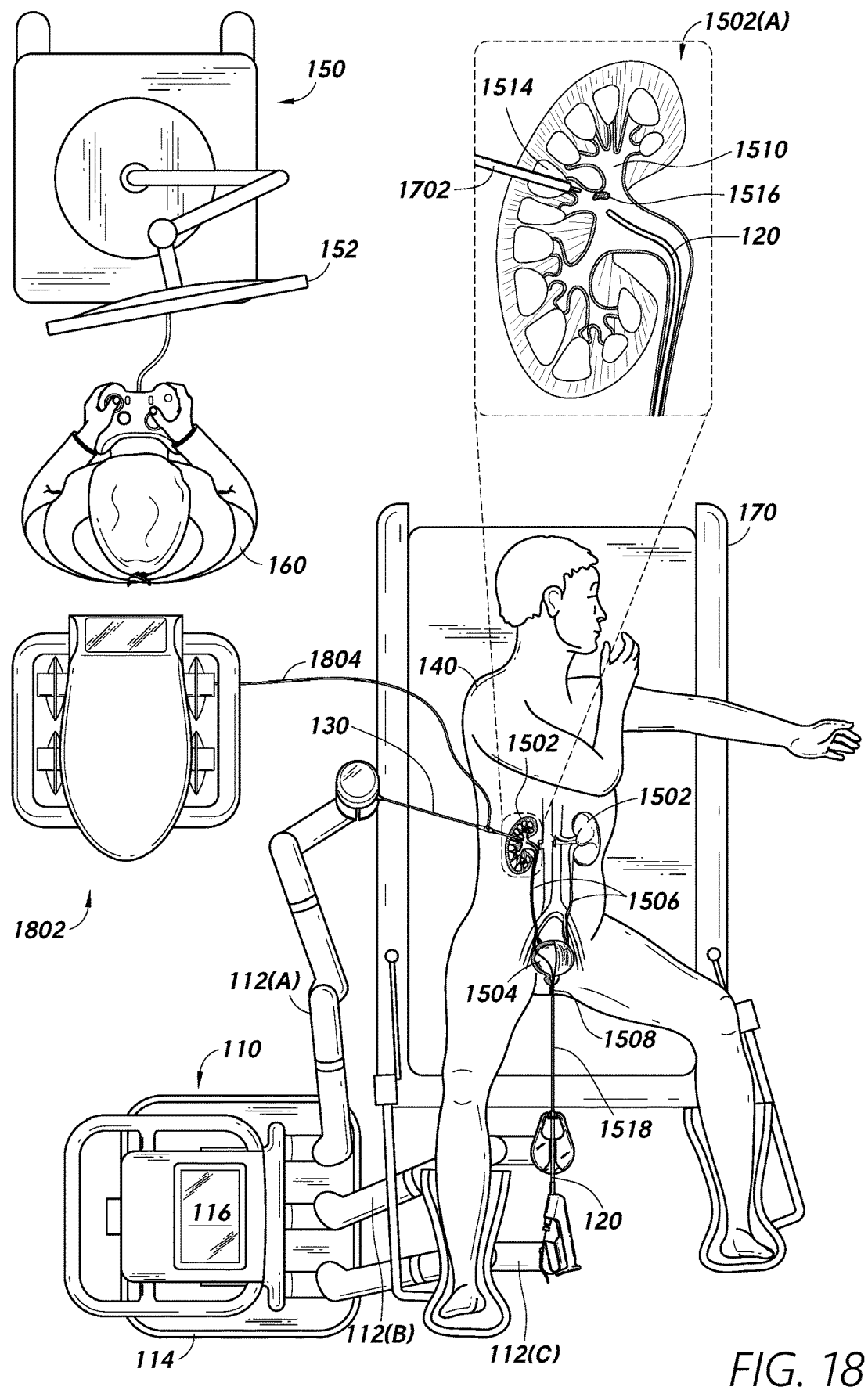
FIG. 18 illustrates a top of the medical system of FIG. 1 arranged to navigate a catheter within a patient in accordance with one or more embodiments.

As shown in FIG. 18, once the target location has been reached with the needle 1702, the physician 160 and/or the robotic system 110 can insert another medical instrument into the path created by the needle 1702. In this example, the EM field generator 1520 on the robotic arm 112(A) is replaced with the catheter 130, which is configured to be inserted into the percutaneous access path. The physician 160 can interact with the control system 150 (e.g., the I/O device(s) 156) to navigate the catheter 130 through the percutaneous access path to the target location. The control system 150 can provide information via the display(s) 152, such as any of the interfaces discussed herein, to assist the physician 160 in navigating the catheter 130. In examples, the catheter 130 may be driven from a third-person perspective (e.g., from the viewpoint of the scope 120). In some embodiments, the medical system 100 can facilitate one or more control/driving modes and/or calibration techniques to assist the physician 160 in driving and/or calibrating the catheter 130, the scope 120, and/or another medical instrument.

When the scope 120 and/or the catheter 130 are located at the appropriate position, the physician 160 can use the scope 120 to break up the kidney stone 1516 and/or use the catheter 130 to extract pieces of the kidney stone 1516 from the patient 140. For example, the scope 120 can deploy a tool (e.g., a laser, a cutting instrument, etc.) to fragment the kidney stone into pieces and the catheter 130 can suck out the pieces from the kidney 1502(A) through the percutaneous access path. The physician 160 can switch between controlling the scope 120 and the catheter 130, in some cases. For example, the physician 160 can use the same I/O device(s) 156 to control the catheter 130 and the scope 120. In examples, the I/O device(s) 156 includes a button to switch between controlling the medical instruments.

In some embodiments, the catheter 130 and/or the scope 120 can provide irrigation and/or aspiration to facilitate removal of the kidney stone 1516. For example, the catheter 130 and/or the scope 120 can be connected to an irrigation/aspiration system 1802. The irrigation/aspiration system 1802 can be configured to hold one or more fluid bags/containers and/or control fluid therefrom. For example, an irrigation line 1804 can be coupled to one or more of the bags/containers and to an irrigation port of the catheter 130. Irrigation fluid can be provided to the target anatomy via the irrigation line 1804 and the catheter 130. The irrigation/aspiration system 1802 can include certain electronic components, such as a display, flow control mechanics, and/or certain associated control circuitry. In some examples, the irrigation/aspiration system 1802 is implemented as a fluid management cart. In examples, the irrigation/aspiration system 1802 is configured to interface with other components of the medical system 100, such as the control system 150 the robotic system 110, and/or other components.

In some embodiments, such as the example discussed above in reference to FIG. 18, the EM field generator 1520 is removed from the robotic arm 112(A) while the catheter 130 is being driven. During such phase, one or more EM-based localization techniques may not be performed to determine a position/orientation of the scope 120. As such, the medical system 100 can, at times, lose track of the position/orientation of the scope 120 and/or another medical instrument. Thus, one or more of the techniques discussed herein may be implemented to calibrate the scope 120 and/or a control scheme for controlling the catheter 130 from a perspective of the scope 120.

Although particular robotic arms of the robotic system 110 are illustrated as performing particular functions in the context of FIGS. 15-18, any of the robotic arms 112 can be used to perform the functions. Further, any additional robotic arms and/or systems can be used to perform the procedure. Moreover, the robotic system 110 can be used to perform other parts of the procedure. In some embodiments, a percutaneous procedure can be performed entirely or partially with the medical system 100 (e.g., with or without the assistance of the physician 160).

Example Robotic System

Figure 19:
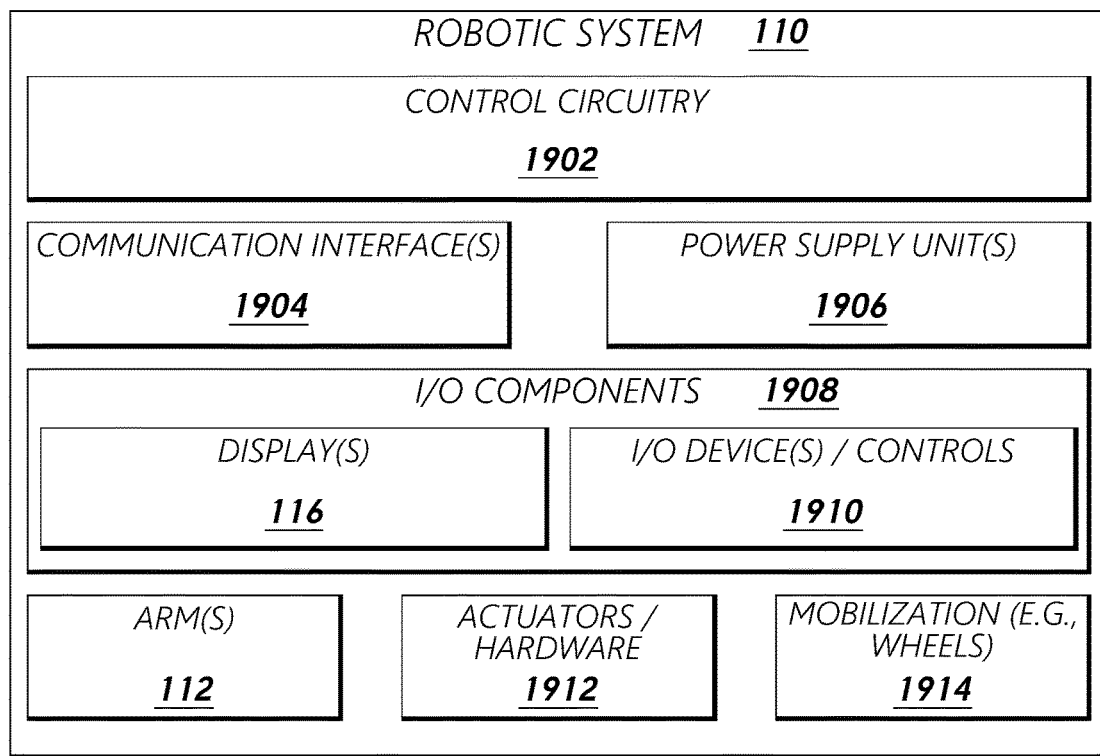
FIG. 19 illustrates example details of the robotic system of FIG. 1 in accordance with one or more embodiments.
Figure 19:
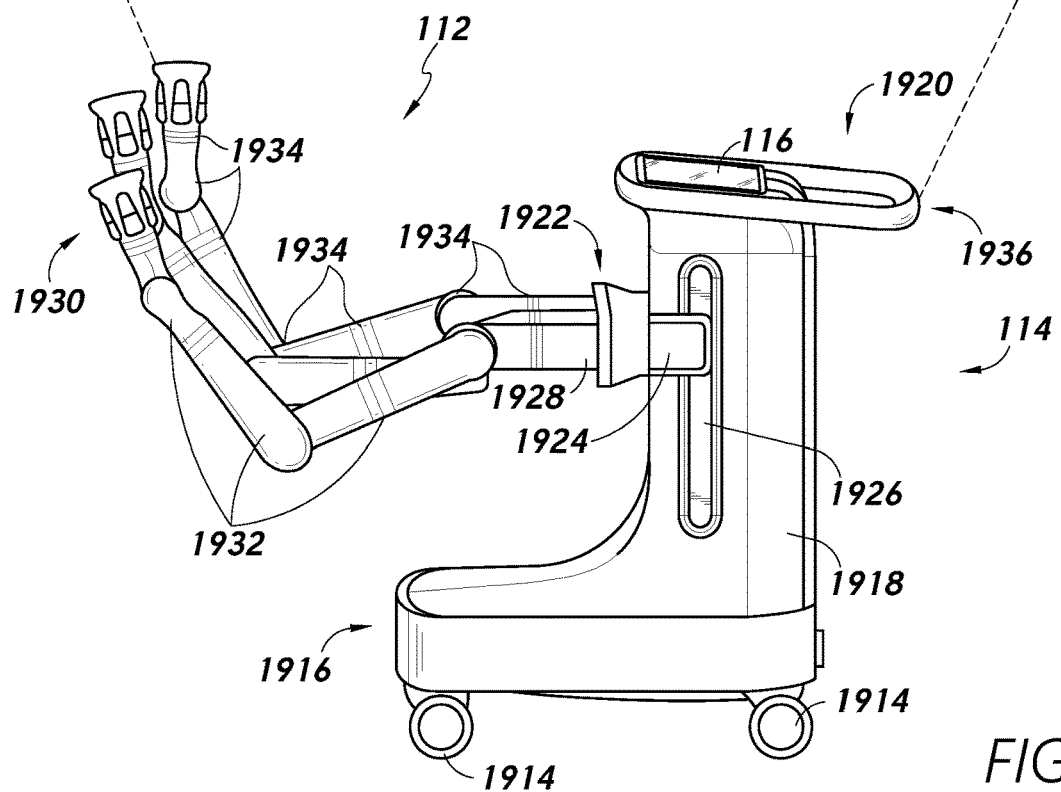

FIG. 19 illustrates example details of the robotic system 110 of FIG. 1 in accordance with one or more embodiments. As shown, the robotic system 110 can include control circuitry 1902, a communication interface(s) 1904 (e.g., configured to communicate with one or more components/devices), a power supply unit(s) 1906 (e.g., configured to supply/manage power to components of the robotic system 110), I/O components 1908 (e.g., the display(s) 116 and/or other I/O devices/controls 1910), the one or more robotic arms 112, actuators/hardware 1912, and/or mobilization component(s) 1914 (e.g., wheels). In some embodiments, the robotic system 110 can comprise a housing/enclosure configured and/or dimensioned to house or contain at least part of one or more of the components of the robotic system 110. In this example, the robotic system 110 is illustrated as a cart-based system that is movable with the one or more wheels 1914. In some cases, after reaching the appropriate position, the one or more wheels 1914 can be immobilized using wheel locks to hold the robotic system 110 in place. However, the robotic system 110 can be implemented as a stationary system, integrated into another system/device, and so on.

In some embodiments, one or more of the components of the robotic system 110 can be electrically and/or communicatively coupled using certain connectivity circuitry/devices/features, which can or may not be part of the control circuitry 1902. For example, the connectivity feature(s) can include one or more printed circuit boards configured to facilitate mounting and/or interconnectivity of at least some of the various components/circuitry of the robotic system 110. Although certain components of the robotic system 110 are illustrated in FIG. 18, it should be understood that additional components not shown can be included in embodiments in accordance with the present disclosure. Furthermore, certain of the illustrated components can be omitted in some embodiments.

The support structure 114 can include a base 1916, an elongated column 1918, and/or a console 1920 at the top of the column 1918. The column 1918 can include one or more arm supports 1922 (also referred to as a "carriage") for supporting the deployment of the one or more robotic arms 112 (three shown in FIG. 19). The arm support 1922 can include individually-configurable arm mounts that rotate along a perpendicular axis to adjust the base of the robotic arms 112 for better positioning relative to a patient. The arm support 1922 also includes a column interface 1924 that allows the arm support 1922 to vertically translate along the column 1916. In some embodiments, the column interface 1922 can be connected to the column 1918 through slots, such as slot 1926, that are positioned on opposite sides of the column 1918 to guide the vertical translation of the arm support 1922. The slot 1926 contains a vertical translation interface to position and hold the arm support 1922 at various vertical heights relative to the base 1916. Vertical translation of the arm support 1922 allows the robotic system 110 to adjust the reach of the robotic arms 112 to meet a variety of table heights, patient sizes, and/or physician preferences. Similarly, the individually-configurable arm mounts on the arm support 1922 can allow the base 1916 to be angled in a variety of configurations.

The robotic arms 112 may generally comprise robotic arm bases 1928 and end effectors 1930, separated by a series of linkages 1932 (also referred to as "arm segments") that are connected by a series of joints 1934, each joint comprising one or more independent actuators 1912. Each actuator may comprise an independently-controllable motor. Each independently-controllable joint 1934 can provide or represent an independent degree of freedom available to the robotic arm. In some embodiments, each of the arms 112 has seven joints, and thus provides seven degrees of freedom, including "redundant" degrees of freedom. Redundant degrees of freedom allow the robotic arms 112 to position their respective end effectors 1930 at a specific position, orientation, and/or trajectory in space using different linkage positions and joint angles. This allows for the robotic system 110 to position and direct a medical instrument from a desired point in space while allowing a physician to move the arm joints into a clinically advantageous position away from the patient to create greater access, while avoiding arm collisions.

Each end effector 1930 can comprise an instrument device manipulator (IDM), which may be attached using a mechanism changer interface (MCI). In some embodiments, the IDM can be removed and replaced with a different type of IDM, for example, a first type of IDM may manipulate an endoscope, while a second type of IDM may manipulate a laparoscope. The MCI can include connectors to transfer pneumatic pressure, electrical power, electrical signals, and/or optical signals from the robotic arm 112 to the IDM. The IDMs may be configured to manipulate medical instruments (e.g., surgical tools/instruments) using techniques including, for example, direct drive, harmonic drive, geared drives, belts and pulleys, magnetic drives, and the like.

The robotic system base 1916 can balance the weight of the column 1918, the arm support 1920, and/or arms 112 over the floor. Accordingly, the robotic system base 1916 can house heavier components, such as electronics, motors, power supply, as well as components that selectively enable movement or immobilize the robotic system 110. In examples, such as that illustrated in FIG. 19, the robotic system base 1916 includes wheel-shaped casters 1914 that allow for the robotic system to easily move around the room prior to a procedure. After reaching the appropriate position, the casters 1914 can be immobilized using wheel locks to hold the robotic system 110 in place during the procedure.

Positioned at the upper end of column 1918, the console 1920 allows for both a user interface for receiving user input and the display screen 116 (or a dual-purpose device such as, for example, a touchscreen) to provide a physician/user with pre-operative and/or intra-operative data. Potential pre-operative data can include pre-operative plans, navigation and mapping data derived from pre-operative computerized tomography (CT) scans, and/or notes from pre-operative patient interviews. Intra-operative data can include optical information provided from the tool, sensor and coordinate information from sensors, as well as vital patient statistics, such as respiration, heart rate, and/or pulse. The console 1920 can be positioned and tilted to allow a physician to access the console 1920 from the side of the column 1918 opposite the arm support 1922. From this position, the physician may view the console 1920, the robotic arms 112, and/or patient while operating the console 1920 from behind the robotic system 110. As shown, the console 1920 can also include a handle 1936 to assist with maneuvering and stabilizing robotic system 110.

Example Control System

Figure 20:
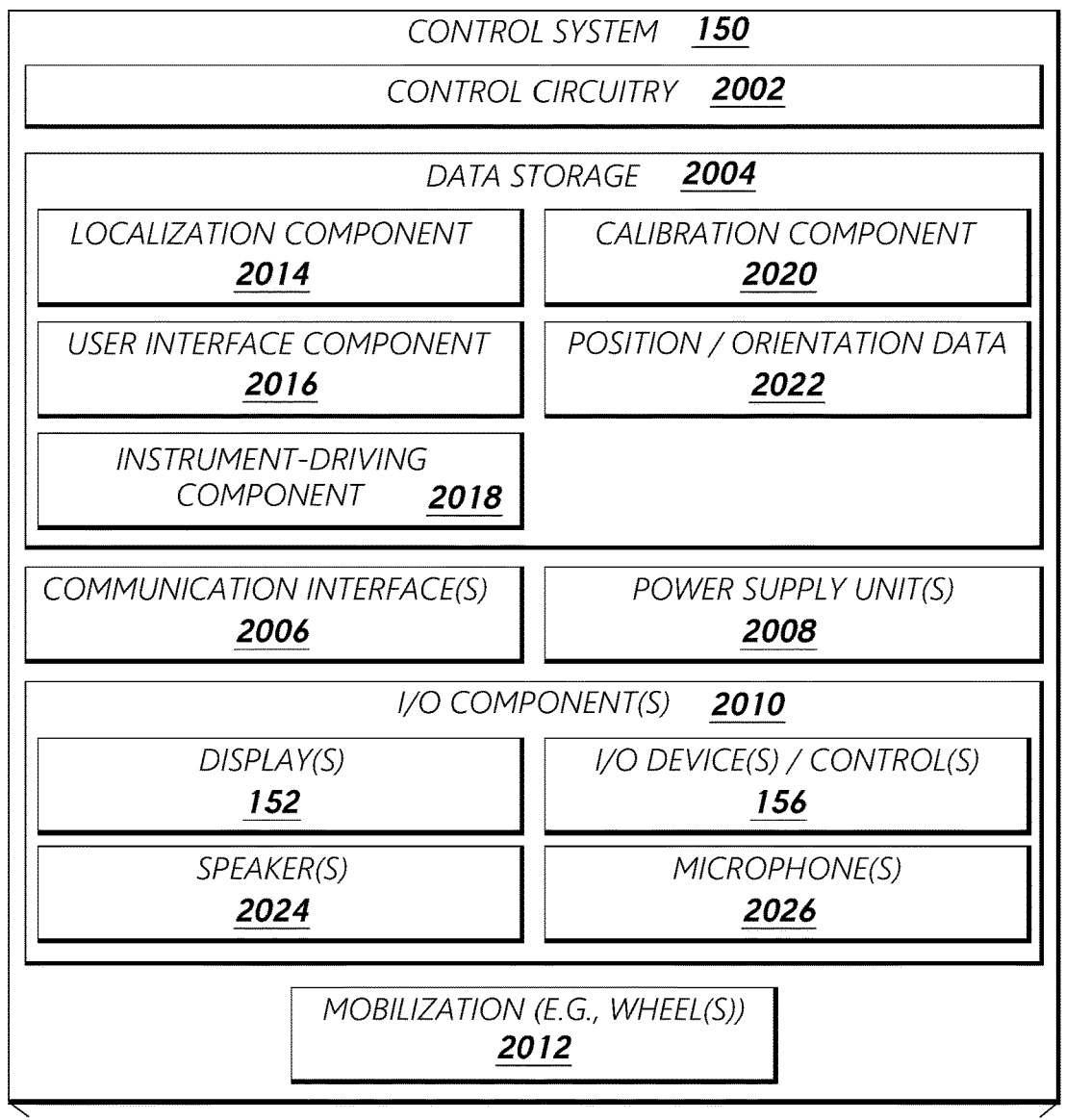
FIG. 20 illustrates example details of the control system of FIG. 1 in accordance with one or more embodiments.

FIG. 20 illustrates example details of the control system 150 from FIG. 1 in accordance with one or more embodiments. As illustrated, the control system 150 can include one or more of the following components, devices, modules, and/or units (referred to herein as "components"), either separately/individually and/or in combination/collectively: control circuitry 2002, data storage/memory 2004, one or more communication interfaces 2006, one or more power supply units 2008, one or more input/output (I/O) components 2010, and/or mobilization 2012 (e.g., casters or other types of wheels). In some embodiments, the control system 150 can comprise a housing/enclosure configured and/or dimensioned to house or contain at least part of one or more of the components of the control system 150. In this example, the control system 150 is illustrated as a cart-based system that is movable with the one or more wheels 2012. In some cases, after reaching the appropriate position, the one or more wheels 2012 can be immobilized using wheel locks to hold the control system 150 in place. However, the control system 150 can be implemented as a stationary system, integrated into another system/device, and so on.

Although certain components of the control system 150 are illustrated in FIG. 20, it should be understood that additional components not shown can be included in embodiments in accordance with the present disclosure. Furthermore, certain of the illustrated components can be omitted in some embodiments. Although the control circuitry 2002 is illustrated as a separate component in the diagram of FIG. 20, it should be understood that any or all of the remaining components of the control system 150 can be embodied at least in part in the control circuitry 2002. That is, the control circuitry 2002 can include various devices (active and/or passive), semiconductor materials and/or areas, layers, regions, and/or portions thereof, conductors, leads, vias, connections, and/or the like, wherein one or more of the other components of the control system 150 and/or portion(s) thereof can be formed and/or embodied at least in part in/by such circuitry components/devices.

The various components of the control system 150 can be electrically and/or communicatively coupled using certain connectivity circuitry/devices/features, which can or may not be part of the control circuitry 2002. For example, the connectivity feature(s) can include one or more printed circuit boards configured to facilitate mounting and/or interconnectivity of at least some of the various components/circuitry of the control system 150. In some embodiments, two or more of the control circuitry 2002, the data storage/memory 2004, the communication interface(s) 1206, the power supply unit(s) 1208, and/or the I/O component(s) 1210, can be electrically and/or communicatively coupled to each other.

As illustrated, the memory 2004 can include a localization component 2014, a user interface component 2016, an instrument-driving component 2018, and a calibration component 2020 configured to facilitate various functionality discussed herein. In some embodiments, the localization component 2014, the user interface component 2016, the instrument-driving component 2018, and/or the calibration component 2020 can include one or more instructions that are executable by the control circuitry 2002 to perform one or more operations. Although many embodiments are discussed in the context of the components 2014-2020 including one or more instructions that are executable by the control circuitry 2002, any of the components 2014-2020 can be implemented at least in part as one or more hardware logic components, such as one or more application specific integrated circuits (ASIC), one or more field-programmable gate arrays (FPGAs), one or more program-specific standard products (ASSPs), one or more complex programmable logic devices (CPLDs), and/or the like. Furthermore, although the components 2014-2020 are illustrated as being included within the control system 150, any of the components 2014-2020 can be implemented at least in part within another device/system, such as the robotic system 110, the table 170, or another device/system. Similarly, any of the other components of the control system 150 can be implemented at least in part within another device/system.

The localization component 2014 can be configured to perform one or more localization techniques to determine and/or track a position and/or an orientation of an object, such as a medical instrument. For example, the localization component 2014 can process input data (e.g., sensor data from a medical instrument, model data regarding anatomy of a patient, position data of a patient, pre-operative data, robotic command and/or kinematics data, etc.) to generate position/orientation data 2022 for one or more medical instruments. In examples, the position/orientation data 2022 can indicate a location and/or an orientation of one or more medical instruments relative to a frame of reference. The frame of reference can be a frame of reference relative to anatomy of a patient, a known object (e.g., an EM field generator, a robot arm, another medical instrument, etc.), a coordinate system/space, a control frame, and so on. In some implementations, the position/orientation data 1220 can indicate a location and/or an orientation of a distal end of a medical instrument (and/or proximal end, in some cases).

In some embodiments, the localization component 2014 can process pre-operative data to determine a position and/or an orientation of an object. The pre-operative data (sometimes referred to as "mapping data") can be generated by performing computed tomography (CT) scans, such as low dose CT scans. The pre-operative CT images from the scans can be reconstructed into three-dimensional images, which are visualized, e.g. as "slices" of a cutaway view of a patient's internal anatomy. When analyzed in the aggregate, image-based models for anatomical cavities, spaces, and/or structures of the patient's anatomy, such as a patient lung network, the renal anatomy, etc., can be generated. A centerline geometry can be determined and/or approximated from the CT images to develop a three-dimensional volume of the patient's anatomy, referred to as model data (also referred to as "pre-operative model data" when generated using only pre-operative CT scans). Network topological models can also be derived from CT-images.

Further, in some embodiments, the localization component 2014 can perform vision-based techniques to determine a position and/or an orientation of an object. For example, a medical instrument can be equipped with a camera, a range sensor (sometimes referred to as "a depth sensor"), a radar device, etc., to provide sensor data in the form of vision data.

The localization component 2014 can process the vision data to facilitate vision-based location tracking of the medical instrument. For example, a pre-operative model data can be used in conjunction with vision data to enable computer vision-based tracking of a medical instrument (e.g., an endoscope). In examples, using pre-operative model data, the control system 150 can generate a library of expected endoscopic images based on the expected path of travel of a scope, with each image being linked to a location within the model. Intra-operatively, this library can be referenced by the control system 150 in order to compare real-time images and/or other vision data captured at a scope (e.g., a camera at a distal end of an endoscope) to those in the image library to assist with localization.

Moreover, in some embodiments, other types of vision-based techniques can be performed to determine a position and/or an orientation of an object. For example, the localization component 2014 can use feature tracking to determine motion of an image sensor (e.g., a camera or other sensor), and thus, a medical instrument associated with the image sensor. In some cases, the localization component 2014 can identify circular geometries in pre-operative model data that correspond to anatomical lumens and track the change of those geometries to determine which anatomical lumen was selected, as well as the relative rotational and/or translational motion of the medical instrument. Use of a topological map can also enhance vision-based algorithms or techniques. Furthermore, the localization component 2014 can use optical flow, another computer vision-based technique, to analyze displacement and/or translation of image pixels in a video sequence in vision data to infer camera movement. Examples of optical flow techniques can include motion detection, object segmentation calculations, luminance, motion compensated encoding, stereo disparity measurement, etc. By comparing multiple frames over multiple iterations, the localization component 2014 can determine movement and a location of an image sensor (and thus an endoscope).

Furthermore, in some embodiments, the localization component 2014 can use electromagnetic tracking to determine a position and/or an orientation of an object. For example, the localization component 2014 can use real-time EM tracking to determine a real-time location of a medical instrument in a coordinate system/space (and/or relative to another medical instrument) that can be registered to the patient's anatomy, which can be represented by a pre-operative model or other model. In EM tracking, an EM sensor (or tracker) including one or more sensor coils can be embedded in one or more locations and/or orientations in a medical instrument (e.g., a scope, a needle, etc.). The EM sensor can measure a variation in an EM field created by one or more static EM field generators positioned at a known location. The location information detected by the EM sensors can be stored as EM data. The localization component 2014 can process the EM data to determine a position and/or orientation of an object, such as a medical instrument. An EM field generator (or transmitter) can be placed close to the patient (e.g., within a predetermined distance) to create a low intensity magnetic field that an EM sensor can detect. The magnetic field can induce small currents in the sensor coils of the EM sensor, which can be analyzed to determine a distance and/or angle between the EM sensor and the EM field generator. These distances and/or orientations can be intra-operatively "registered" to patient anatomy (e.g., a pre-operative model) in order to determine a geometric transformation that aligns a single location in a coordinate system with a position in the pre-operative model of the patient's anatomy. Once registered, an EM sensor (e.g., an embedded EM tracker) in one or more positions of a medical instrument (e.g., the distal tip of an endoscope, a needle, etc.) can provide real-time indications of a position and/or an orientation the medical instrument through the patient's anatomy.

Additionally, or alternatively, in some embodiments, the localization component 2014 can use robotic command and/or kinematics data to determine a position and/or an orientation of an object. Robotic command and/or kinematics data can be indicative of position/orientation of a robotic arm (e.g., pitch, yaw, etc.) resulting from an articulation command, such as those used during pre-operative calibration and/or during a procedure. In examples, the localization component 2014 can use data indicative of a position/orientation of a robotic arm to determine a position/orientation of a medical instrument attached to the robotic arm. For instance, based on a position/orientation of a robotic arm that is attached to a catheter, command sent to control the catheter, and/or a characteristic(s) of the catheter (e.g., a length of the catheter, capabilities of the catheter, etc.), the localization component 2014 can determine/estimate a position/orientation of the catheter. Further, in examples, the localization component 2014 can use robotic command data to determine how far a medical instrument has been inserted/retracted, such as within a patient, based on commands to control the medical instrument, markings on the medical instrument indicating distance, etc. In some intra-operatively embodiments, calibration measurements can be used in combination with known insertion depth information to estimate a position and/or an orientation of a medical instrument. Alternatively, or additionally, these calculations can be analyzed in combination with EM, vision, and/or topological modeling to estimate a position and/or orientation of a medical instrument.

Further, in some embodiments, the localization component 2014 can use other types of data to determine a position and/or an orientation of an object. For example, the localization component 2014 can analyze sensor data from a shape sensing fiber (e.g., which can provide shape data regarding a location/shape of a medical instrument), an accelerometer, a gyroscope, a satellite-based positioning sensor (e.g., a global positioning system (GPS)), a radiofrequency transceiver, and so on, embedded on a medical instrument. Such data can be indicative of a position and/or an orientation of the medical instrument.

In some embodiments, the localization component 2014 can use input data in combination. For example, the localization component 2014 can use a probabilistic approach where a confidence weight is assigned to a position/orientation determined from multiple forms of input data. To illustrate, if EM data is not as reliable (as may be the case where there is EM interference), the EM data can be associated with a relatively low confidence value and other forms of input data can be relied on, such as vision data, robotic command and kinematics data, and so on.

The user interface component 2016 can be configured to facilitate one or more user interfaces (also referred to as "one or more graphical user interfaces (GUI)"). For example, the user interface component 2016 can generate user interface data representing one or more of the interfaces discussed herein, such as the interface 702 of FIG. 7, the interface 1102 of FIGS. 11-12, and so on. The user interface component 2016 can present one or more visualizations or other information to assist in driving a medical instrument and/or calibrating a control scheme. In examples, the user interface component 2016 can generate a visual representation of image data captured by a scope. The user interface component 2016 can provide user interface data or other data to the one or more displays 156 and/or another display(s) for display of information.

The instrument-driving component 2018 can be configured to drive a medical instrument. For example, the instrument-driving component 2018 can be configured to process directional input signals from the I/O device(s) 156, process position or/orientation data 2022 regarding a medical instrument, generate control signals, send the control signals to the robotic system 110 to control movement of an instrument(s) connected to the robotic system 110, and so on. In some embodiments, the instrument-driving component 2018 can facilitate driving of a medical instrument from a perspective of another medical instrument. Further, in some embodiments, the instrument-driving component 2018 can facilitate one or more driving/control modes to assist a physician in driving a medical instrument, such as a direct control mode, an inverted control mode, and so on.

The calibration component 2020 can be configured to calibrate a control scheme/control frame of reference for a medical instrument. For example, the calibration component 2020 can determine an orientation of a first instrument relative to a second instrument, such as an orientation of a distal end of a catheter relative to a distal end of a scope. In some embodiments, the user interface component 2016 can provide a user interface with image data depicting the first instrument from a perspective of the second instrument and one or more interface elements to enable a physician to identify an orientation of the catheter. The calibration component 2020 can process input from the physician to identify an orientation of the instruments relative to each other. Further, in some embodiments, the calibration component 2020 can analyze image data and/or other sensor data from the first/second instrument to identify an orientation of the instruments relative to each other. Moreover, in some embodiments, other techniques may be used to identify an orientation of the instruments relative to each other. Based on the orientation of the instruments, the calibration component 2020 adjust a control scheme associated with controlling the first/second instrument.

Although not illustrated in FIG. 20, in some embodiments, the data storage 2004 can include a target component configured to determine a position of a target location within the human anatomy and/or a coordinate space/system. A target location can represent a point/point set within the human anatomy and/or a coordinate space/system. For example, the target component can identify one or more points for a target location within a coordinate system, identify coordinates for the one or more points (e.g., X, Y, Z coordinates for each point), and associate the coordinates with the target location. In some embodiments, the target component can use a position and/or orientation of a medical instrument to determine a position of a target location. For example, a scope can be navigated to contact or be within proximity to a target location (e.g., parked in-front of the target location). The localization component 2014 can use localization techniques to determine a position of the scope (e.g., a location of the end of the scope) and/or a position of an object within a field-of-view of the scope. The target component can associate the position of the scope (e.g., the coordinates of the scope) with the target location. Additionally, or alternatively, in some embodiments, a scope can deliver a fiduciary to mark a target location and a position of the fiduciary can be determined.

A target location can represent a fixed or movable point(s) within the human anatomy and/or a coordinate space/system. For example, if a papilla is initially designated as a target location, coordinates for the target location can be determined and updated as the procedure proceeds and the papilla moves (e.g., due to insertion of a medical instrument). Here, a location of a scope (which can be within proximity to the papilla) can be tracked over time and used to update the coordinates of the target location. In some embodiments, the target component can estimate/predict a position of a target location. Here, the target location can be represented with the predicted position. For example, the target component can use an algorithm to predict coordinates of the target location as the human anatomy moves. The predicted coordinates can be used to determine a target trajectory.

The one or more communication interfaces 2006 can be configured to communicate with one or more device/sensors/systems. For example, the one or more communication interfaces 2006 can send/receive data in a wireless and/or wired manner over a network. A network in accordance with embodiments of the present disclosure can include a local area network (LAN), wide area network (WAN) (e.g., the Internet), personal area network (PAN), body area network (BAN), etc. In some embodiments, the one or more communication interfaces 2006 can implement a wireless technology such as Bluetooth, Wi-Fi, near field communication (NFC), or the like.

The one or more power supply units 2008 can be configured to manage power for the control system 150 (and/or the robotic system 110, in some cases). In some embodiments, the one or more power supply units 2008 (and/or any other power supply unit) can include one or more batteries, such as a lithium-based battery, a lead-acid battery, an alkaline battery, and/or another type of battery. That is, the one or more power supply units 2008 can comprise one or more devices and/or circuitry configured to provide a source of power and/or provide power management functionality. Moreover, in some embodiments, the one or more power supply units 2008 include a mains power connector that is configured to couple to an alternating current (AC) or direct current (DC) mains power source.

The one or more I/O components 2010 can include a variety of components to receive input and/or provide output, such as to interface with a user. The one or more I/O components 2010 can be configured to receive touch, speech, gesture, or any other type of input. In examples, the one or more I/O components 2010 can be used to provide input regarding control of a device/system, such as to control the robotic system 110, navigate a medical instrument attached to the robotic system 110, control the table 170, control a fluoroscopy device, and so on. As shown, the one or more I/O components 2010 can include the one or more displays 152 (sometimes referred to as "the one or more display devices 152") configured to display data. The one or more displays 152 can include one or more liquid-crystal displays (LCD), light-emitting diode (LED) displays, organic LED displays, plasma displays, electronic paper displays, and/or any other type(s) of technology. In some embodiments, the one or more displays 152 include one or more touchscreens configured to receive input and/or display data. Further, the one or more I/O components 2010 can include the one or more I/O devices/controls 156, which can include a touchscreen, touch pad, controller, mouse, keyboard, wearable device (e.g., optical head-mounted display), virtual or augmented reality device (e.g., head-mounted display), etc. Additionally, the one or more I/O components 2010 can include one or more speakers 2024 configured to output sounds based on audio signals and/or one or more microphones 2026 configured to receive sounds and generate audio signals. In some embodiments, the one or more I/O components 2010 include or are implemented as a console.

Although not shown in FIG. 20, the control system 150 can include and/or control other components, such as one or more pumps, flow meters, valve controls, and/or fluid access components in order to provide controlled irrigation and/or aspiration capabilities to a medical instrument (e.g., a scope), a device that can be deployed through a medical instrument, and so on. In some embodiments, irrigation and/or aspiration capabilities can be delivered directly to a medical instrument through separate cable(s). Further, the control system 150 can include a voltage and/or surge protector designed to provide filtered and/or protected electrical power to another device, such as the robotic system 110, thereby avoiding placement of a power transformer and other auxiliary power components in robotic system 110, resulting in a smaller, more moveable robotic system 110.

The control system 150 can also include support equipment for sensors deployed throughout the medical system 100. For example, the control system 150 can include opto-electronics equipment for detecting, receiving, and/or processing data received from optical sensors and/or cameras. Such opto-electronics equipment can be used to generate real-time images for display in any number of devices/systems, including in the control system 150. Similarly, the control system 150 can include an electronic subsystem for receiving and/or processing signals received from deployed electromagnetic (EM) sensors. In some embodiments, the control system 150 can also be used to house and position an EM field generator for detection by EM sensors in or on a medical instrument.

In some embodiments, the control system 150 can be coupled to the robotic system 110, the table 170, a medical instrument, etc., through one or more cables or connections (not shown). In some implementations, support functionality from the control system 150 can be provided through a single cable, simplifying and de-cluttering an operating room. In other implementations, specific functionality can be coupled in separate cabling and connections. For example, while power can be provided through a single power cable, the support for controls, optics, fluidics, and/or navigation can be provided through a separate cable.

The term "control circuitry" (e.g., the control circuitry 1902, the control circuitry 2002, and/or any other control circuitry) is used herein according to its broad and ordinary meaning, and can refer to any collection of one or more processors, processing circuitry, processing modules/units, chips, dies (e.g., semiconductor dies including come or more active and/or passive devices and/or connectivity circuitry), microprocessors, micro-controllers, digital signal processors, microcomputers, central processing units, graphics processing units, field programmable gate arrays, programmable logic devices, state machines (e.g., hardware state machines), logic circuitry, analog circuitry, digital circuitry, and/or any device that manipulates signals (analog and/or digital) based on hard coding of the circuitry and/or operational instructions. Control circuitry can further comprise one or more, storage devices, which can be embodied in a single memory device, a plurality of memory devices, and/or embedded circuitry of a device. Such data storage can comprise read-only memory, random access memory, volatile memory, non-volatile memory, static memory, dynamic memory, flash memory, cache memory, data storage registers, and/or any device that stores digital information. It should be noted that in embodiments in which control circuitry comprises a hardware state machine (and/or implements a software state machine), analog circuitry, digital circuitry, and/or logic circuitry, data storage device(s)/register(s) storing any associated operational instructions can be embedded within, or external to, the circuitry comprising the state machine, analog circuitry, digital circuitry, and/or logic circuitry.

The term "memory" is used herein according to its broad and ordinary meaning and can refer to any suitable or desirable type of computer-readable media. For example, computer-readable media can include one or more volatile data storage devices, non-volatile data storage devices, removable data storage devices, and/or nonremovable data storage devices implemented using any technology, layout, and/or data structure(s)/protocol, including any suitable or desirable computer-readable instructions, data structures, program modules, or other types of data.

One or more computer-readable media that can be implemented in accordance with embodiments of the present disclosure includes, but is not limited to, phase change memory, static random-access memory (SRAM), dynamic random-access memory (DRAM), other types of random access memory (RAM), read-only memory (ROM), electrically erasable programmable read-only memory (EEPROM), flash memory or other memory technology, compact disk read-only memory (CD-ROM), digital versatile disks (DVD) or other optical storage, magnetic cassettes, magnetic tape, magnetic disk storage or other magnetic storage devices, or any other non-transitory medium that can be used to store information for access by a computing device. As used in certain contexts herein, computer-readable media may not generally include communication media, such as modulated data signals and carrier waves. As such, computer-readable media should generally be understood to refer to non-transitory media.

Example I/O Device

Figure 21A:
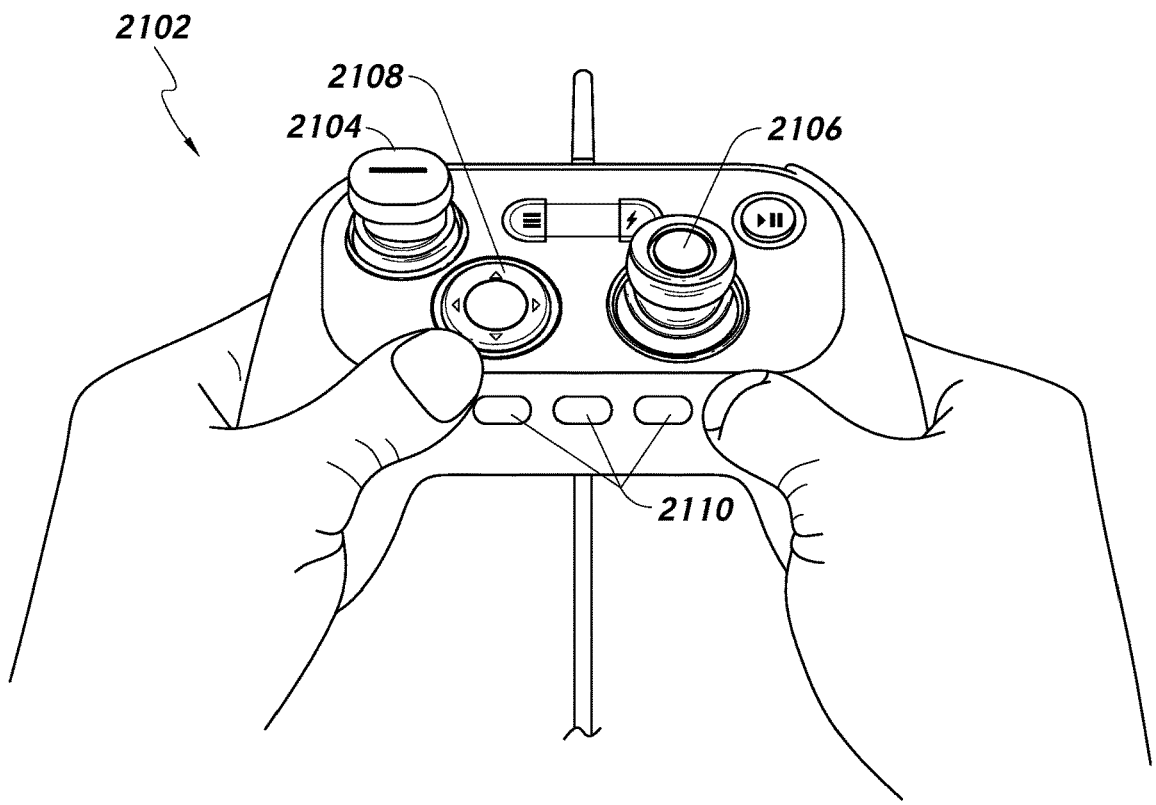
FIGS. 21A and 21B illustrate example details of a controller in accordance with one or more embodiments.
Figure 21B:
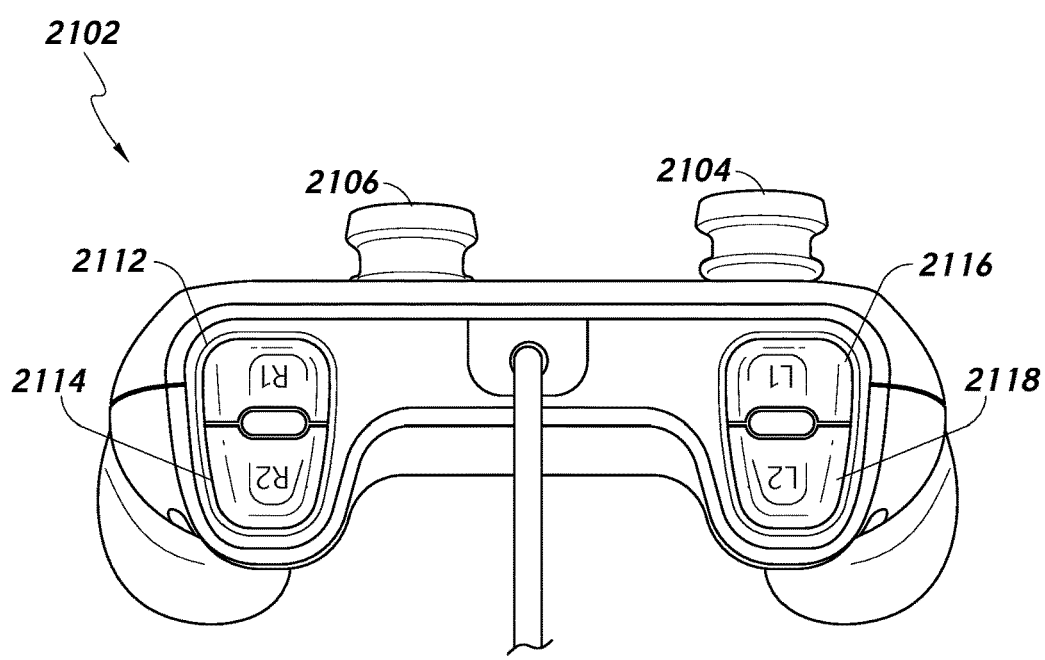

FIGS. 21A and 21B illustrate example details of a controller 2102 in accordance with one or more embodiments. In examples, the I/O device(s) 156 of the control system 150 and/or another I/O device discussed herein is implemented as the controller 2102. However, the I/O device(s) 156 can be implemented as other types of devices. FIG. 21A and FIG. 21B illustrates a perspective view and a side view of the controller 2102, respectively, according to certain embodiments.

The controller 2102 can receive/facilitate axis movement inputs, such via one or more joysticks 2104, 2106 and/or one or more directional pads 2108. For example, a user can manipulate the one or more joysticks 2104, 2106 (and/or the one or more directional pads 2108, in some cases) to provide directional input to control a medical instrument. In some embodiments, the joysticks 2104, 2106 provide analog input while the directional pad 2108 provides digital input. However, any of the joysticks 2104, 2106 and/or the directional pad 2108 can provide analog and/or digital input. In examples, input received via the one or more directional pads 2108 can be used to control a user interface, while input received via the one or more joysticks 2104, 2106 can be used to control movement of a medical instrument. The controller 2102 can further include a plurality of buttons 2110 to provide additional control input. In the example illustrated in FIG. 21B, the controller 2102 includes four buttons on the side of the controller: R1 2112, R2 2114, L1 2116, and L2 2118. Other embodiments can include a different number of buttons and/or a different layout. In some embodiments, the controller 2102 can be a game-type console controller (and/or similar to a game-type console controller) repurposed to work with the control system 150. For example, controller game firmware may be overwritten with a medical device firmware and/or an input device manager can be installed in a component of the medical system 100 (e.g., the control system 150) to convert inputs from the controller 2102 into inputs understandable by the robotic system 110.

The controller 2102 can be implemented to receive input to control/drive a medical instrument. For example, the joysticks 2104, 2104 can receive directional input indicative of a direction to move a medical instrument (e.g., right, left, diagonal, up, down, insert, retract, etc.). To illustrate, a user can tilt the joystick 2106 to the left/right to cause a catheter/scope to move in a left/right direction (which can depend on a control mode) relative to a control frame, as discussed above. In another illustrate, a user can push/tilt the joystick 2104 forward/back relative to FIG. 21A to cause a catheter/scope to be inserted/retracted (depending on a control mode). Although certain controls are discussed as mapping to certain functionality, the controller 2102 can be configured in a variety of other manners. In some embodiments, the controller 2102 can be customized with a user interface that allows assigning of functionality to a particular control on the controller 2102.

In some embodiments, the controller 2102 can implement a control (e.g., one or more of the controls 2104-2118 and/or other controls) to facilitate switching between different medical instruments. For example, a user can select one of the buttons 2110 to switch from driving a scope to driving a catheter. Further, the controller 2102 can implement a control to switch between control/driving modes for a medical instrument(s), such as a direct control mode, an inverted control mode, etc. Moreover, the controller 2102 can implement a control to navigate to a specific interface, such as a driving interface, a calibration interface.

ADDITIONAL EMBODIMENTS

Depending on the embodiment, certain acts, events, or functions of any of the processes or algorithms described herein can be performed in a different sequence, may be added, merged, or left out altogether. Thus, in certain embodiments, not all described acts or events are necessary for the practice of the processes.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is understood with the context as used in general to convey that an item, term, element, etc. may be either X, Y, or Z. Thus, such conjunctive language is not generally intended to imply that certain embodiments require at least one of X, at least one of Y, and at least one of Z to each be present.

It should be appreciated that in the above description of embodiments, various features are sometimes grouped together in a single embodiment, figure, or description thereof for the purpose of streamlining the disclosure and aiding in the understanding of one or more of the various aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the disclosure herein disclosed and claimed below should not be limited by the particular embodiments described above, but should be determined only by a fair reading of the claims that follow.

It should be understood that certain ordinal terms (e.g., "first" or "second") may be provided for ease of reference and do not necessarily imply physical characteristics or ordering. Therefore, as used herein, an ordinal term (e.g., "first," "second," "third," etc.) used to modify an element, such as a structure, a component, an operation, etc., does not necessarily indicate priority or order of the element with respect to any other element, but rather may generally distinguish the element from another element having a similar or identical name (but for use of the ordinal term). In addition, as used herein, indefinite articles ("a" and "an") may indicate "one or more" rather than "one." Further, an operation performed "based on" a condition or event may also be performed based on one or more other conditions or events not explicitly recited.

Unless otherwise defined, all terms (including technical and scientific terms) used herein have the same meaning as commonly understood by one of ordinary skill in the art to which example embodiments belong. It be further understood that terms, such as those defined in commonly used dictionaries, should be interpreted as having a meaning that is consistent with their meaning in the context of the relevant art and not be interpreted in an idealized or overly formal sense unless expressly so defined herein.

The spatially relative terms "outer," "inner," "upper," "lower," "below," "above," "vertical," "horizontal," and similar terms, may be used herein for ease of description to describe the relations between one element or component and another element or component as illustrated in the drawings. It be understood that the spatially relative terms are intended to encompass different orientations of the device in use or operation, in addition to the orientation depicted in the drawings. For example, in the case where a device shown in the drawing is turned over, the device positioned "below" or "beneath" another device may be placed "above" another device. Accordingly, the illustrative term "below" may include both the lower and upper positions. The device may also be oriented in the other direction, and thus the spatially relative terms may be interpreted differently depending on the orientations.

Unless otherwise expressly stated, comparative and/or quantitative terms, such as "less," "more," "greater," and the like, are intended to encompass the concepts of equality. For example, "less" can mean not only "less" in the strictest mathematical sense, but also, "less than or equal to."

What is claimed is:

1. A control system comprising:
a communication interface configured to receive image data from a first instrument that is configured to access an anatomical site via a first access path, the image data representative of the anatomical site and a second instrument that is configured to access the anatomical site via a second access path; and
control circuitry communicatively coupled to the communication interface and configured to:
cause a visual representation of the image data to be displayed in a user interface;
receive a first directional input signal from an input device;
determine an orientation of the first instrument relative to the second instrument; and
control movement of the second instrument based at least in part on the first directional input signal and the orientation of the first instrument relative to the second instrument.

2. The control system of claim 1, wherein:
the first directional input signal is associated with a first direction relative to the input device, the first direction being associated with a first horizontal component; and
the control circuitry is configured to:
determine to control the second instrument in an inverted control mode; and
based at least in part on the inverted control mode, control the second instrument to move in a second direction relative to a frame of reference for the second instrument, the second direction being associated with a second horizontal component that has an opposite sign to the first horizontal component.

3. The control system of claim 2, wherein the frame of reference for the second instrument comprises at least one of a control frame for the second instrument or a coordinate frame for the second instrument.

4. The control system of claim 1, wherein:
the first directional input signal is associated with a first direction relative to the input device, the first direction being associated with a first horizontal component; and
the control circuitry is configured to:
determine to control the second instrument in a direct control mode; and
based at least in part on the direct control mode, control the second instrument to move in a second direction relative to a frame of reference for the second instrument, the second direction being associated with a second horizontal component that has a same sign as the first horizontal component.

5. The control system of claim 1, wherein:
the first directional input signal is associated with a first direction relative to the input device, the first direction being associated with a first horizontal component; and
the control circuitry is configured to:
determine to control the second instrument in an inverted control mode;
based at least in part on the inverted control mode, control the second instrument to move in a second direction relative to a frame of reference for the second instrument, the second direction being associated with a second horizontal component that has an opposite sign to the first horizontal component;
determine to control the second instrument in a direct control mode;
receive a second directional input signal from the input device, the second directional input signal being associated with a third direction relative to the input device, the third direction being associated with a third horizontal component; and based at least in part on the direct control mode, control the second instrument to move a fourth direction relative to the frame of reference for the second instrument, the fourth direction being associated with a fourth horizontal component that has a same sign as the third horizontal component.

6. The control system of claim 1, wherein:
the first directional input signal is based at least in part on input received via a directional control on the input device;
the control circuitry is configured to:
determine to control the second instrument in an inverted control mode;
based on the directional control being associated with insertion, control the second instrument to be retracted; and
based on the directional control being associated with retraction, control the second instrument to be inserted.

7. The control system of claim 1, wherein the control circuitry is configured to:
determine a control mode from among a plurality of control modes based at least in part on the orientation of the first instrument relative to the second instrument; and
control the movement of the second instrument based at least in part on the control mode.

8. A system comprising:
a first robotic manipulator configured to manipulate a direct access instrument at a target anatomical site;
a second robotic manipulator configured to manipulate a percutaneous access instrument at the target anatomical site;
a user input device including a directional control, the user input device being configured to receive user input via the directional control and generate a first directional input signal based at least in part on the user input; and
control circuitry communicatively coupled to the first robotic manipulator, the second robotic manipulator, and the user input device, the control circuitry being configured to:
receive image data from the direct access instrument, the image data representing at least a portion of the percutaneous access instrument;
generate user interface data representing the image data;
determine an orientation of the direct access instrument relative to the percutaneous access instrument; and
control the second robotic manipulator based at least in part on the first directional input signal and the orientation of the direct access instrument relative to the percutaneous access instrument.

9. The system of claim 8, wherein:
the first directional input signal is associated with a first direction relative to the user input device, the first direction being associated with a first horizontal or vertical component; and
the control circuitry is configured to control the second robotic manipulator to move the percutaneous access instrument in a second direction relative to a frame of reference for the percutaneous access instrument based at least in part on an inverted control mode, the second direction being associated with a second horizontal or vertical component that has an opposite sign to the first horizontal or vertical component.

10. The system of claim 9, wherein the control circuitry is further configured to determine the inverted control mode based on at least one of input received via a user interface or input received via the user input device.

11. The system of claim 9, wherein the control circuitry is further configured to:
determine the inverted control mode based at least in part on the orientation of the direct access instrument relative to the percutaneous access instrument.

12. The system of claim 9, wherein the first horizontal or vertical component is left or right.

13. The system of claim 8, wherein:
the first directional input signal is associated with a first direction relative to the user input device, the first direction being associated with a first horizontal or vertical component; and
the control circuitry is configured to control the second robotic manipulator to move the percutaneous access instrument in a second direction relative to a frame of reference for the percutaneous access instrument, the second direction being associated with a second horizontal or vertical component that has a same sign as the first horizontal or vertical component.

14. The system of claim 8, wherein the control circuitry is further configured to:
receive an input signal indicating to switch control to the direct access instrument;
based at least in part on the input signal, configure the system to control the direct access instrument;
receive, from the user input device, a second directional input signal; and
control the direct access instrument based at least in part on the second directional input signal.

15. The system of claim 8, wherein the direct access instrument comprises an endoscope and the percutaneous access instrument comprises a catheter.

16. A method comprising:
receiving, by control circuitry, image data from an endoscope that is configured to access an anatomical site via a first access path, the image data representing at least a portion of a catheter that is configured to access the anatomical site via a second access path;
displaying a visual representation of the image data in a user interface;
receiving, by the control circuitry and from an input device, a first directional input signal;
determining an orientation of the endoscope relative to the catheter; and
controlling, by the control circuitry, movement of the catheter based at least in part on the first directional input signal and the orientation of the endoscope relative to the catheter.

17. The method of claim 16, further comprising:
determining an inverted control mode for the catheter;
wherein the first directional input signal is associated with a first direction relative to the input device, the first direction being associated with a first horizontal component; and
wherein the controlling movement of the catheter is based at least in part on the inverted control mode, the catheter being controlled to move in a second direction relative to a frame of reference for the catheter, the second direction being associated with a second horizontal component that has an opposite sign to the first horizontal component.

18. The method of claim 17, further comprising:
receiving, via at least one of the input device or the user interface, input indicating the inverted control mode; and
wherein the determining the inverted control mode is based at least in part on the input.

19. The method of claim 17, wherein the determining the inverted control mode is based at least in part on the orientation of the endoscope relative to the catheter.

20. The method of claim 17, further comprising:
determining a direct control mode for the catheter;
receiving, from the input device, a second directional input signal that is associated with a third direction relative to the input device, the third direction being associated with a third horizontal component; and
controlling movement of the catheter based at least in part on the direct control mode, the catheter being controlled to move in a fourth direction relative to the frame of reference for the catheter, the fourth direction being associated with a fourth horizontal component that has a same sign as the third horizontal component.

21. The method of claim 16, further comprising:
receiving an input signal indicating to switch control to the endoscope;
receiving, from the input device, a second directional input signal; and
controlling movement of the endoscope based at least in part on the input signal and the second directional input signal.

22. The method of claim 16, wherein the first access path comprises a natural lumen in a patient and the second access path comprises a percutaneous access path in the patient.

23. One or more non-transitory computer-readable media storing computer-executable instructions that, when executed by control circuitry, cause the control circuitry to perform operations comprising:
receiving image data from an endoscope that is configured to access an anatomical site via a first access path, the image data representing at least a portion of a catheter that is configured to access the anatomical site via a second access path;
causing a visual representation of the image data to be displayed in a user interface;
receiving, from an input device, a first directional input signal; and
controlling movement of the catheter based at least in part on the first directional input signal and an orientation of the endoscope relative to the catheter.

24. The one or more non-transitory computer-readable media of claim 23, wherein the operations further comprise:
determining a first control mode for the catheter;
wherein the first directional input signal is associated with a first direction relative to the input device, the first direction being associated with a first horizontal component; and
wherein the controlling movement of the catheter is based at least in part on the first control mode, the catheter being controlled to move in a second direction relative to a frame of reference for the catheter, the second direction being associated with a second horizontal component that has an opposite sign to the first horizontal component.

25. The one or more non-transitory computer-readable media of claim 24, wherein the frame of reference for the catheter comprises at least one of a control frame for the catheter or a coordinate frame for the catheter.

26. The one or more non-transitory computer-readable media of claim 24, wherein the determining the first control mode is based at least in part on the orientation of the endoscope relative to the catheter.

27. The one or more non-transitory computer-readable media of claim 24, wherein the operations further comprise:
determining a second control mode for the catheter;
receiving, from the input device a second directional input signal that is associated with a third direction relative to the input device, the third direction being associated with a third horizontal component; and
controlling movement of the catheter based at least in part on the second control mode, the catheter being controlled to move in a fourth direction relative to the frame of reference for the catheter, the fourth direction being associated with a fourth horizontal component that has a same sign as the third horizontal component.

28. The one or more non-transitory computer-readable media of claim 23, wherein the operations further comprise:
receiving an input signal indicating to switch control to the endoscope;
receiving, from the input device, a second directional input signal; and
controlling movement of the endoscope based at least in part on the input signal and the second directional input signal.

29. The one or more non-transitory computer-readable media of claim 23, wherein the first access path comprises a natural lumen in a patient and the second access path comprises a percutaneous access path in the patient.

30. The one or more non-transitory computer-readable media of claim 23, wherein the anatomical site comprises a cavity within a kidney.

* * * * *